United States Patent
Nimmagadda et al.

(10) Patent No.: US 11,607,466 B2
(45) Date of Patent: Mar. 21, 2023

(54) TUMOR AND IMMUNE CELL IMAGING BASED ON PD-L1 EXPRESSION

(71) Applicant: The Johns Hopkins University, Baltimore, MD (US)

(72) Inventors: Sridhar Nimmagadda, Baltimore, MD (US); Martin Pomper, Baltimore, MD (US); Samit Chatterjee, Baltimore, MD (US); Wojciech Lesniak, Baltimore, MD (US); Dhiraj Kumar, Hamirpur (IN)

(73) Assignee: The Johns Hopkins University, Baltimore, MD (US)

( * ) Notice: Subject to any disclaimer, the term of this patent is extended or adjusted under 35 U.S.C. 154(b) by 185 days.

(21) Appl. No.: 16/471,678

(22) PCT Filed: Dec. 21, 2017

(86) PCT No.: PCT/US2017/068025
§ 371 (c)(1),
(2) Date: Jun. 20, 2019

(87) PCT Pub. No.: WO2018/119313
PCT Pub. Date: Jun. 28, 2018

(65) Prior Publication Data
US 2019/0314531 A1 Oct. 17, 2019

Related U.S. Application Data

(60) Provisional application No. 62/519,534, filed on Jun. 14, 2017, provisional application No. 62/438,575, filed on Dec. 23, 2016.

(51) Int. Cl.
*A61K 51/08* (2006.01)
*A61K 49/00* (2006.01)

(52) U.S. Cl.
CPC ........ *A61K 51/088* (2013.01); *A61K 49/0056* (2013.01)

(58) Field of Classification Search
None
See application file for complete search history.

(56) References Cited

U.S. PATENT DOCUMENTS

| 8,217,149 B2 | 7/2012 | Irving et al. |
| 2014/0294898 A1 | 10/2014 | Miller et al. |
| 2014/0316255 A1 | 10/2014 | Garai et al. |
| 2015/0250906 A1 | 9/2015 | Jain et al. |

FOREIGN PATENT DOCUMENTS

| WO | WO 2016/039749 | 3/2016 |
| WO | WO 2016/086021 | 6/2016 |
| WO | WO 2016/100285 | 6/2016 |
| WO | WO 2016/100608 | 6/2016 |
| WO | WO 2016/126646 | 8/2016 |
| WO | WO 2017/201111 | 11/2017 |

OTHER PUBLICATIONS

Agoram, B. M. Use of pharmacokinetic/ pharmacodynamic modelling for starting dose selection in first-in-human trials of high-risk biologies. Br J Clin Pharmacol. Feb. 2009;67(2):153-60.
Anderson, C. J., et al. Copper-64 radiopharmaceuticals for PET imaging of cancer: advances in preclinical and clinical research. Cancer Biother Radiopharm. Aug. 2009;24(4):379-93.
Boswell, C. A., et al. Comparative in vivo stability of copper-64-labeled cross-bridged and conventional tetraazamacrocyclic complexes. J Med Chem. Mar. 11, 2004;47(6):1465-74.
Brahmer, J. R., et al. (2012) Safety and activity of anti-PD-L1 antibody in patients with advanced cancer. N Engl J Med. Jun. 28, 2012;366(26):2455-65.
Chang et al., Blocking of the PD-1/PD-L1 Interaction by a D-Peptide Antagonist for Cancer Immunotherapy. Angew. Chem. Int. Ed., 2015, 54:11760-11764.
Chatterjee, S. et al., Rapid PD-L1 detection in tumors with PET using a highly specific peptide. Biochem Biophys Res Commun. Jan. 29, 2017;483(1):258-263.
Chatterjee, S., et al. A humanized antibody for imaging immune checkpoint ligand PD-L1 expression in tumors. Oncotarget. Mar. 1, 2016;7(9): 10215-27.
Deng, R., et al. Preclinical pharmacokinetics, pharmacodynamics, tissue distribution, and tumor penetration of anti-PD-L1 monoclonal antibody, an immune checkpoint inhibitor. MAbs. 2016;8(3):593-603.
Friesner, R. A., et al., Glide: a new approach for rapid, accurate docking and scoring. 1. Method and assessment of docking accuracy. J Med Chem. Mar. 25, 2004;47(7):1739-49.
Gebhart, G., et al. Molecular imaging as a tool to investigate heterogeneity of advanced HER2-positive breast cancer and to predict patient outcome under trastuzumab emtansine (T-DM1): the ZEPHIR trial. Ann Oncol. Apr. 2016;27(4):619-24.
Gibney, G. T., et al. Predictive biomarkers for checkpoint inhibitor-based immunotherapy. Lancet Oncol. Dec. 2016;17(12):e542-e551.
Goel, S., et al. Normalization of the vasculature for treatment of cancer and other diseases. Physiol Rev. Jul. 2011;91(3):1071-121.
Gourni, E., et al. PET of CXCR4 expression by a (68)Ga-labeled highly specific targeted contrast agent. J Nucl Med. Nov. 2011;52(11):1803-10.
Halgren, T. A., et al. Glide: a new approach for rapid, accurate docking and scoring. 2. Enrichment factors in database screening. J Med Chem. Mar. 25, 2004;47(7): 1750-9.
Herbst, R. S., et al. Predictive correlates of response to the anti-PD-L1 antibody MPDL3280A in cancer patients. Nature. Nov. 27, 2014;515(7528):563-7.

(Continued)

*Primary Examiner* — Jennifer Lamberski
(74) *Attorney, Agent, or Firm* — Casimir Jones, S.C.; Jeffrey W. Childers

(57) ABSTRACT

The presently disclosed subject matter provides compositions, kits, and methods comprising imaging agents that can detect Programmed Death Ligand 1 (PD-L1). The presently disclosed imaging agents can be used to detect diseases and disorders, such as cancer, infection, and inflammation, in a subject.

44 Claims, 63 Drawing Sheets

(56) References Cited

OTHER PUBLICATIONS

Herrmann, K., et al. First-in-Human Experience of CXCR4-Directed Endoradiotherapy with 177Lu- and 90Y- Labeled Pentixather in Advanced-Stage Multiple Myeloma with Extensive Intra- and Extramedullary Disease. J Nucl Med, 2016; 57, 248-51.

Heskamp, S., et al. (2015) Noninvasive Imaging of Tumor PD-L1 Expression Using Radiolabeled Anti-PD-L1 Antibodies. Cancer Res. Jul. 15, 2015;75(14):2928-36.

Hettich, M., et al. High-Resolution PET Imaging with Therapeutic Antibody-based PD-1/PD-L1 Checkpoint Tracers Theranostics. Jun. 18, 2016;6(10):1629-40.

Josefsson, A., Nedrow, J. R., Park, S., Banerjee, S. R., Pittenbach, A., Jammes, F., Tsui, B., and Sgouros, G. (2016) Imaging, Biodistribution, and Dosimetry of Radionuclide-Labeled PD-L1 Antibody in an Immunocompetent Mouse Model of Breast Cancer. Cancer Res. Jan. 15, 2016;76(2):472-9.

Kamath, A. V. Translational pharmacokinetics and pharmacodynamics of monoclonal antibodies. Drug Discov Today Technol. Sep.-Dec. 2016;21-22:75-83.

Kelly, S. M., et al. The use of circular dichroism in the investigation of protein structure and function. Curr Protein Pept Sci. Dec. 2000;1(4):349-84.

Lee, H. T., et al. Molecular mechanism of PD-1/PD-L1 blockade via anti-PD-L1 antibodies atezolizumab and durvalumab. Sci Rep. Jul. 17, 2017;7(1):5532.

Lesniak, W. G., et al. PD-L1 Detection in Tumors Using [(64)Cu]Atezolizumab with PET. Bioconjug Chem. Sep. 21, 2016;27(9):2103-10.

Linden, H. M., et al., Quantitative fluoroestradiol positron emission tomography imaging predicts response to endocrine treatment in breast cancer. J Clin Oncol. Jun. 20, 2006;24(18):2793-9.

Lipson, E. J., et al. Antagonists of PD-1 and PD-L1 in Cancer Treatment. Semin Oncol. Aug. 2015;42(4):587-600.

Liu, K., et al. Structural basis of anti-PD-L1 monoclonal antibody avelumab for tumor therapy. Cell Res. Jan. 2017;27(1):151-153.

Maute et al., Engineering high-affinity PD-1 variants for optimized immunotherapy and immuno-PET imaging. Proc Natl Acad Sci U S A. Nov. 24, 2015;112(47):E6506-14.

McLaughlin, J., et al. Quantitative Assessment of the Heterogeneity of PD-L1 Expression in Non-Small-Cell Lung Cancer. JAMA Oncol. Jan. 2016;2(1):46-54.

Meerbrey, K. L., et al. The pINDUCER lentiviral toolkit for inducible RNA interference in vitro and in vivo. Proc Natl Acad Sci USA. Mar. 1, 2011;108(9):3665-70.

Morin, A., et al. Collaboration gets the most out of software. Elife. Sep. 10, 2013;2:e01456.

Nolan, E., et al. Combined immune checkpoint blockade as a therapeutic strategy for BRCA1-mutated breast cancer. Sci Transl Med. Jun. 7, 2017;9(393):eaal4922.

Okazaki, T., et al. PD-1 and PD-1 ligands: from discovery to clinical application. Int Immunol. Jul. 2007;19(7):813-24.

Oosting, S. F., et al. 89Zr-Bevacizumab PET Visualizes Disease Manifestations in Patients with von Hippel-Lindau Disease. J Nucl Med. Aug. 2016;57(8): 1244-50.

Oude Munnink, T. H., et al. Therapeutic drug monitoring of monoclonal antibodies in inflammatory and malignant disease: Translating TNF-alpha experience to oncology. Clin Pharmacol Ther. Apr. 2016;99(4):419-31.

Pandit-Taskar, N., et al. A Phase I/II Study for Analytic Validation of 89Zr-J591 ImmunoPET as a Molecular Imaging Agent for Metastatic Prostate Cancer. Clin Cancer Res. Dec. 1, 2015;21(23):5277-85.

Peterson, L. M., et al. Quantitative imaging of estrogen receptor expression in breast cancer with PET and 18F-fluoroestradiol. Journal of nuclear medicine: official publication, Society of Nuclear Medicine 2008; 49, 367-74.

Phillips, T., et al. Development of an automated PD-L1 immunohistochemistry (IHC) assay for non-small cell lung cancer, Appl Immunohistochem Mol Morphol. Sep. 2015;23(8):541-9.

Powles, T., et al. MPDL3280A (anti-PD-L1) treatment leads to clinical activity in metastatic bladder cancer. Nature. Nov. 27, 2014;515(7528):558-62.

Rathkopf, D. E., et al. Phase I study of ARN-509, a novel antiandrogen, in the treatment of castration-resistant prostate cancer. J Clin Oncol. Oct. 1, 2013;31(28):3525-30.

Reubi, J. C., et al. Peptide-based probes for cancer imaging. J Nucl Med. Nov. 2008;49(11):1735-8.

Roach, C., et al. Development of a Companion Diagnostic PD-L1 Immunohistochemistry Assay for Pembrolizumab Therapy in Non-Small-cell Lung Cancer. Appl Immunohistochem Mol Morphol. Jul. 2016;24(6):392-7.

Sastry, G. M., et al. Protein and ligand preparation: parameters, protocols, and influence on virtual screening enrichments. J Comput Aided Mol Des. Mar. 2013;27(3):221-34.

Sheng, J., et al. Clinical Pharmacology Considerations for the Development of Immune Checkpoint Inhibitors. J Clin Pharmacol. Oct. 2017;57 Suppl 10:S26-S42.

Sreerama, N., et al. Estimation of protein secondary structure from circular dichroism spectra: comparison of CONTIN, SELCON, and CDSSTR methods with an expanded reference set. Anal Biochem. Dec. 15, 2000;287(2):252-60.

Sun, X., et al. Peptide-based imaging agents for cancer detection. Adv Drug Deliv Rev. Feb. 2017; 110-111:38-51.

Sunshine, J., et al. PD-1/PD-L1 inhibitors. Curr Opin Pharmacol. Aug. 2015;23:32-8.

Taube, J. M., et al. Colocalization of inflammatory response with B7-h1 expression in human melanocytic lesions supports an adaptive resistance mechanism of immune escape. Sci Transl Med. Mar. 28, 2012;4(127):127ra37.

Taube, J. M., et al. Differential Expression of Immune-Regulatory Genes Associated with PD-L1 Display in Melanoma: Implications for PD-1 Pathway Blockade. Clin Cancer Res. Sep. 1, 2015;21(17):3969-76.

Topalian, S. L., et al. Immune checkpoint blockade: a common denominator approach to cancer therapy. Cancer Cell. Apr. 13, 2015;27(4):450-61.

Topalian, S. L., et al. Mechanism-driven biomarkers to guide immune checkpoint blockade in cancer therapy. Nat Rev Cancer. May 2016;16(5):275-87.

Wadas, T. J., et al. Copper chelation chemistry and its role in copper radiopharmaceuticals. Curr Pharm Des. 2007;13(1):3-16.

Wang et al., Synthetic small peptides acting on B7H1 enhance apoptosis in pancreatic cancer cells. Molecular Medicine Reports 2012, 6:553-557.

Willmann, J. K., et al. Molecular imaging in drug development. Nat Rev Drug Discov. Jul. 2008;7(7):591-607.

Woodard, L. E., et al. Bridged cyclams as imaging agents for chemokine receptor 4 (CXCR4). Nucl Med Biol. Aug. 2014;41(7):552-61.

Wu, A. M. Engineered antibodies for molecular imaging of cancer. Methods. Jan. 1, 2014;65(1):139-47.

Wu, D., et al. Contrast agents for photoacoustic and thermoacoustic imaging: A review. Int J Mol Sci. Dec. 18, 2014;15(12):23616-39.

Zak, K. M., et al. Structure of the Complex of Human Programmed Death 1, PD-1, and Its Ligand PD-L1. Structure. Dec. 1, 2015;23(12):2341-2348.

Zerda et al., Family of enhanced photoacoustic imaging agents for high-sensitivity and multiplexing studies in living mice. ACS Nano. Jun. 26, 2012;6(6):4694-701.

Extended European Search Report for EP 17883237.4., dated Jul. 9, 2020, 10 pages.

WL12= Cyclo-(-Ac-Tyr-NMeAla-Asn-Pro-His-Leu-Hyp-Trp-Ser-Trp(methyl)-NMeNle-NMeNle-Lys-Cys-)-Gly-NH2

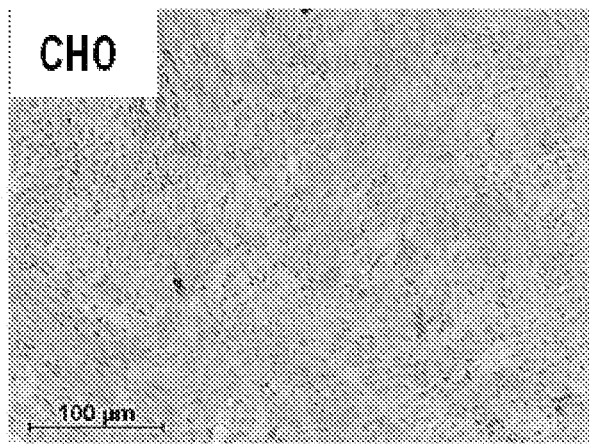
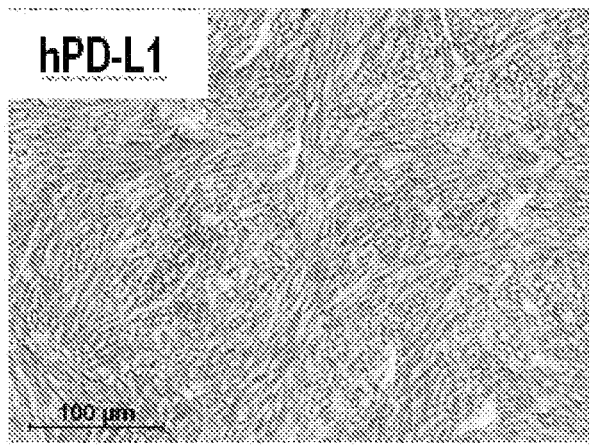
FIG. 15B

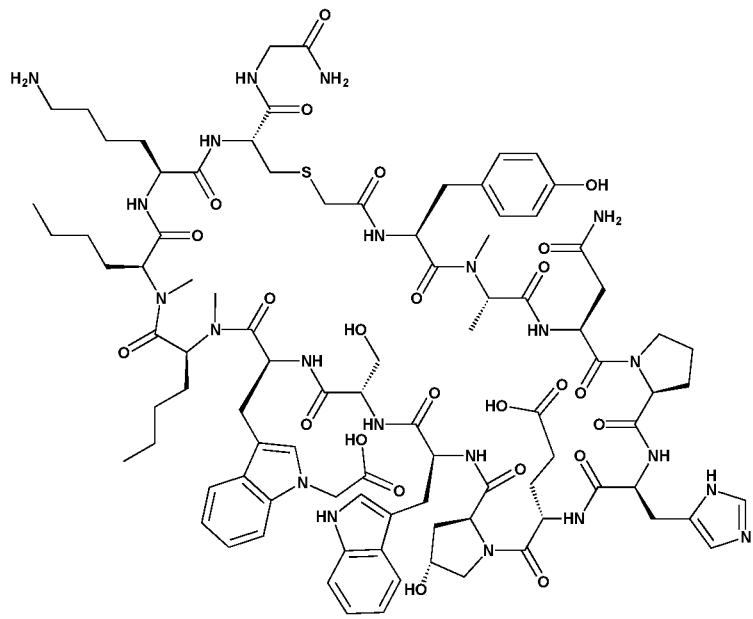
DK-A-221
Chemical Formula: $C_{92}H_{126}N_{22}O_{24}S$
Molecular Weight: 1956.21
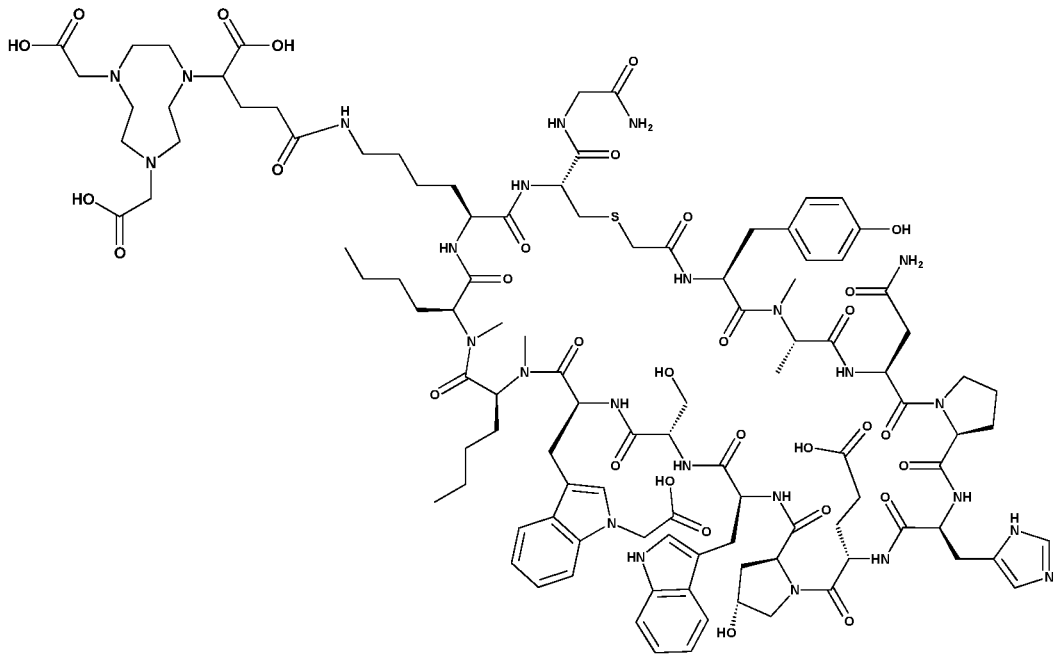
DK-A-222
Chemical Formula: $C_{107}H_{149}N_{25}O_{31}S$
Molecular Weight: 2313.57
*Fig. 30*

*Fig. 31A*
*Fig. 31B*
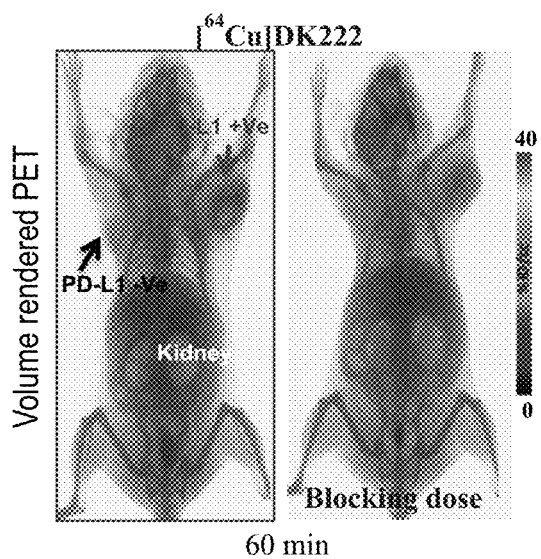
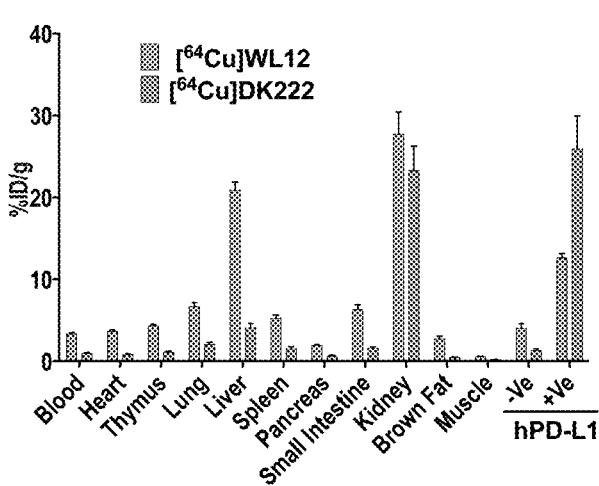

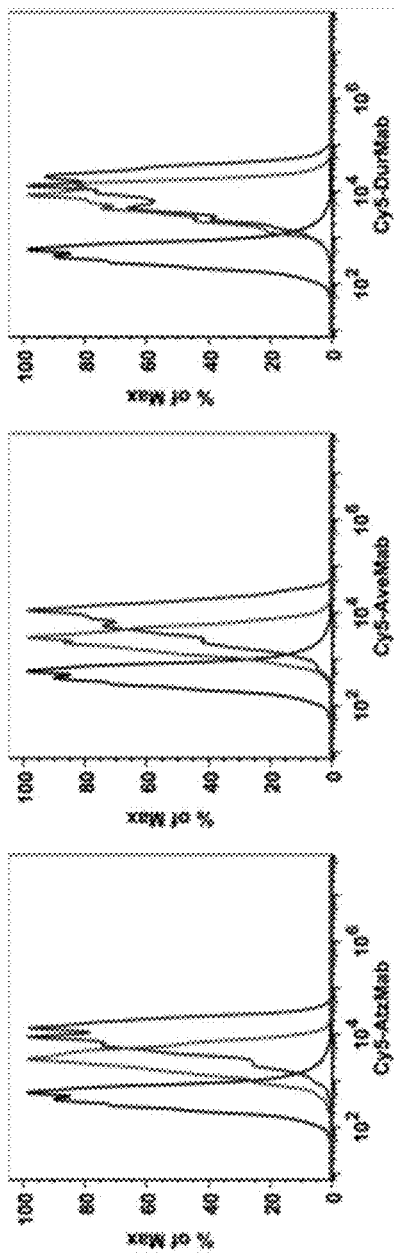
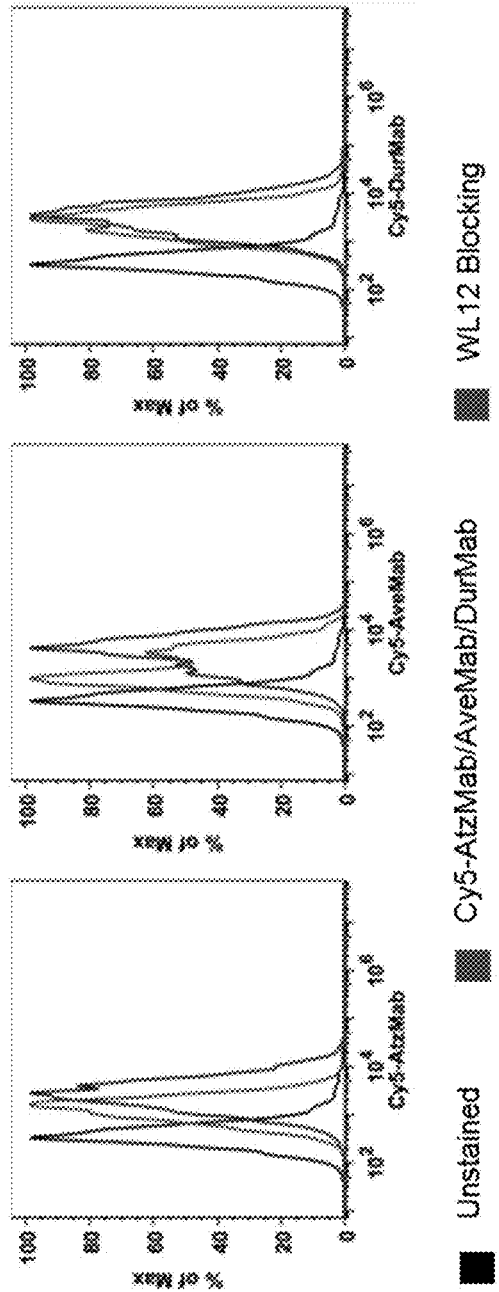
Fig. 34C

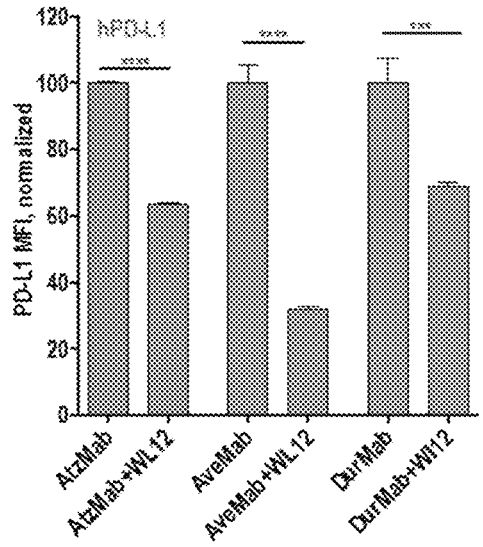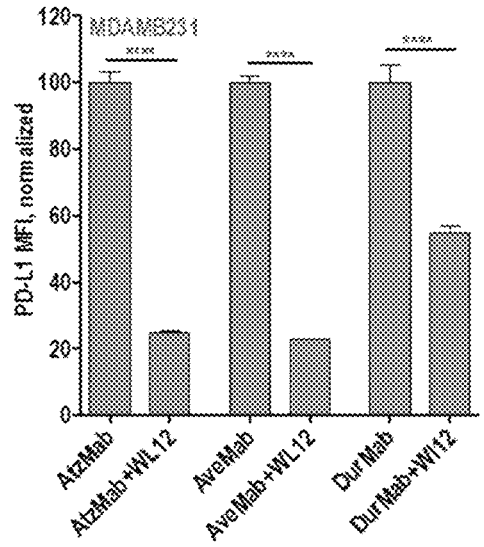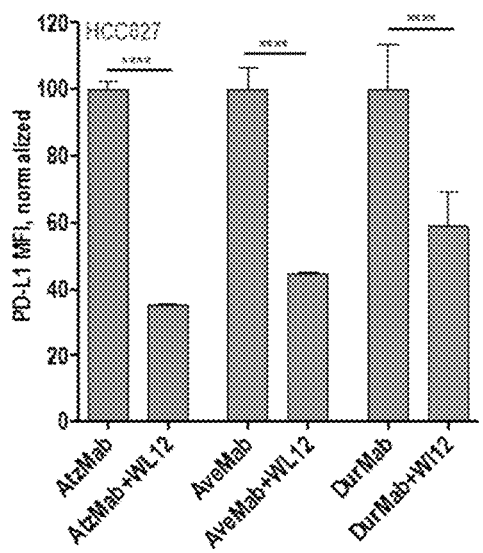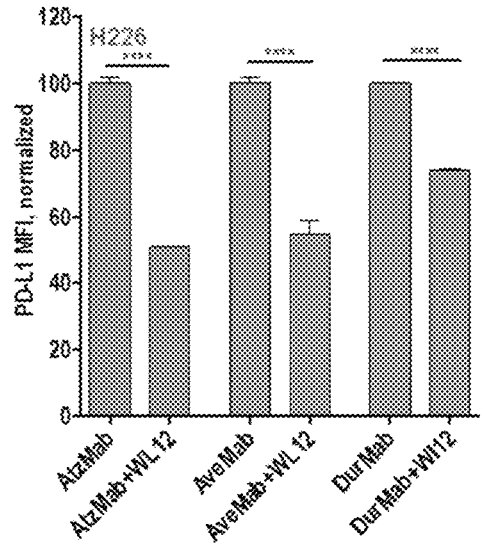
*Fig. 34D*

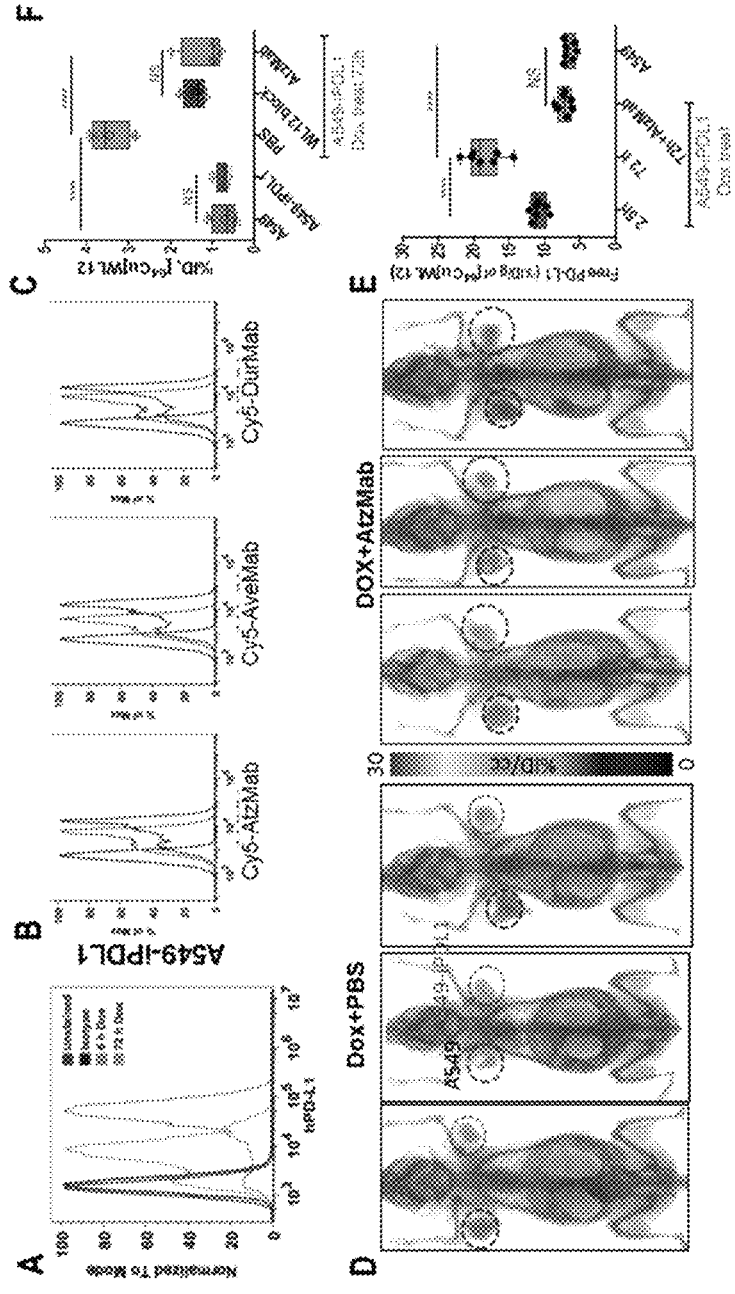

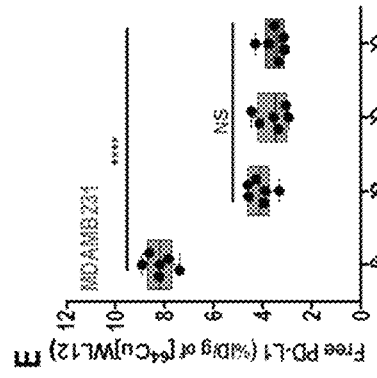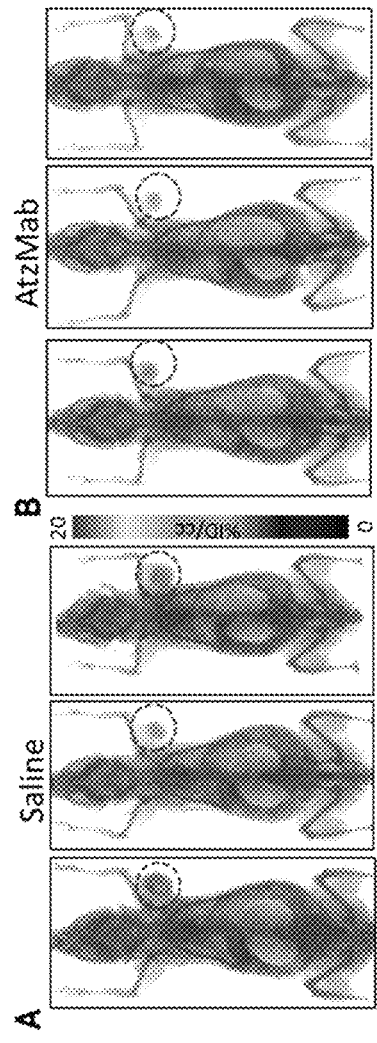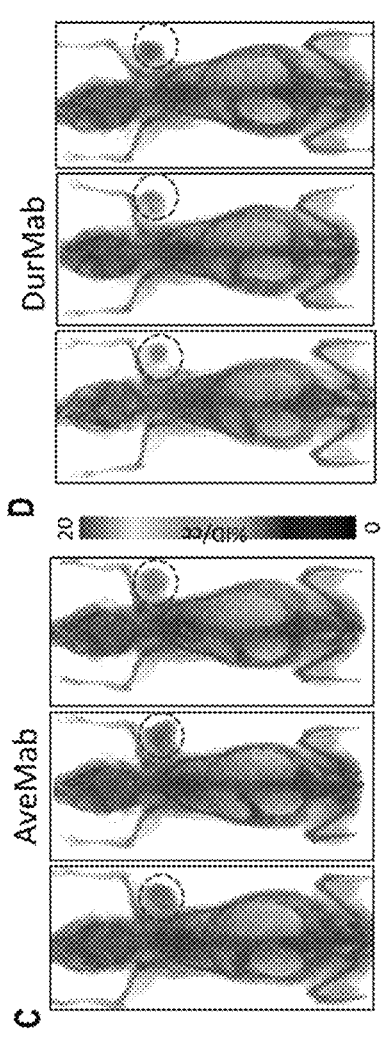

*Fig. 41A*
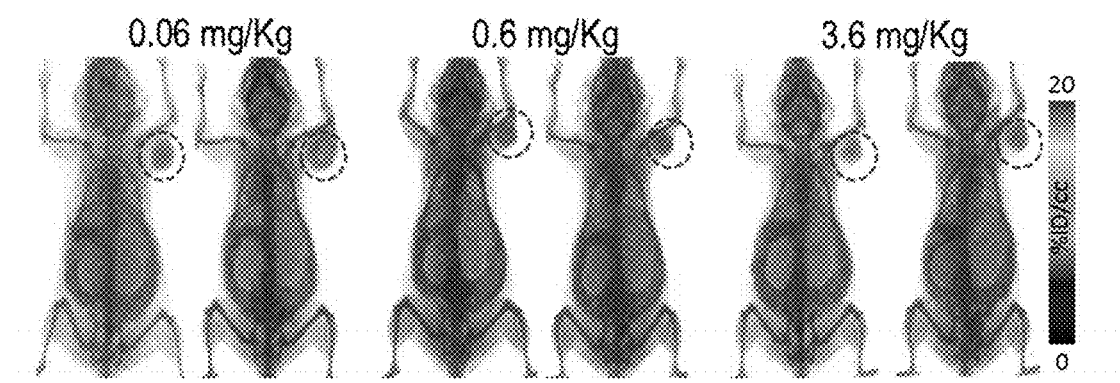
*Fig. 41B*    *Fig. 41C*
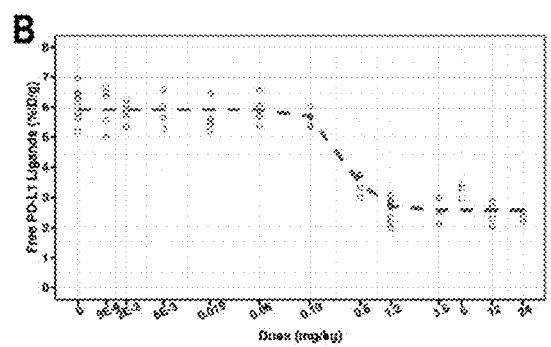
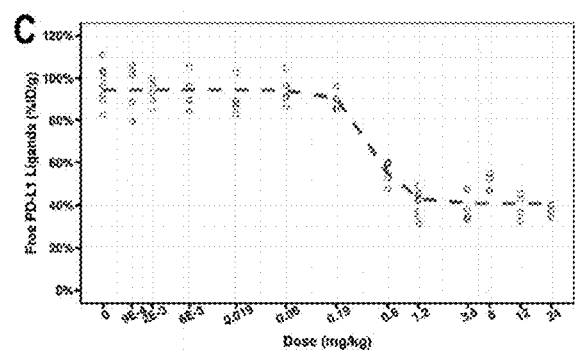
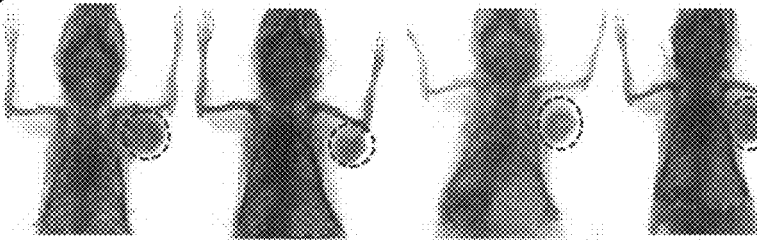
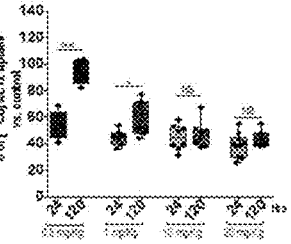
*Fig. 41D*    *Fig. 41E*

DK-A-221= Cyclo-(-Ac-Tyr-NMeAla-Asn-Pro-His-Glu-Hyp-Trp-Ser-Trp(Carboxymethyl)-NMeNle-NMeNle-Lys-Cys-)-Gly-NH2

TUMOR AND IMMUNE CELL IMAGING BASED ON PD-L1 EXPRESSION

CROSS-REFERENCE TO RELATED APPLICATIONS

This application claims the benefit of U.S. Provisional Application Nos. 62/438,575, filed Dec. 23, 2016, and 62/519,534, filed Jun. 14, 2017, which are incorporated herein by reference in their entirety.

FEDERALLY SPONSORED RESEARCH OR DEVELOPMENT

This invention was made with government support under CA166131 awarded by the National Institutes of Health. The government has certain rights in the invention.

BACKGROUND

Molecular imaging can report on the status of the tumor immune microenvironment and guide immunotherapeutic strategies to enhance the efficacy of immune modulation therapies. Imaging agents that can rapidly report on targets of immunomodulatory therapies are few.

Immunotherapy, which harnesses one's own immune system to kill cancer cells, is playing a central role in the treatment of various cancers (Topalian et al., 2016). In spite of the significantly improved therapeutic outcomes, many cancers do not respond to immunomodulatory therapies. Existing companion diagnostics that work through immunohistochemistry (IHC) provide only a snapshot of the dynamic tumor immune milieu and often do not accurately predict treatment response (Mansfield and Dong, 2016). Non-invasive imaging technologies can provide quantitative, real-time assessment of tumor biology and guide drug development (Willmann et al., 2008).

Positron emission tomography (PET), the most molecular and quantitative of translational imaging technologies, has been used for repetitive measurement of overall target expression in all the lesions in a given patient. Molecularly targeted PET tracers, such as [$^{18}$F]fluoroestradiol ($^{18}$F-FES) to detect estrogen receptor (ER) positive breast cancer, can predict response to therapy and progression-free survival (Peterson et al., 2008, and Linden et al., 2006). PET tracers, as well as imaging agents for other imaging methodologies including, but not limited to, magnetic resonance imaging (MRI), fluorescence imaging, near infrared (NIR) imaging, photoacoustic imaging, and Raman imaging, which can provide rapid and real-time assessment of target expression relevant to immunomodulatory therapies could significantly benefit ongoing clinical trials.

The programmed death ligand 1 (PD-L1) is an immune checkpoint protein over-expressed in several cancers and contributes to tumor immune suppression. Tumor PD-L1 expression is indicative of tumor response to PD-1 and PD-L1 targeted therapies. It has been shown that radiolabeled anti-PD-L1 antibodies can be used to assess PD-L1 expression non-invasively in human tumor xenografts and in syngeneic tumor models (Heskamp et al., 2015; Maute et al., 2015; Chatterjee et al., 2016; Deng et al., 2016; Hettich et al., 2016; Josefsson et al., 2016). Although radiolabeled antibody conjugates are increasingly used for imaging tumor-specific proteins, longer clearance times, extending up to days, are required for enhanced contrast and lesion detection (Pandit-Taskar et al., 2015; Oosting et al., 2016).

SUMMARY

In some aspects, the presently disclosed subject matter provides an imaging agent comprising a conjugate of a peptide having a binding specificity for programmed death ligand 1 (PD-L1) and a reporting moiety, and optionally a linker, wherein the linker, when present connects the peptide and the reporting moiety, and when the linker is absent, the reporting moiety is attached directly to the peptide through a primary amine of an amino acid of the peptide. In other aspects, the reporting moiety is directly incorporated into the peptide, for example, wherein the reporting moiety comprises a radiolabeled amino acid of the peptide, such as radiolabeled iodotyrosine or fluorotyrosine.

In particular aspects, the peptide having a binding specificity for PD-L1 interacts with amino acids Y56, E58, A113, M115, and Y123 of PD-L1.

In certain aspects, the peptide is WL12 and the imaging agent is a compound selected from the group consisting of formula (I), formula (II), and formula (III):

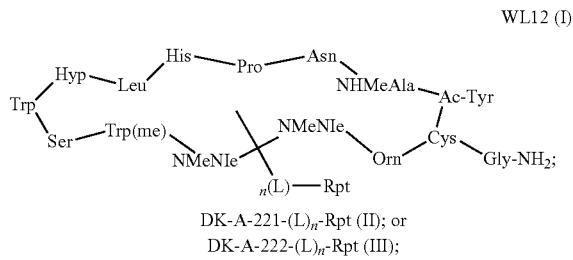

DK-A-221-(L)$_n$-Rpt (II); or
DK-A-222-(L)$_n$-Rpt (III);

wherein: n is an integer selected from the group consisting of 0 and 1; L is a linker; and Rpt is a reporting moiety; and wherein the reporting moiety or linker, when present, is attached to a primary amine group of an amino acid of the peptide comprising the imaging agent of formula (I), formula (II), or formula (III).

In particular aspects, the compound of formula (I) is WL12 DOTA:

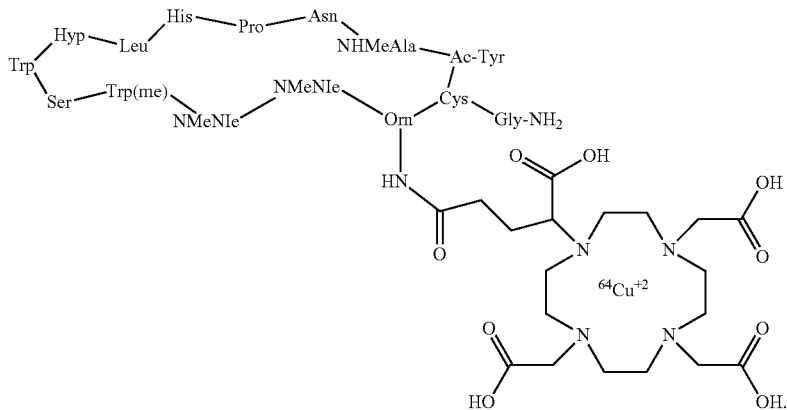

In other aspects, the presently disclosed subject matter provides an imaging method for detecting Programmed Death Ligand 1 (PD-L1), the method comprising: (a) providing an effective amount of an imaging agent comprising a conjugate of a peptide having a binding specificity for programmed death ligand 1 (PD-L1) and a reporting moiety, and optionally a linker, wherein the linker, when present connects the peptide and the reporting moiety, and when the linker is absent, the reporting moiety is attached directly to the peptide through a primary amine of an amino acid of the peptide; (b) contacting one or more cells or tissues with the imaging agent; and (c) making an image to detect PD-L1. In particular aspects, the imaging agent is a compound of formula (I) or a peptide that interacts with Y56, E58, A113, M115 and Y123 of PD-L1.

In certain aspects, the presently disclosed imaging agents can be used to detect diseases and disorders, such as cancer, infection, and inflammation, in a subject.

In yet more aspects, the presently disclosed subject matter provides a kit for detecting Programmed Death Ligand 1 (PD-L1), the kit comprising an imaging agent comprising a conjugate of a peptide having a binding specificity for programmed death ligand 1 (PD-L1) and a reporting moiety, and optionally a linker, wherein the linker, when present connects the peptide and the reporting moiety, and when the linker is absent, the reporting moiety is attached directly to the peptide through a primary amine of an amino acid of the peptide.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
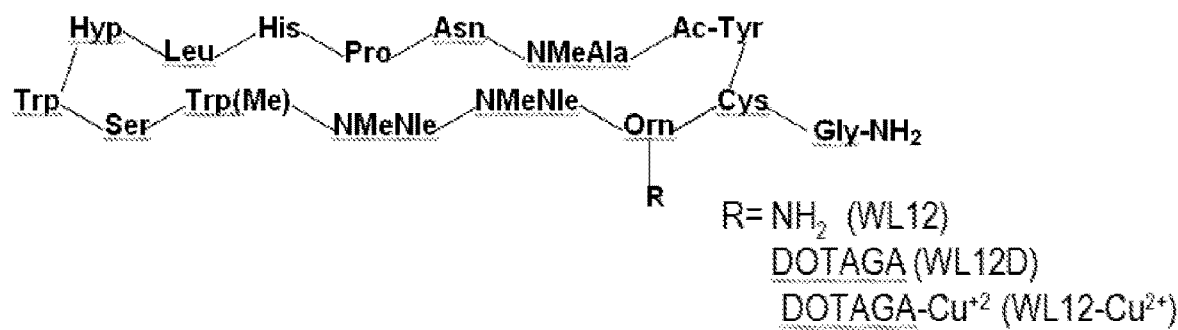
Figure 1B:
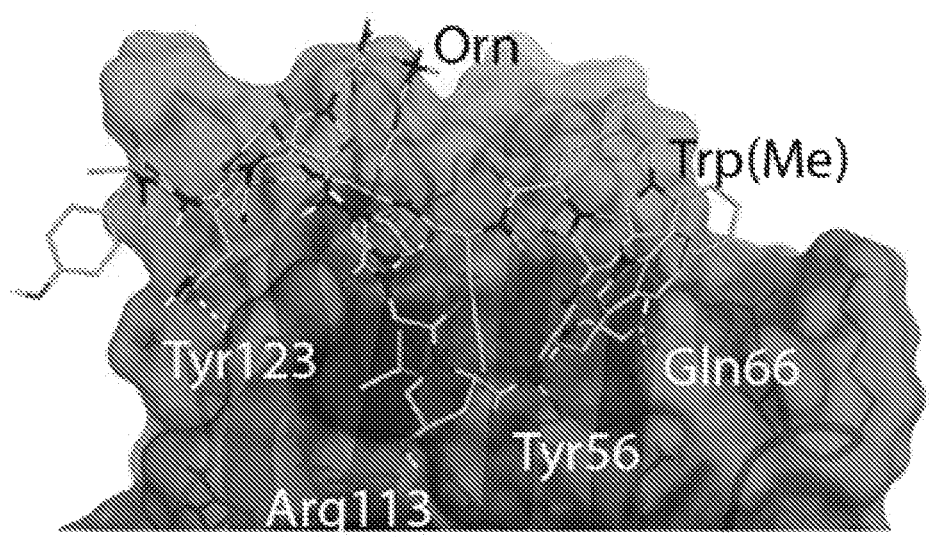
Figure 1C:
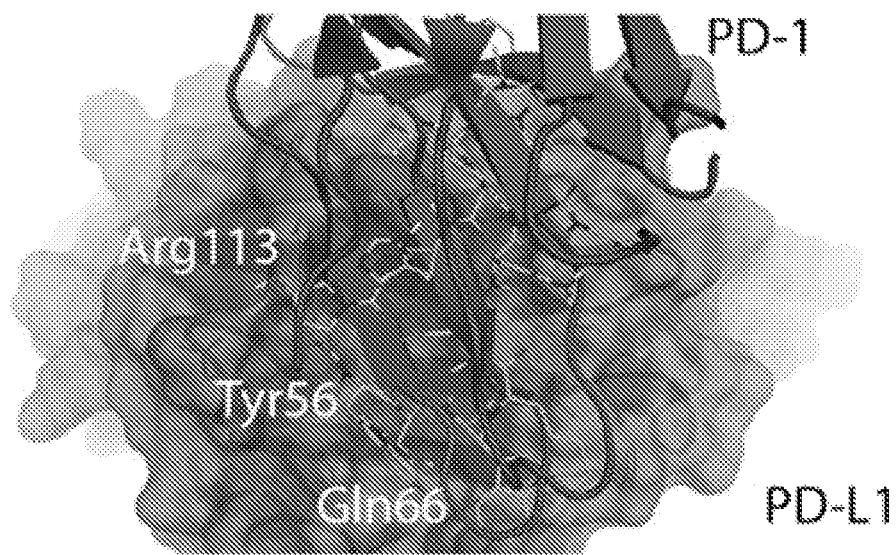
Figure 2:
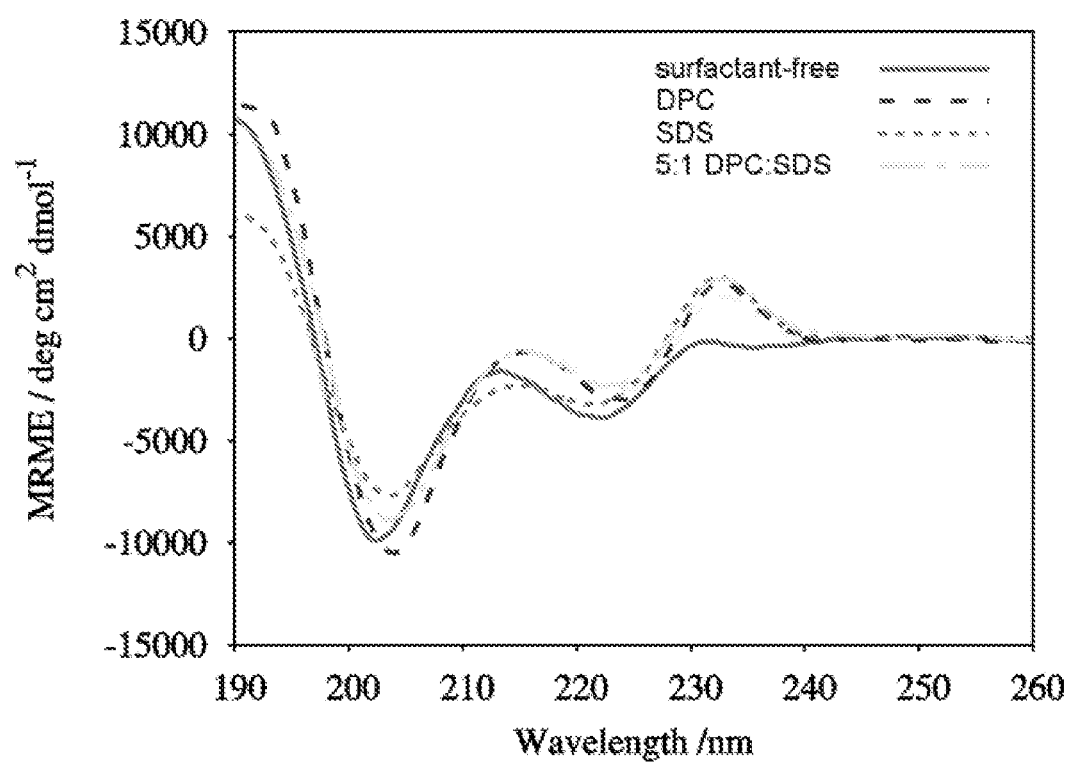
Figure 3:
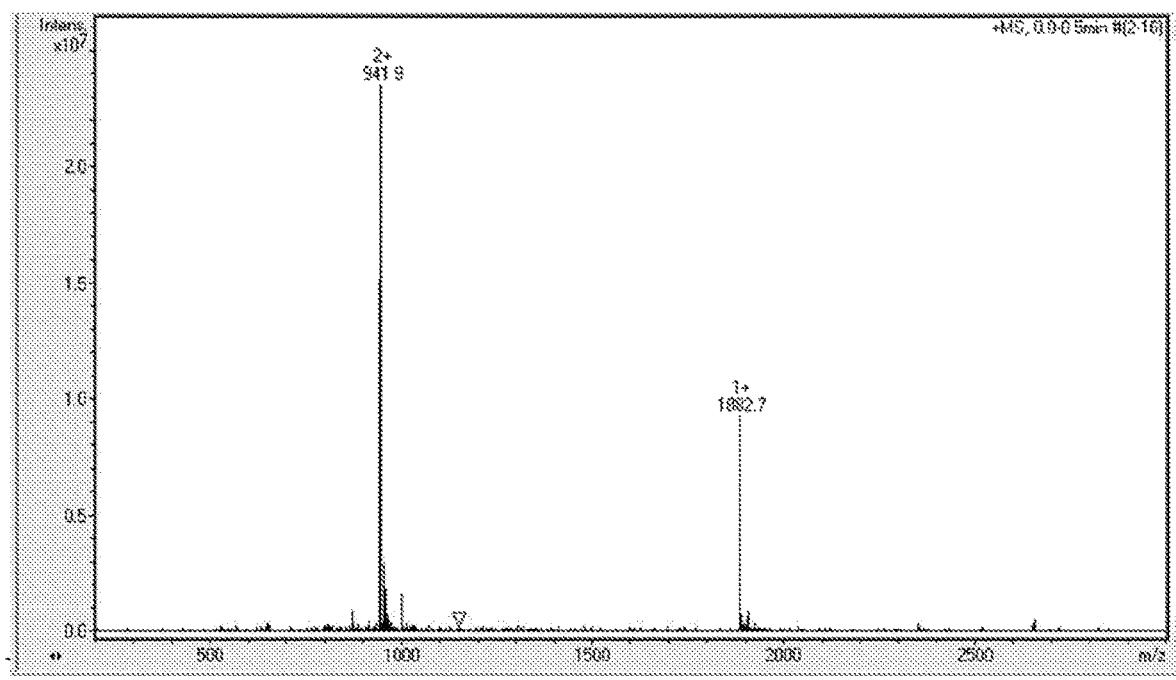
Figure 4:
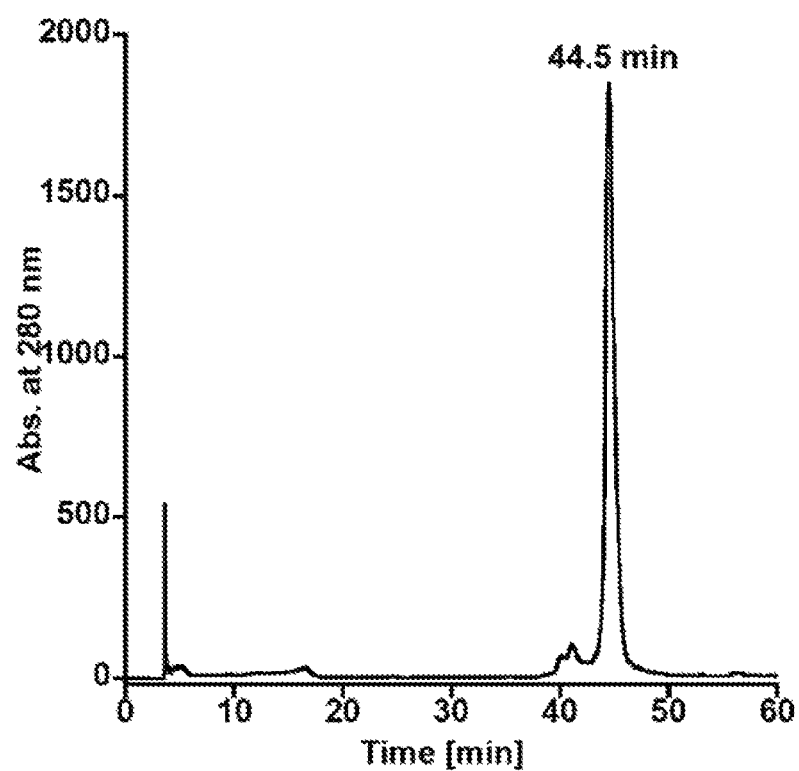
Figure 5:
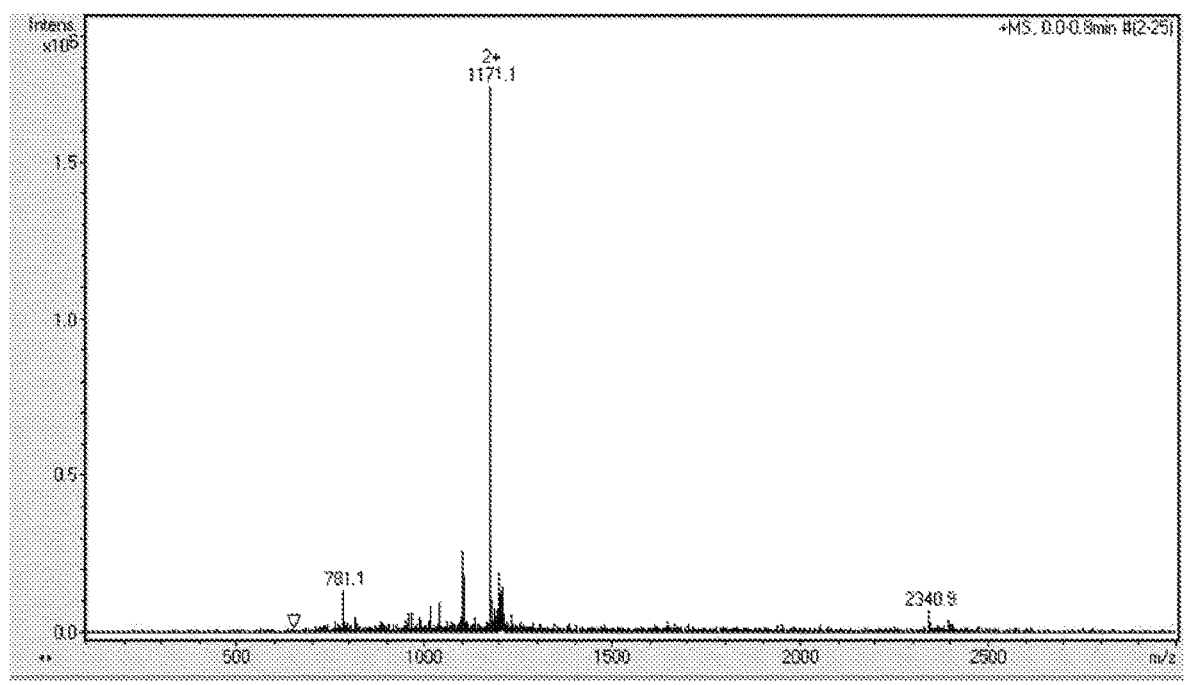
Figure 6:
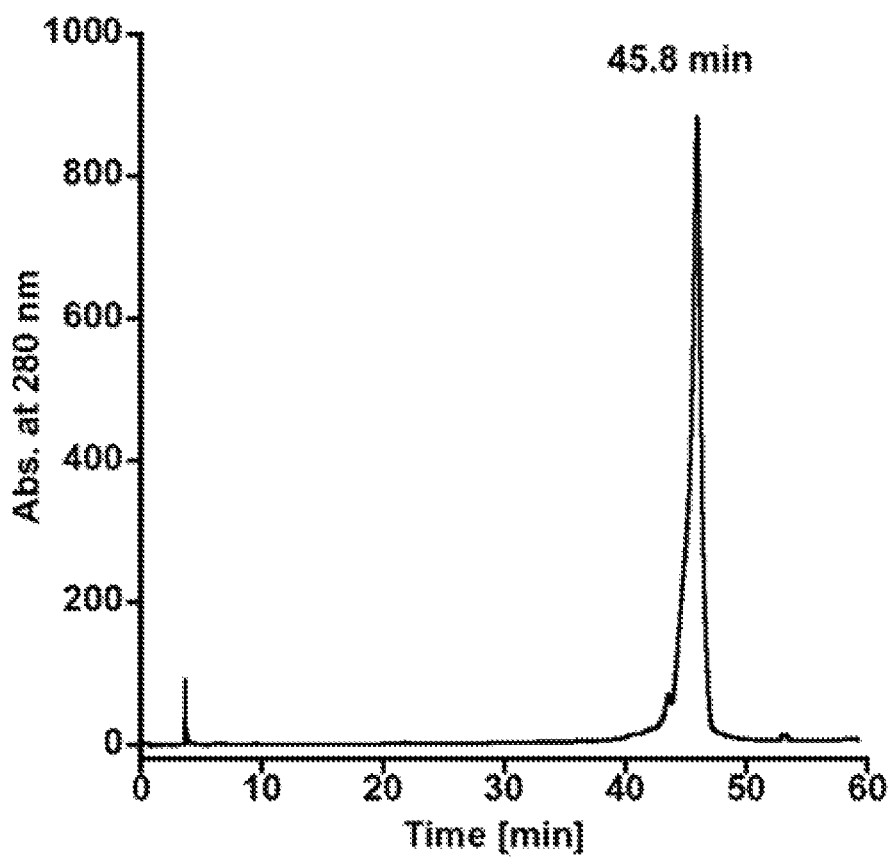
Figure 7:
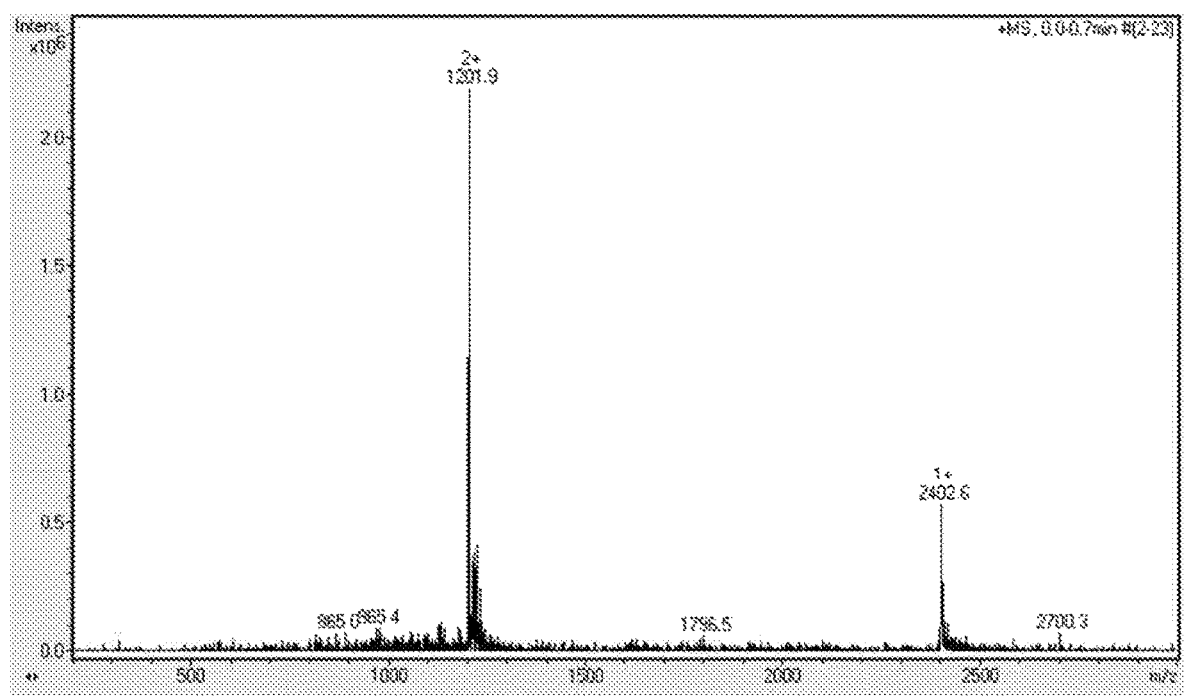
Figure 8A:
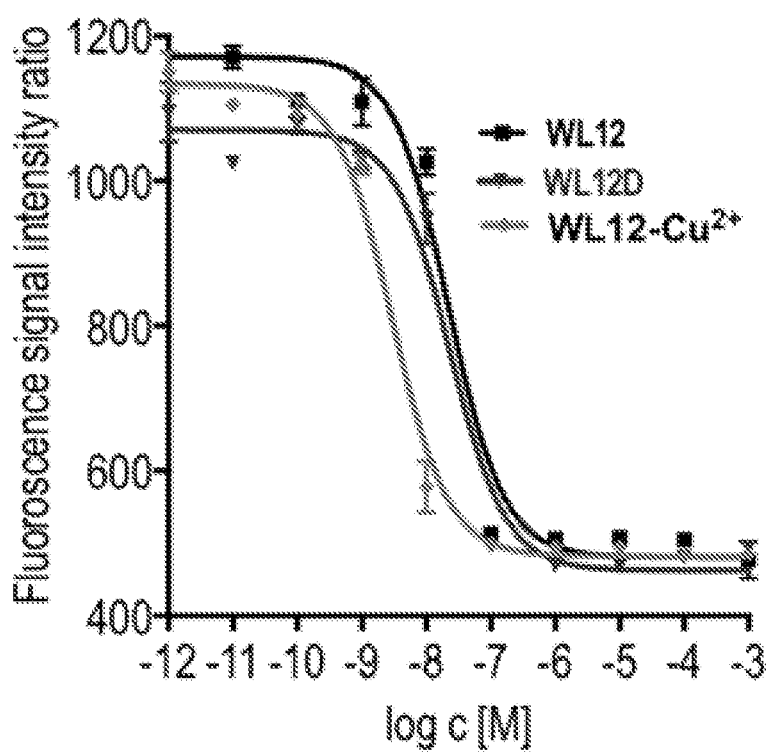
Figure 8B:
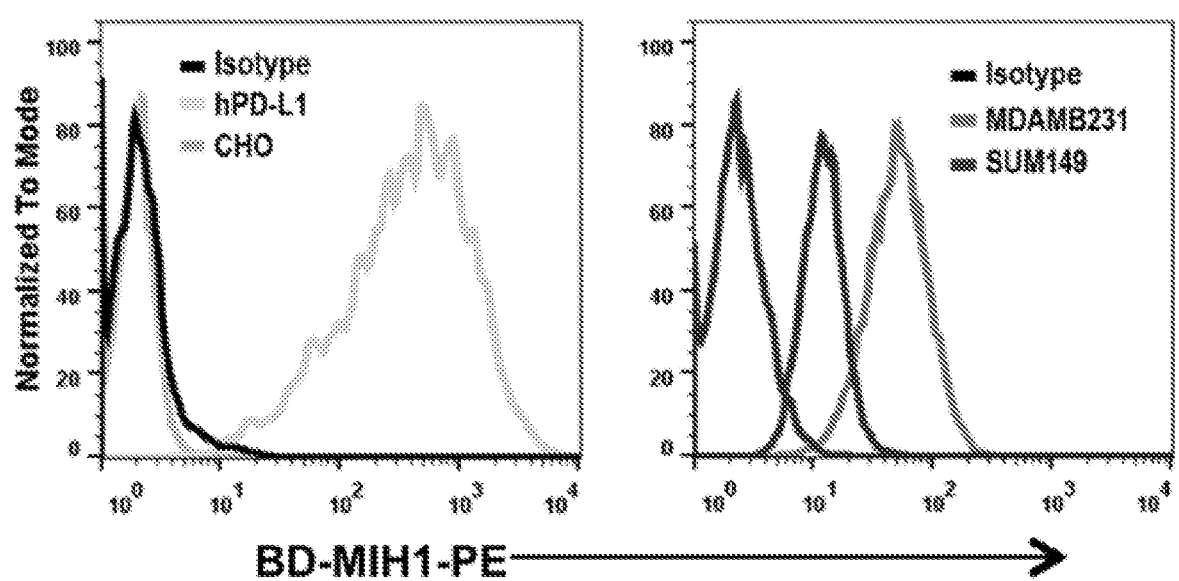
Figure 8C:
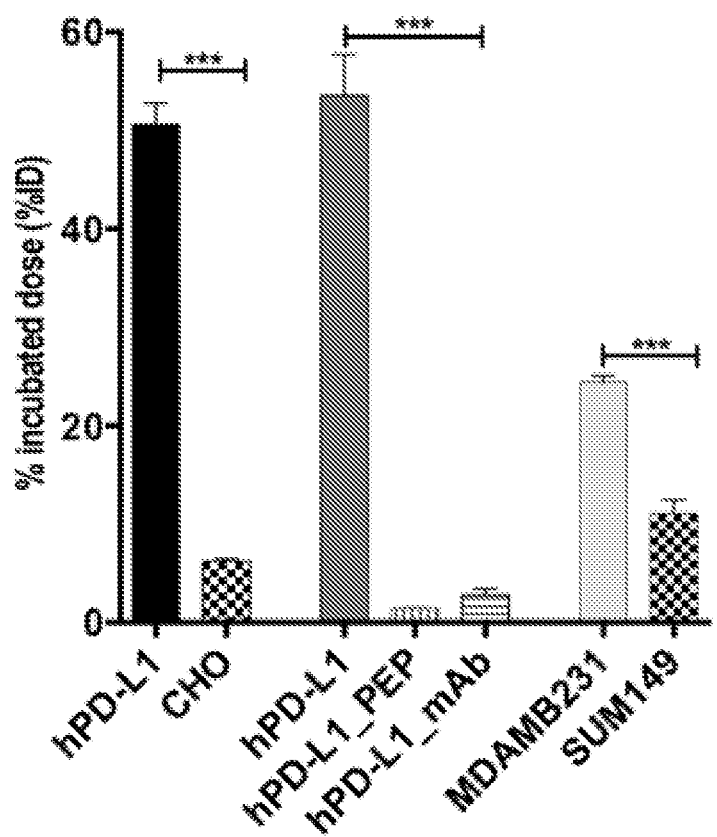
Figure 9:
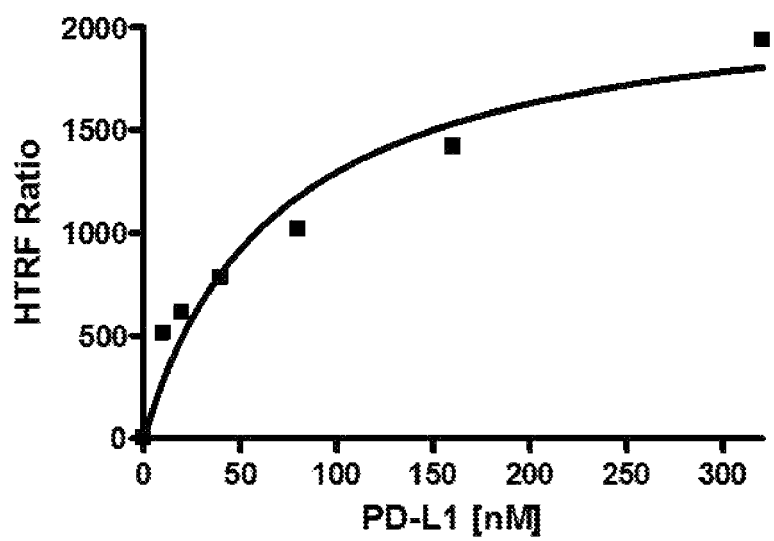
Figure 10:
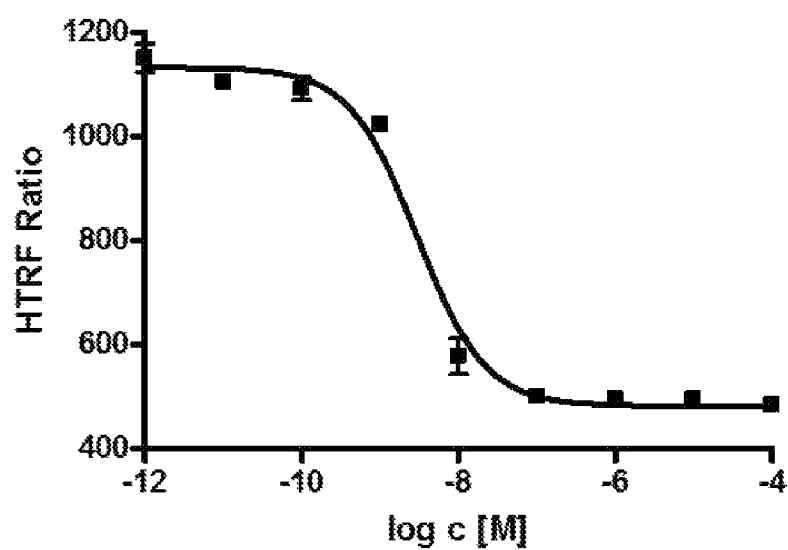
Figure 11:
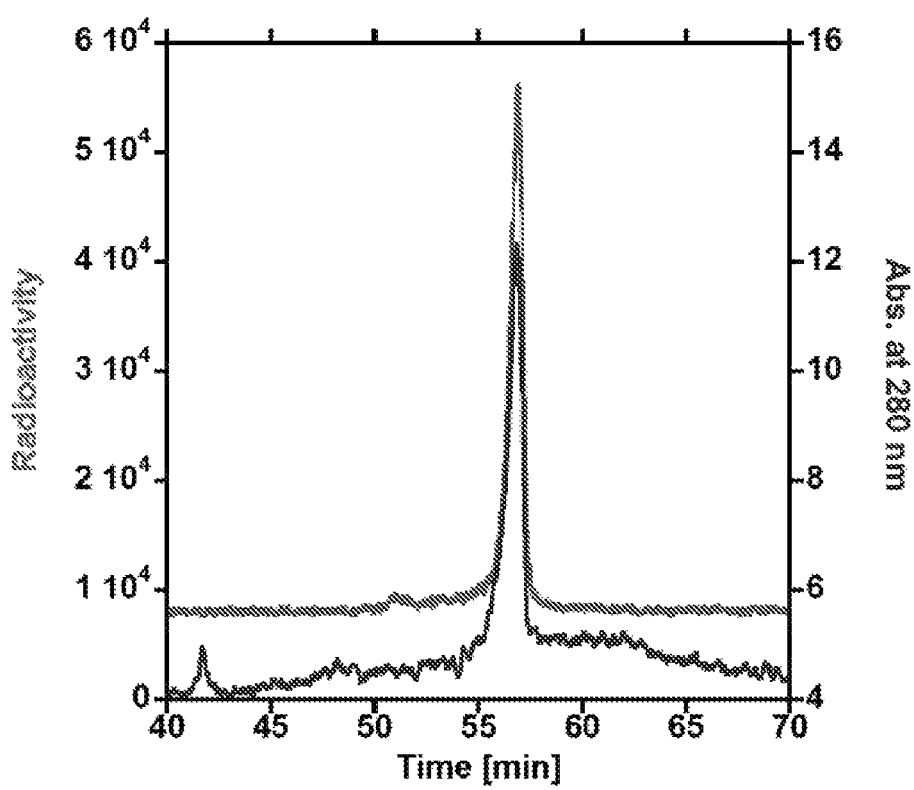
Figure 12:
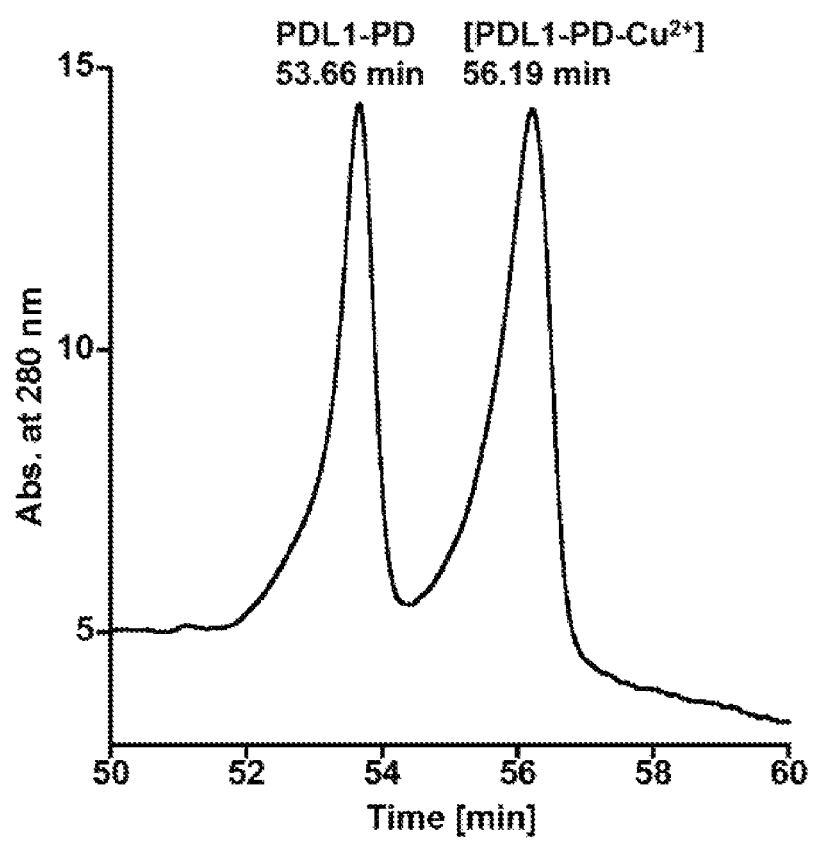
Figure 13:
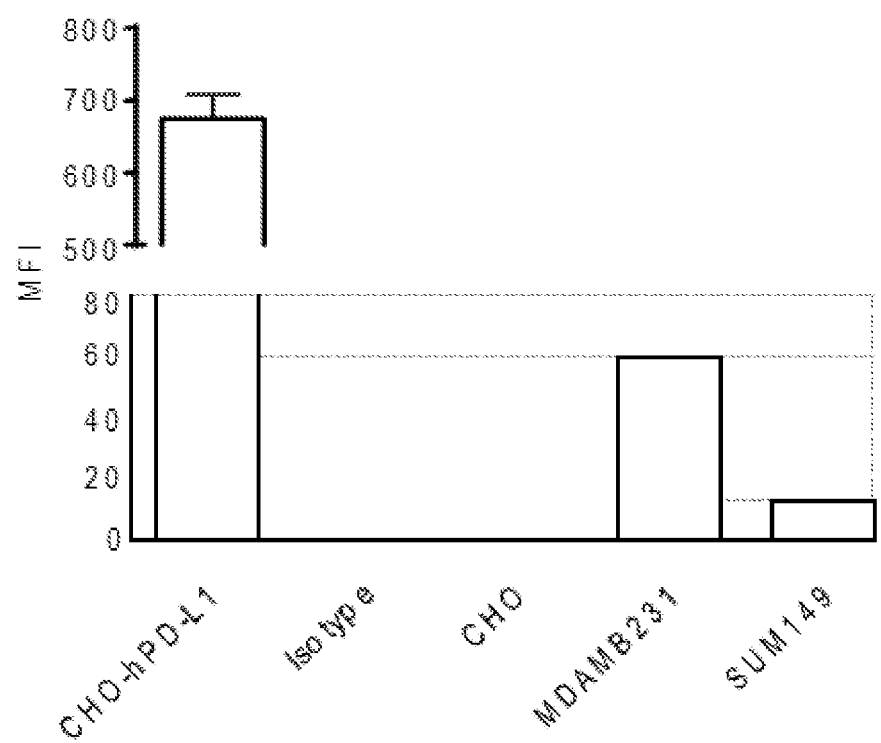
Figure 14:
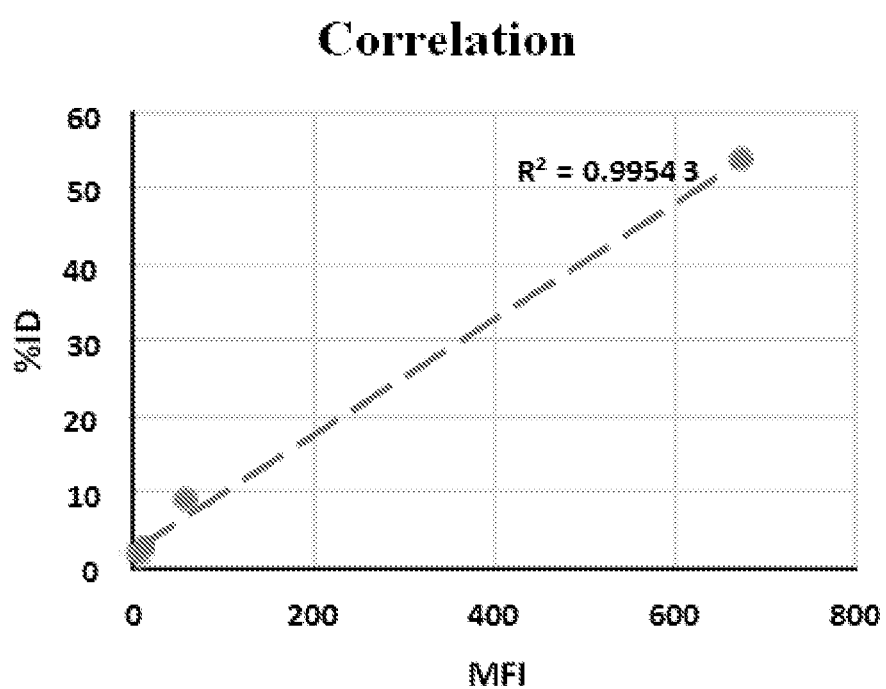
Figure 15A:
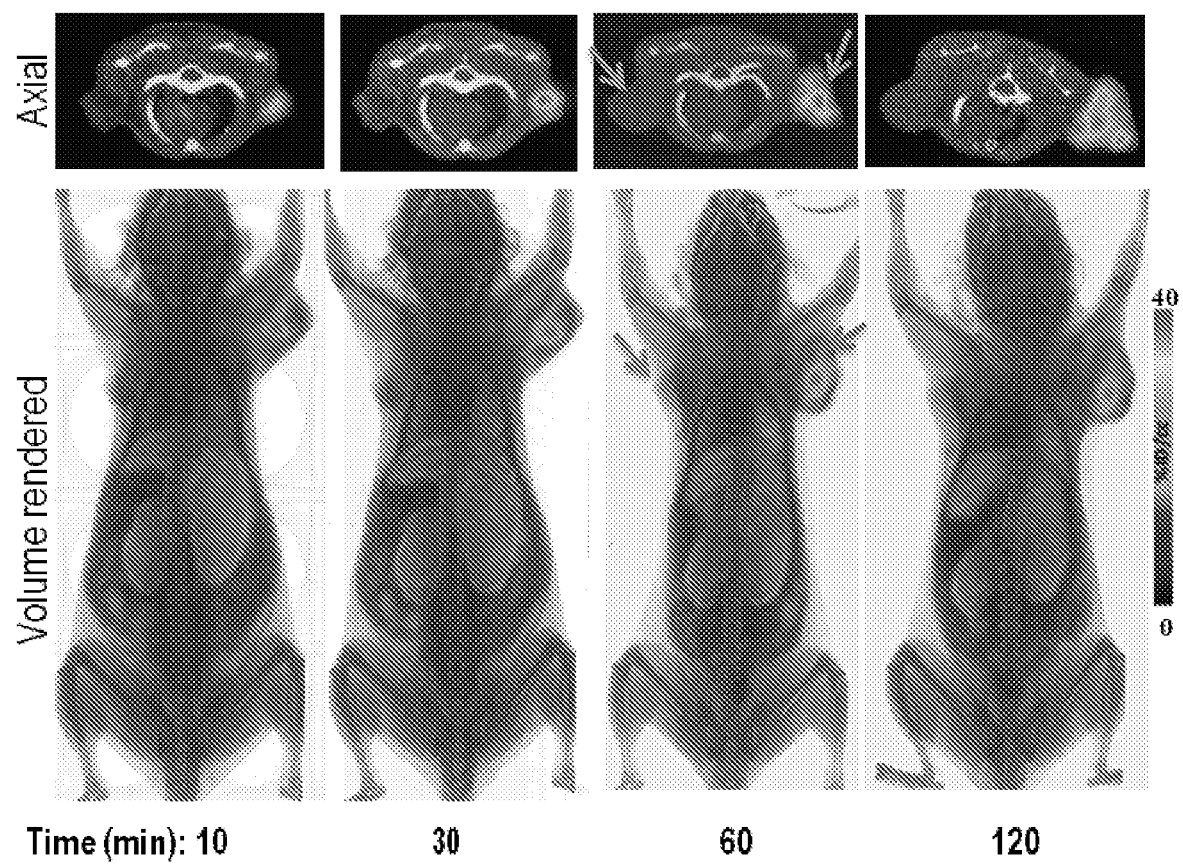
Figure 16:
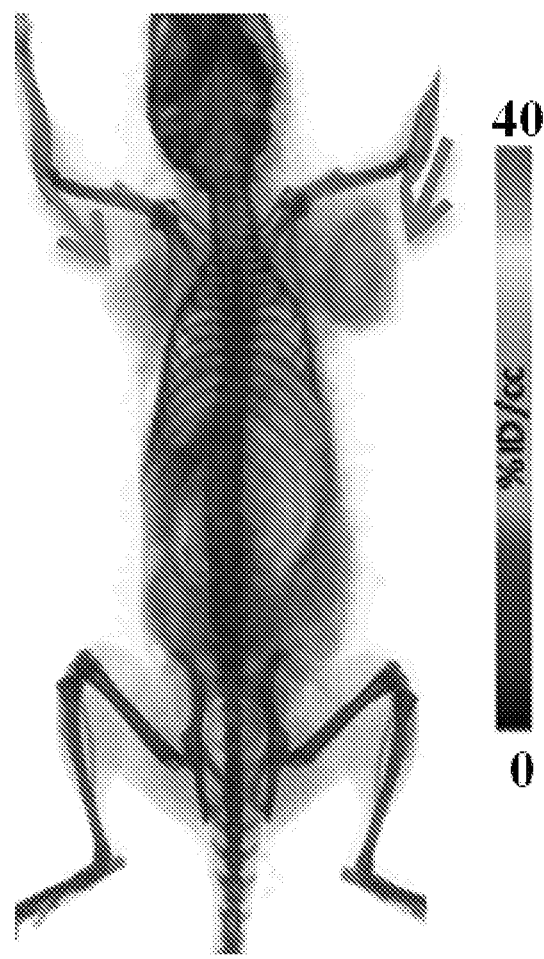
Figure 17:
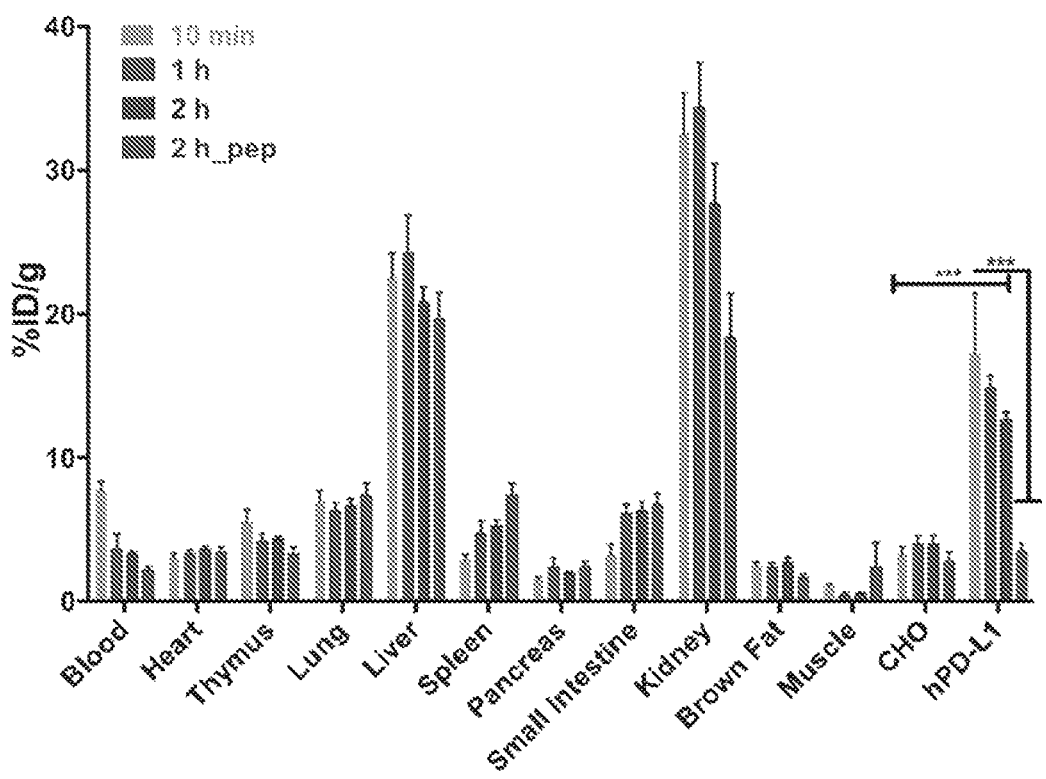
Figure 18A:
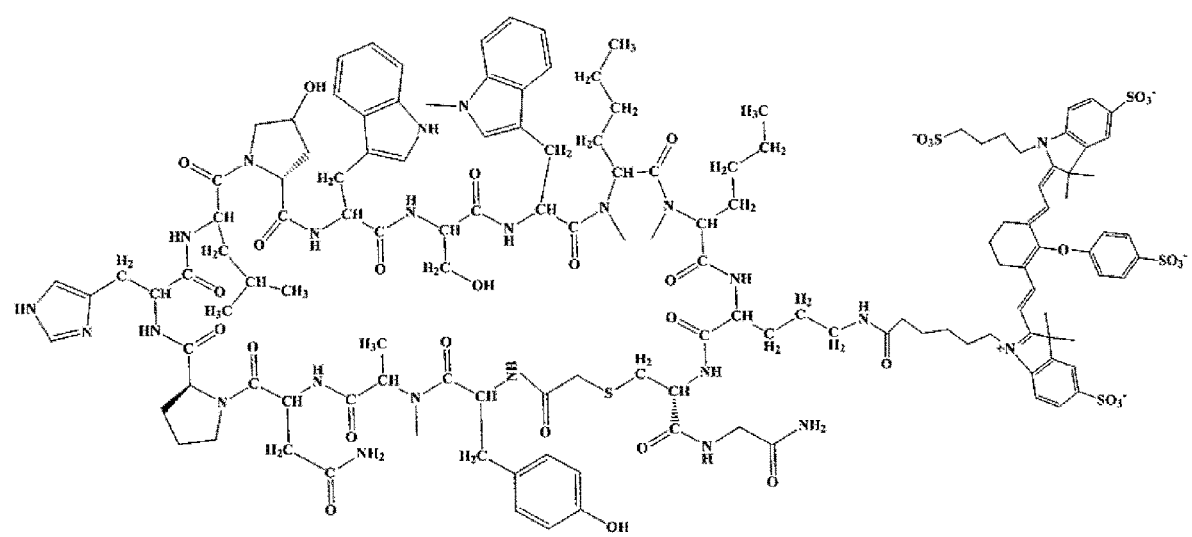
Figure 18B:
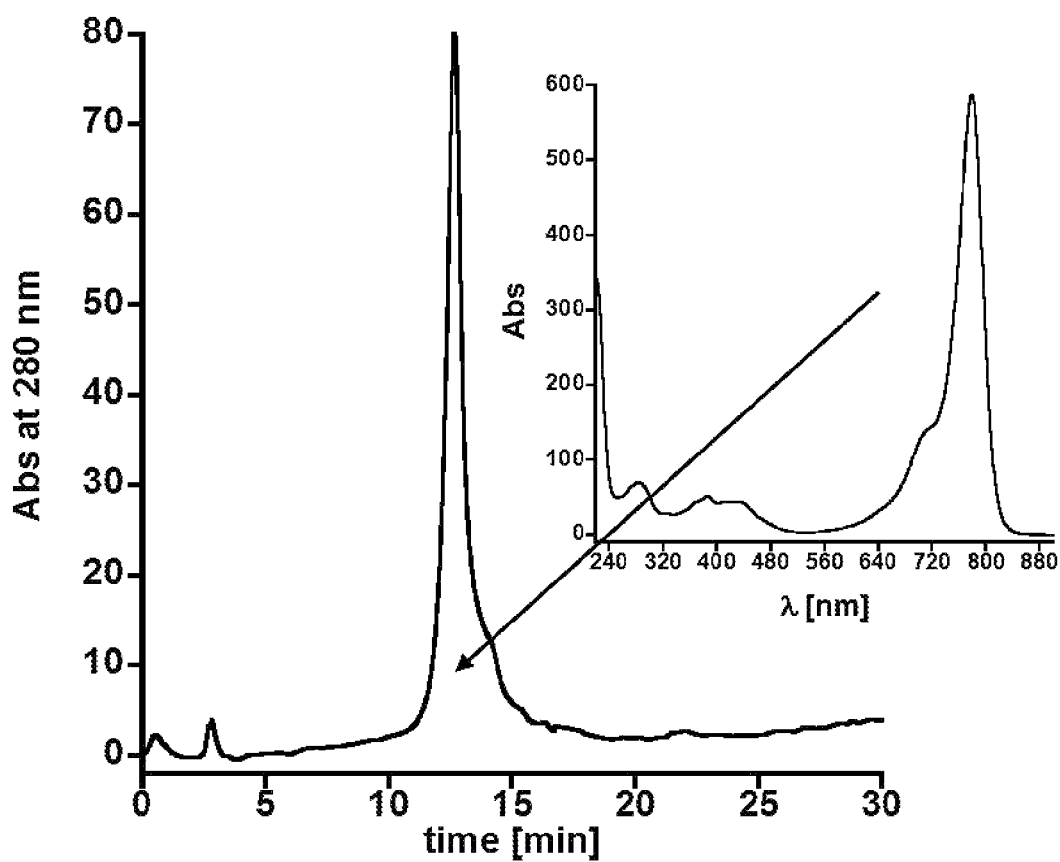
Figure 18C:
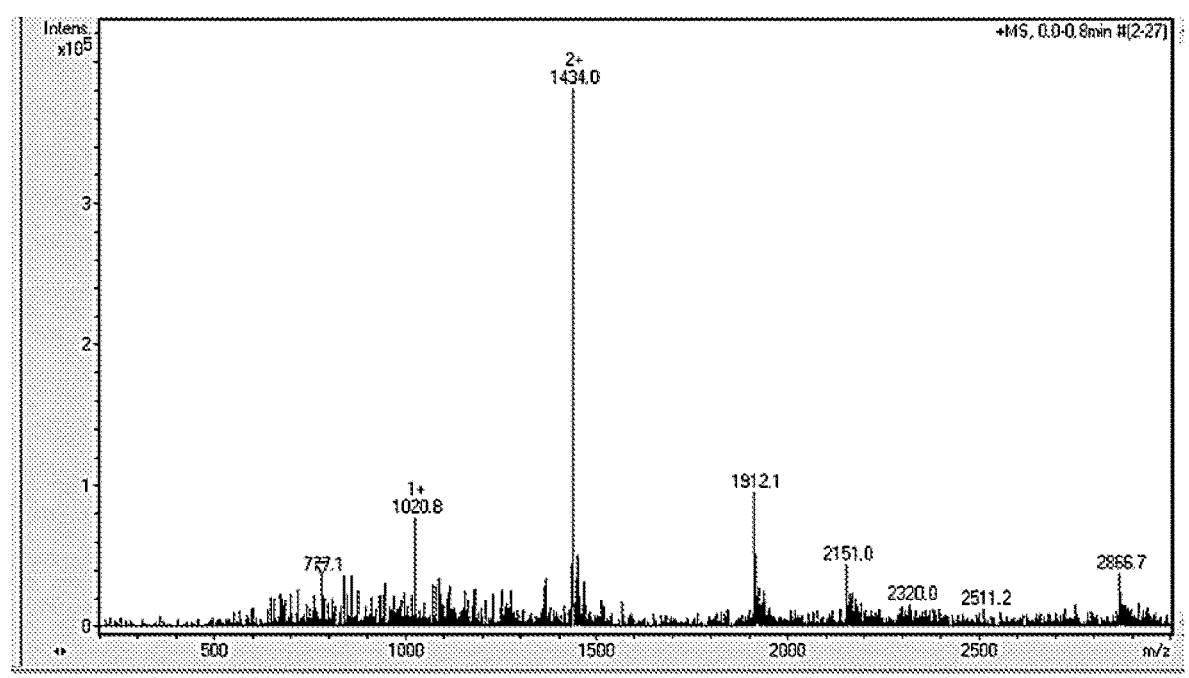
Figure 19A:
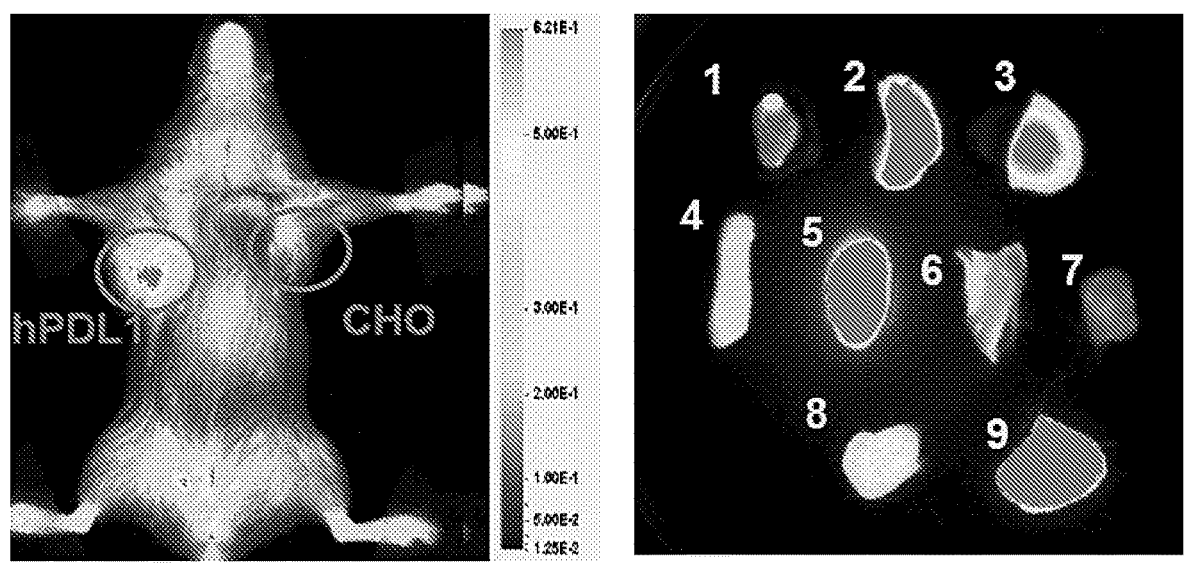
Figure 19B:
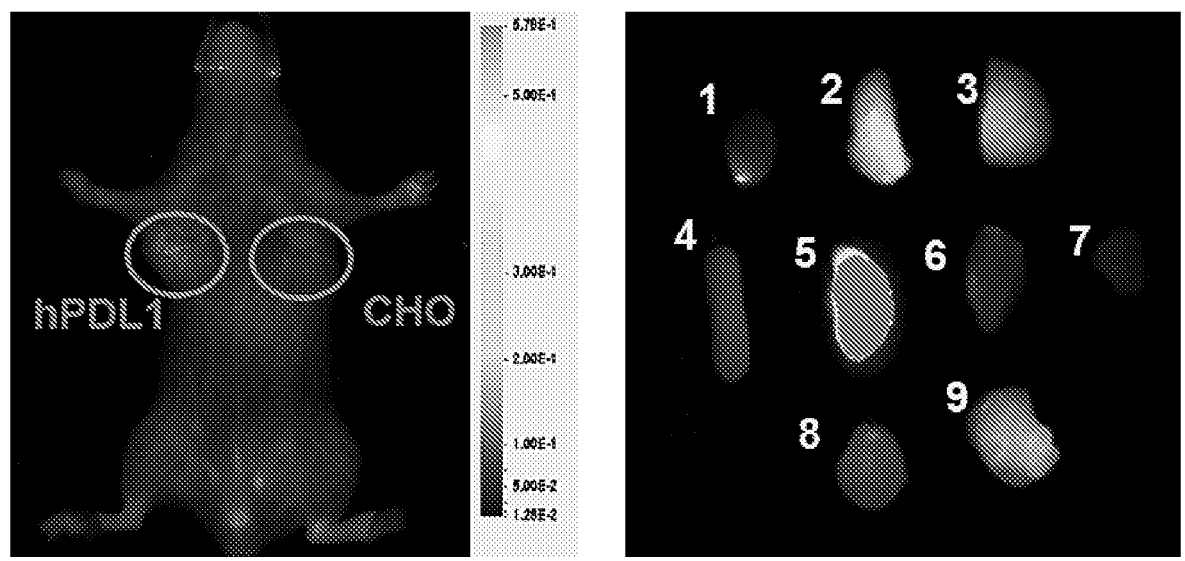
Figure 19C:
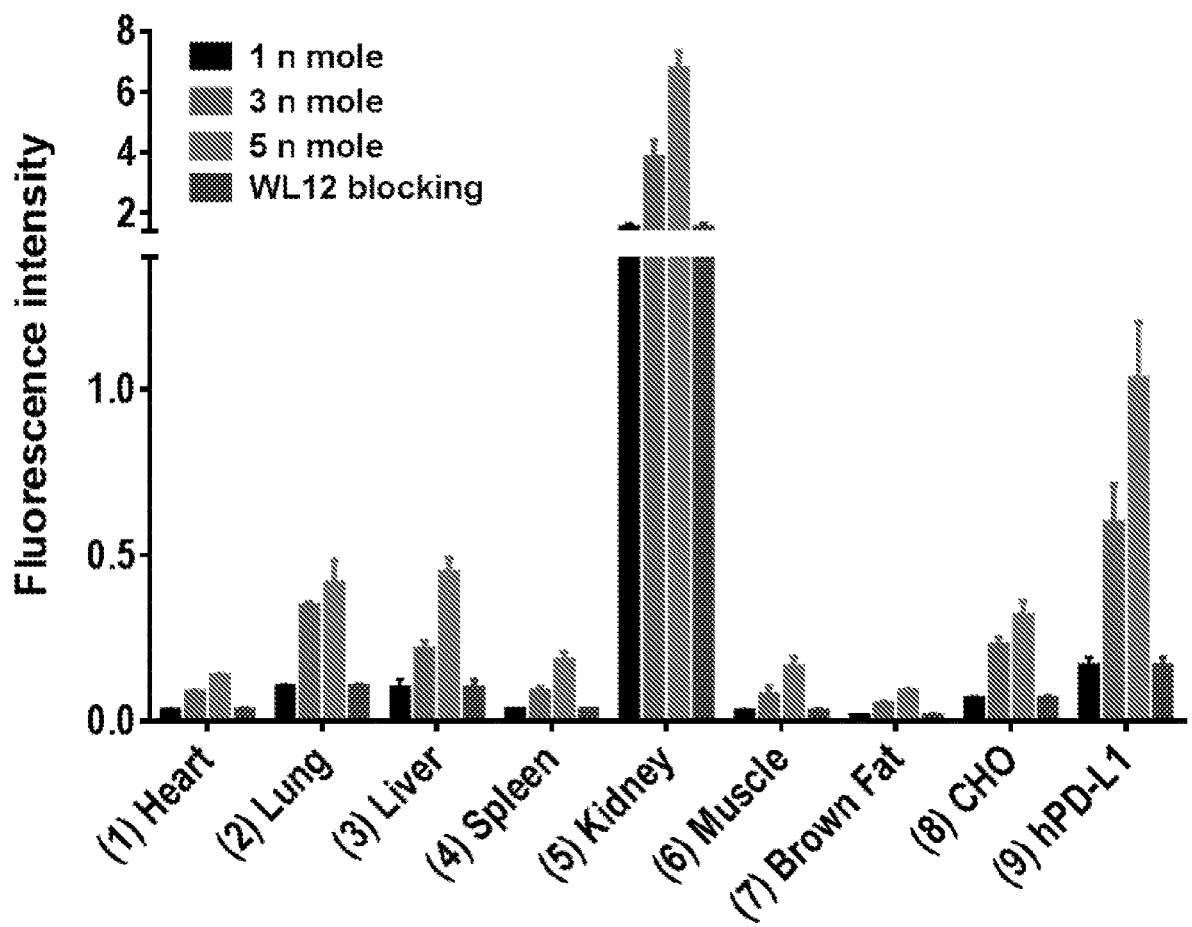
Figure 20:
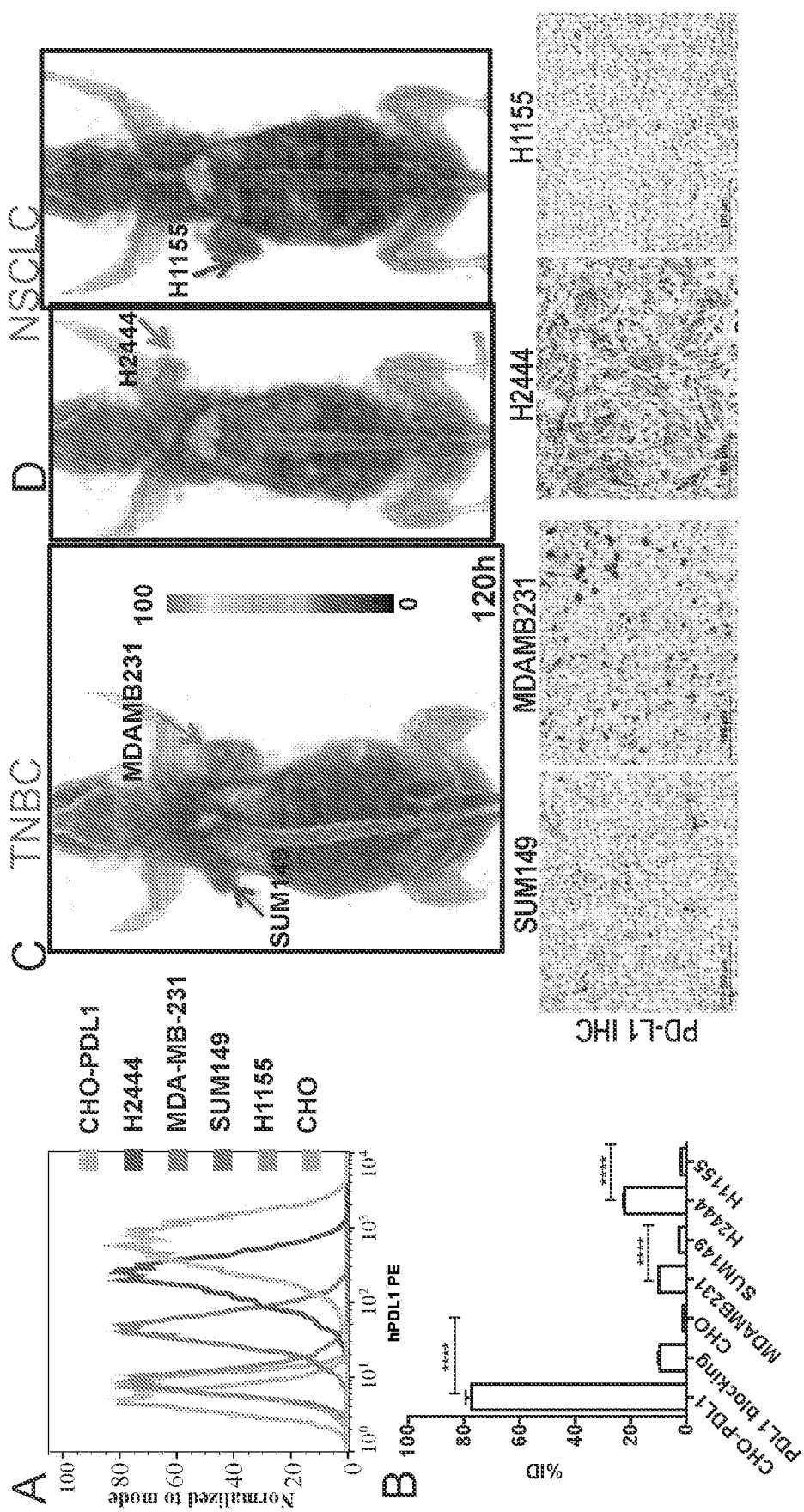
Figure 22:
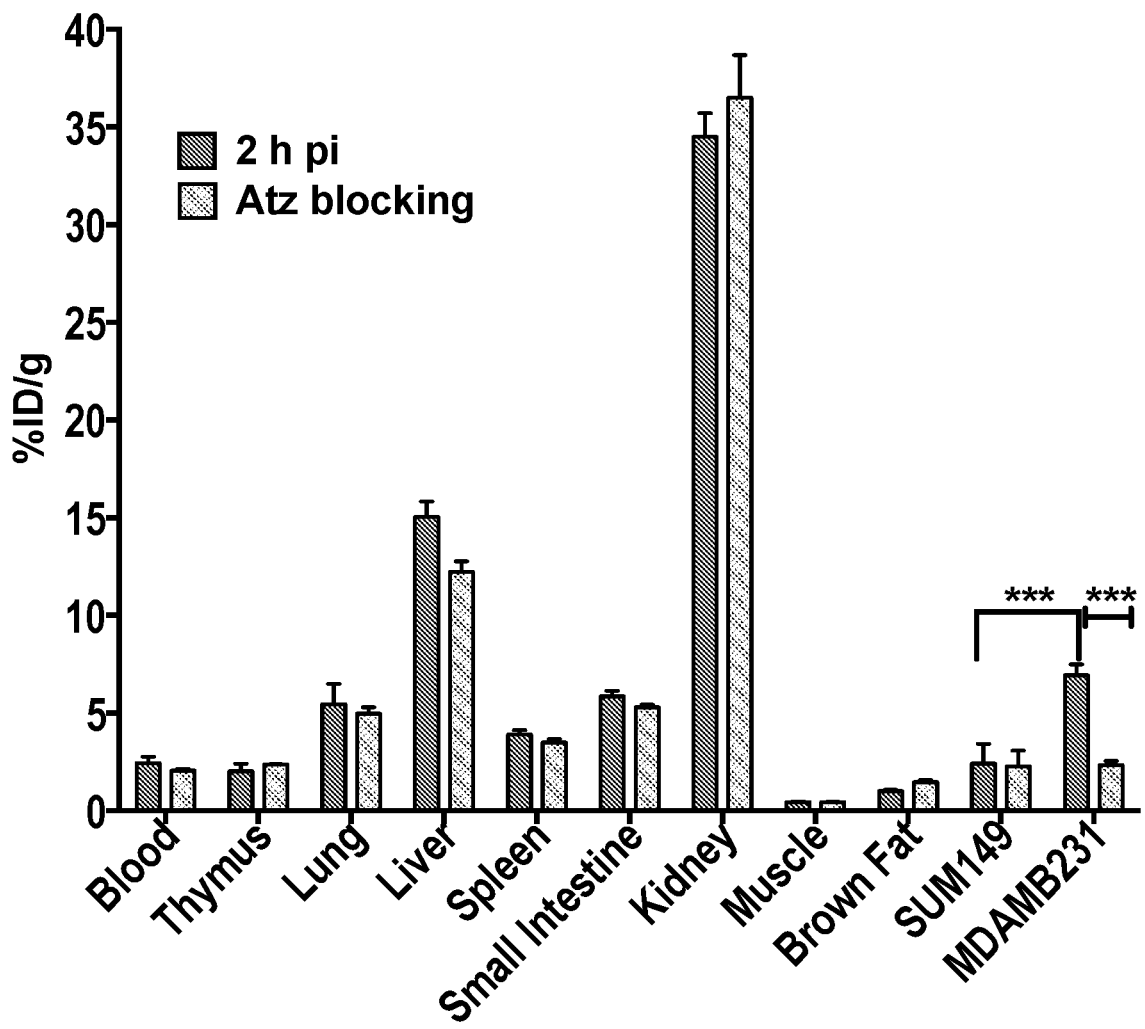
Figure 23A:
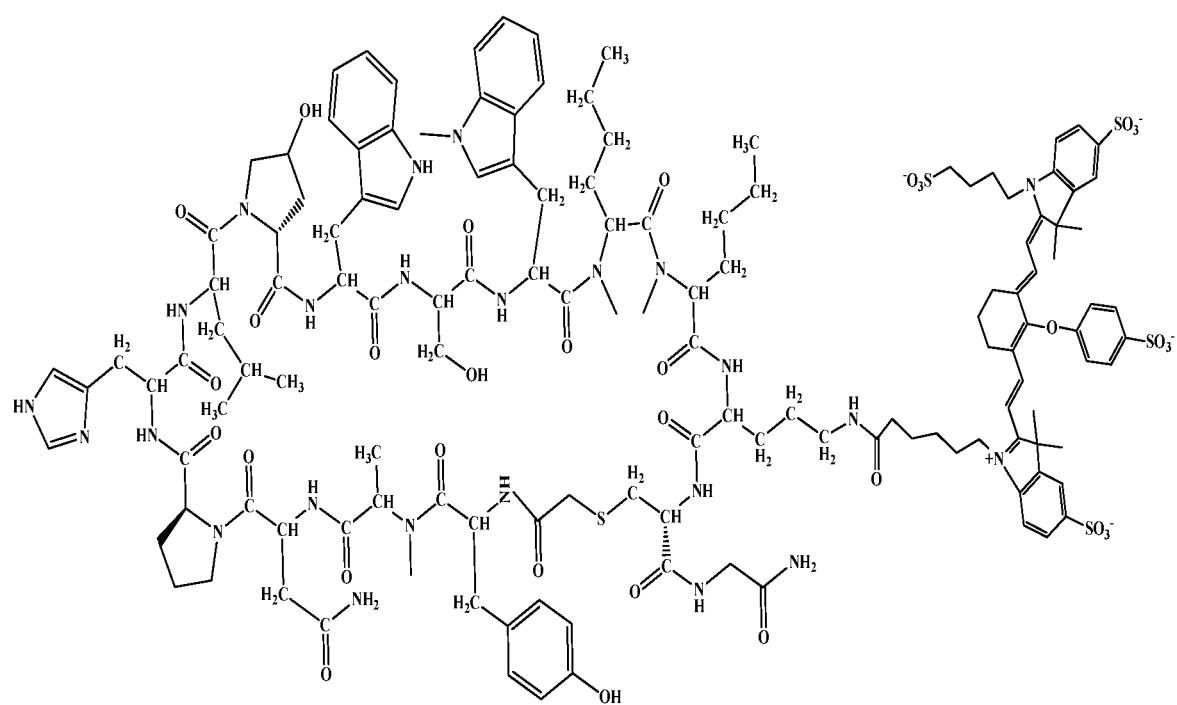
Figure 23B:
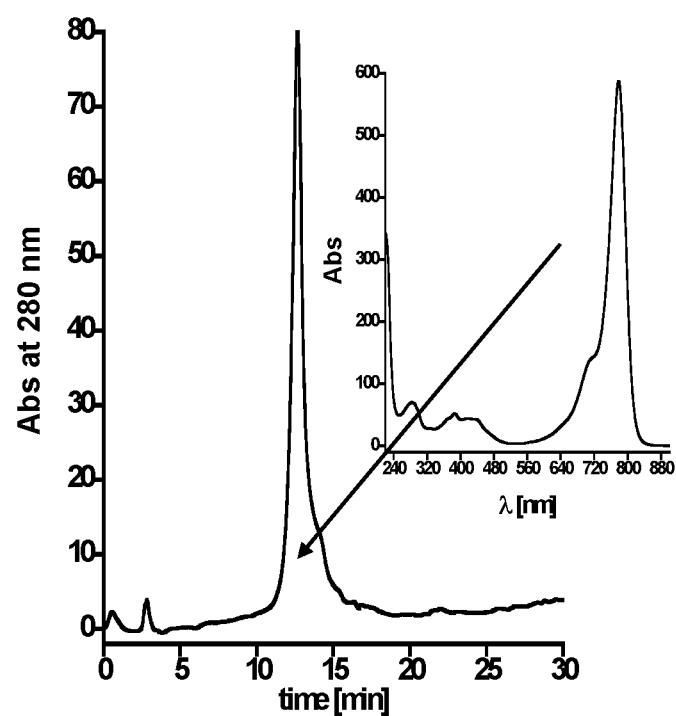
Figure 23C:
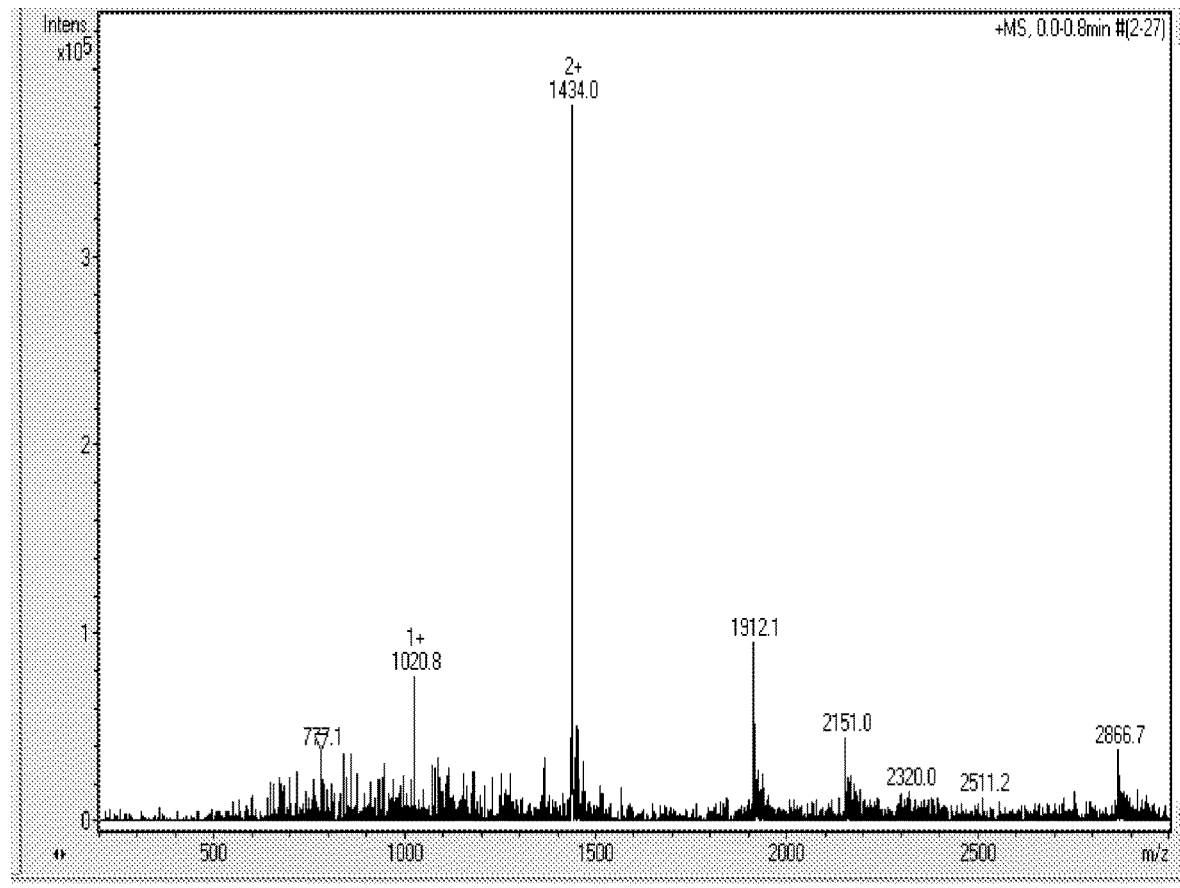
Figures 24A, 24B:
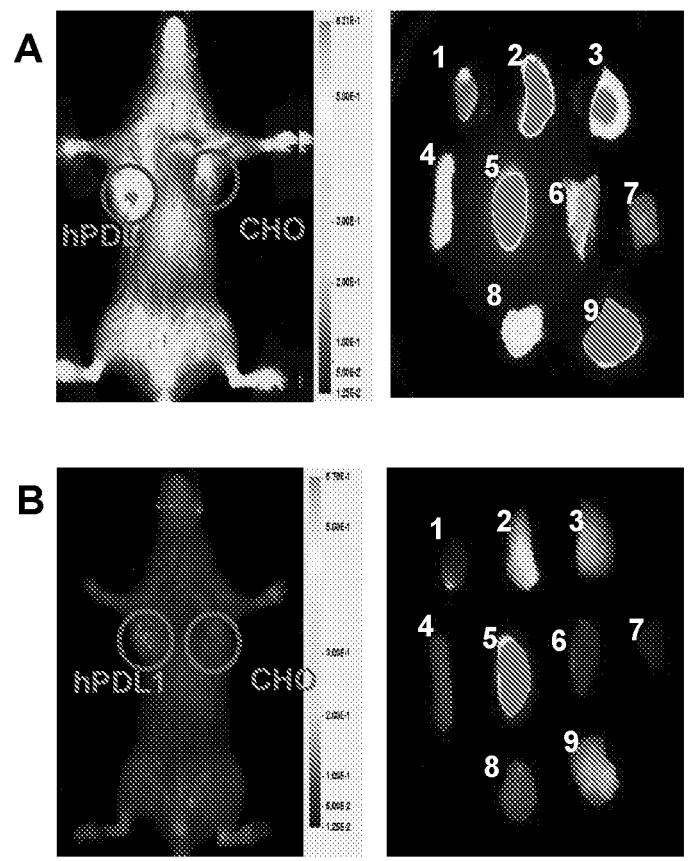
Figure 24C:
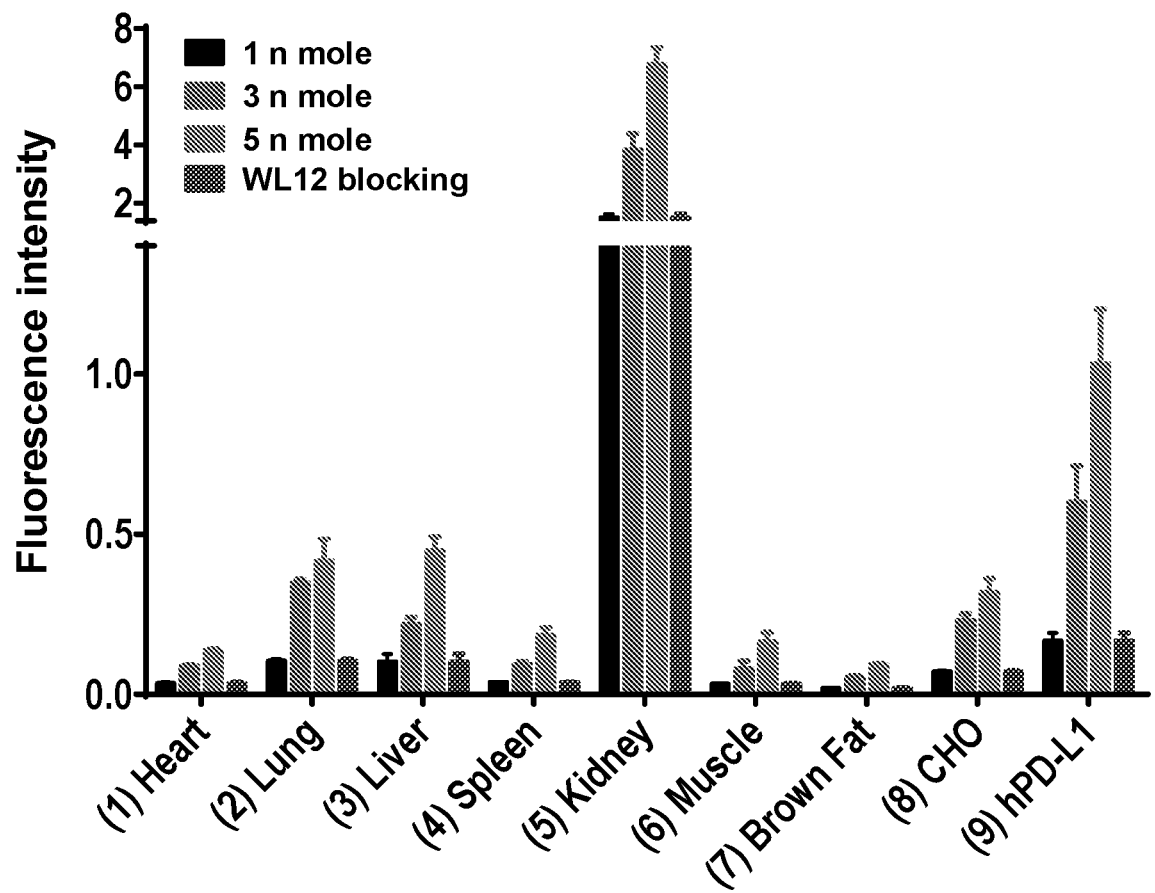
Figure 25A:
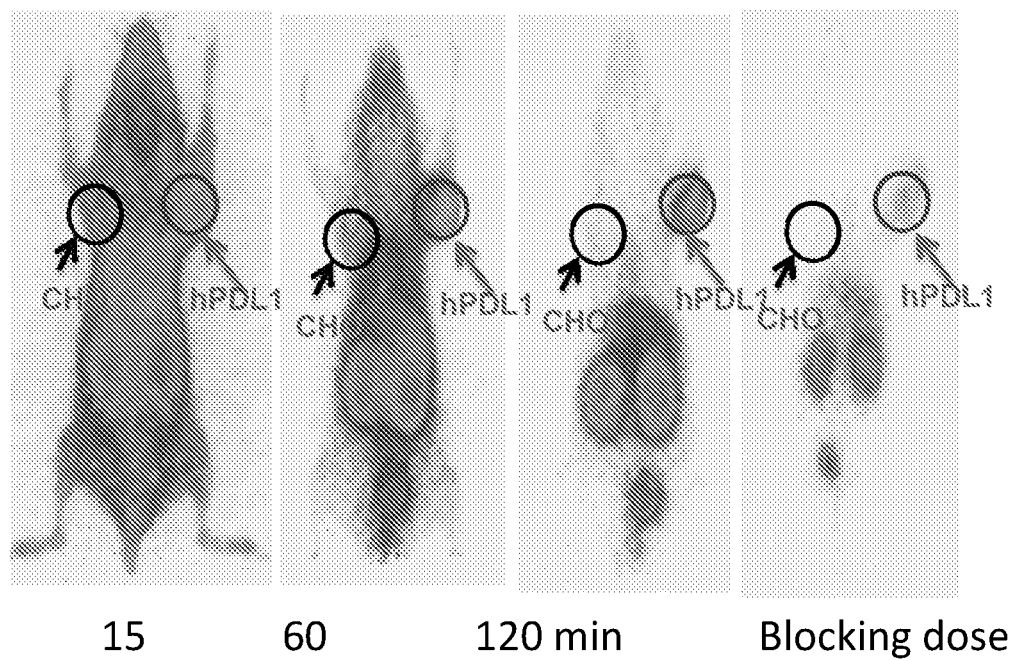
Figure 25B:
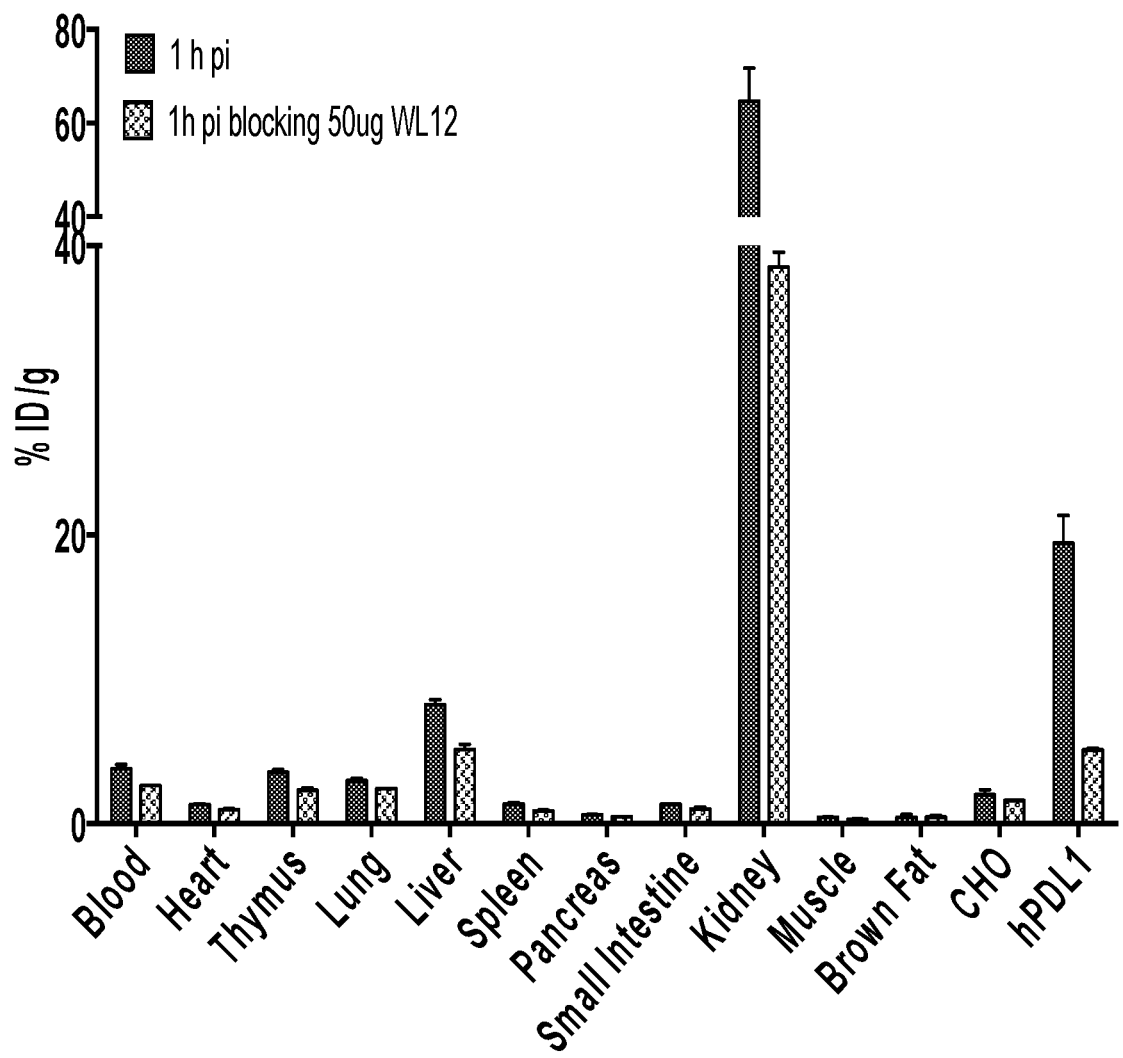
Figure 26:
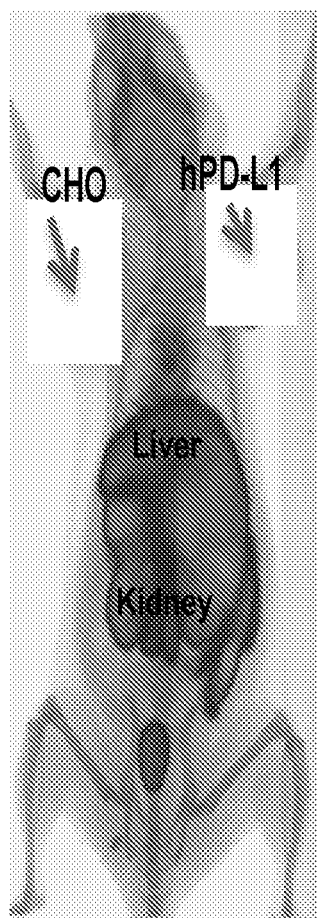
Figure 27:
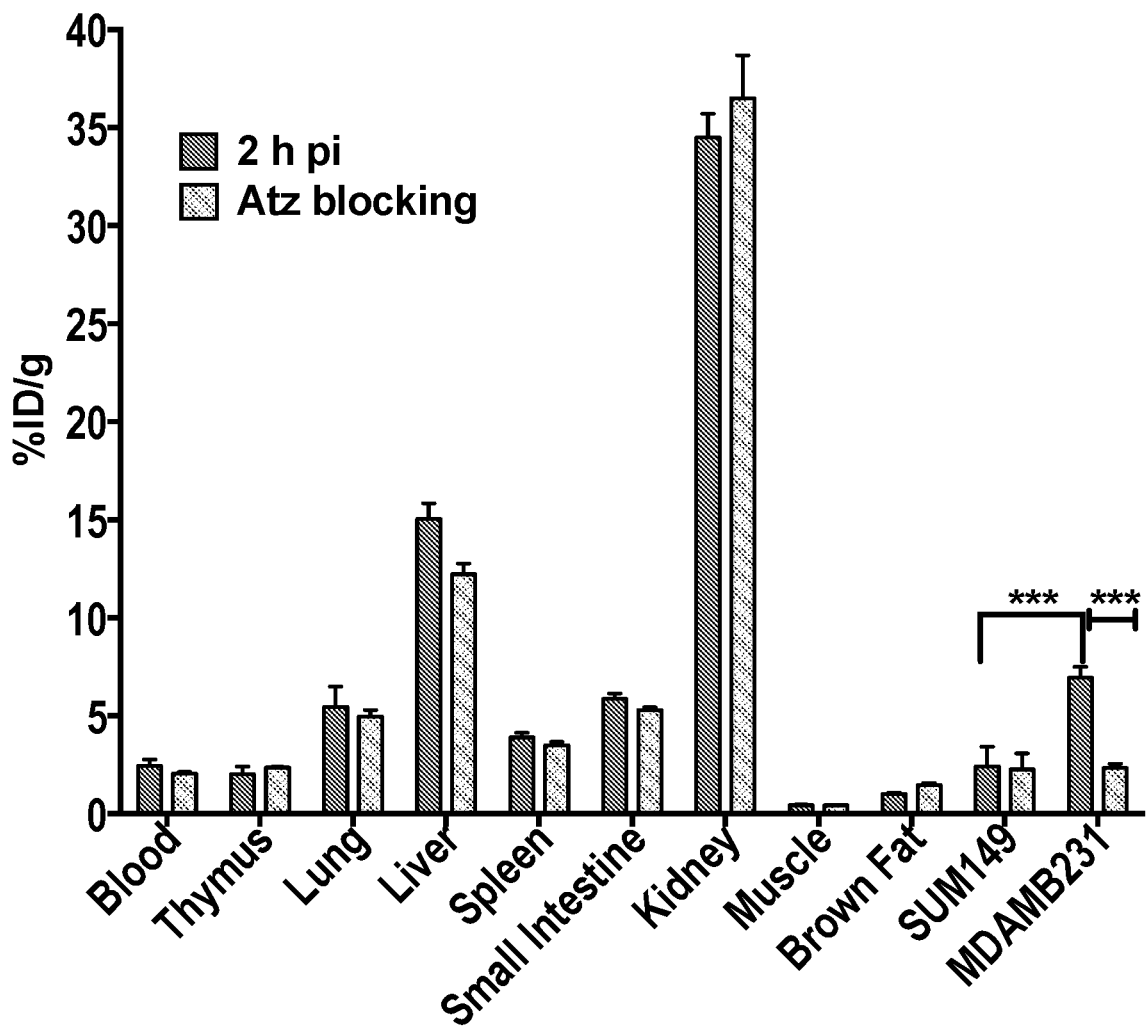
Figure 28:
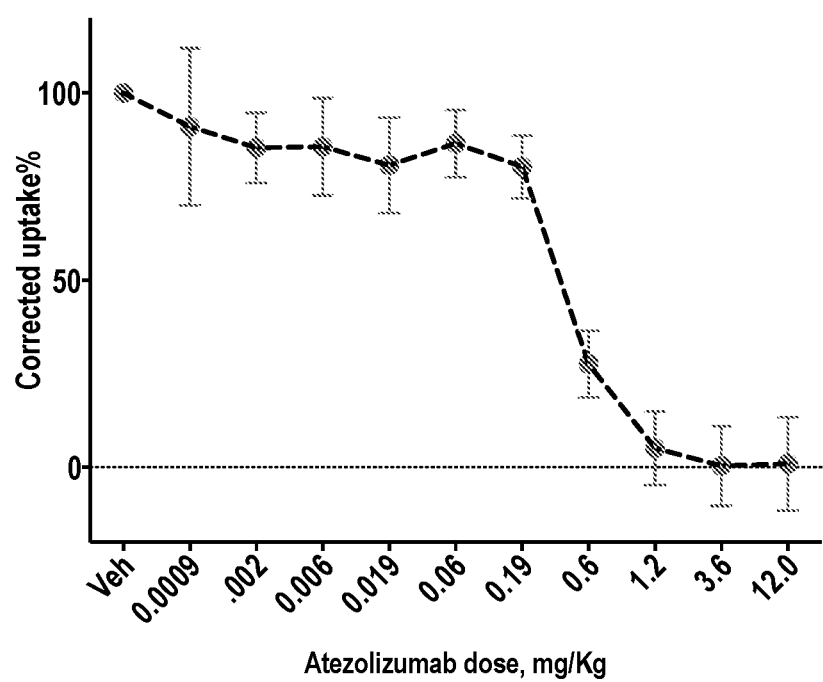
Figure 29:
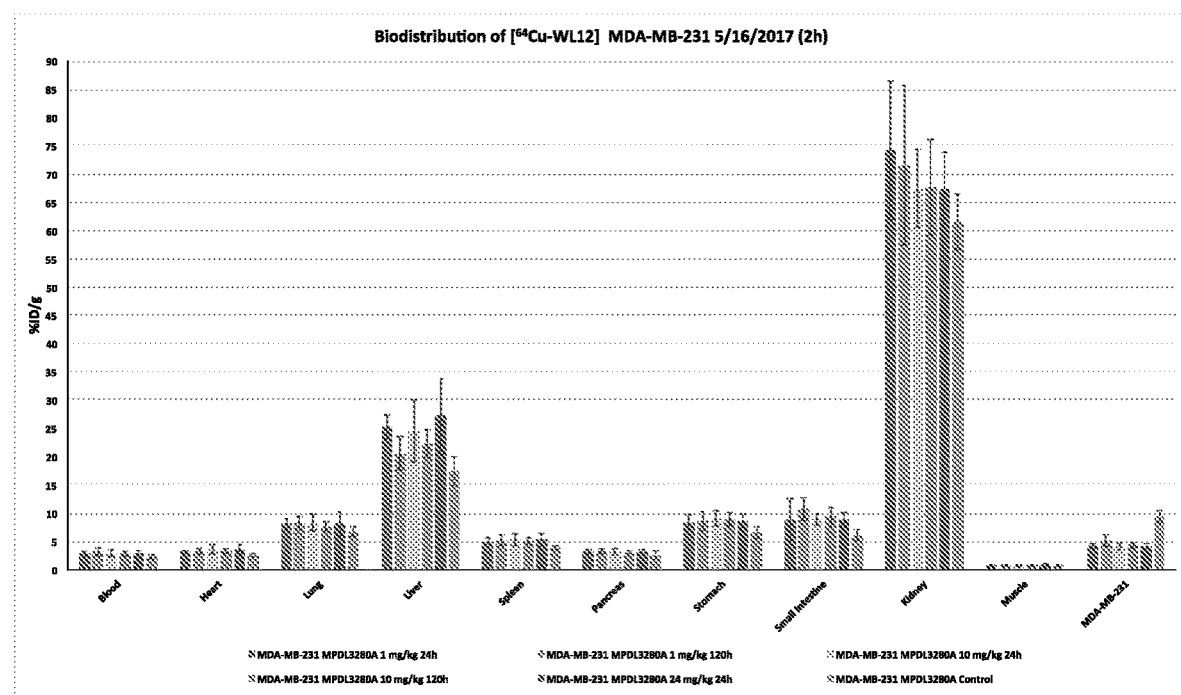

Having thus described the presently disclosed subject matter in general terms, reference will now be made to the accompanying Figures, which are not necessarily drawn to scale, and wherein:

FIG. 1A, FIG. 1B, and FIG. 1C show WL12 binding to PD-L1. FIG. 1A shows structural representation of WL12 and its analogs and the amino acid sequence of WL12 (WL12 amino acid sequence=Cyclo-(-Ac-Tyr-NMeAla-Asn-Pro-His-Leu-Hyp-Trp-Ser-Trp(methyl)-NMeNle-NMeNle-Lys-Cys-)-Gly-NH2); FIG. 1B shows predicted binding mode of WL12 to PD-L1. WL12 forms a beta sheet-like structure in the groove of PD-L1. WL12 is shown in cyan. The surface representation of PD-L1 is shown in gray, with the ribbons and key side chains shown in magenta; and FIG. 1C shows that WL12 mimics PD-1 binding to PD-L1. The structure of PD-1 is shown in teal. The two main interacting beta strands of PD-1 overlap well with the conformation adopted by WL12 bound to PD-L1;

FIG. 2 shows far-UV CD spectra of the peptide WL12;

FIG. 3 shows electrospray ionization (ESI) mass spectrum of WL; theoretical chemical formula: $C_{91}H_{128}N_{22}O_{20}S_2$. Observed m/z: 1882.7–$(M+1)^{+1}$, 941.9–$(M+2)^{+2}/2$. Expected: 1882.19;

FIG. 4 shows RP-HPLC purification of WL12D;

FIG. 5 shows low resolution mass spectrum of PDL1-PD; theoretical chemical formula: $C_{91}H_{128}N_{22}O_{20}S_2$ exact mass: 2339.14, molecular weight: 2340.65, observed m/z: 2340.9–$(M+1)^{+1}$, 1171.1–$(M+2)^{+2}/2$ and 781.1–$(M+2)^{+3}/3$;

FIG. 6 shows RP-HPLC purification of [PDL1-PD-$Cu^{2+}$];

FIG. 7 shows low resolution mass spectrum of [PDL1-PD-$Cu^{2+}$] complex; theoretical chemical formula: $C_{110}H_{156}N_{26}O_{29}S$ exact mass: 2400.05, molecular weight: 2402.18, observed m/z: 2402.6–$(M+1)^{+1}$, 1201.9–$(M+2)^{+2}/2$;

FIG. 8A, FIG. 8B, and FIG. 8C show in vitro characterization of PD-L1 binding peptide WL12. FIG. 8A shows competitive inhibition assay demonstrating the affinity of WL12 analogs for inhibiting PD-1:PD-L1 interaction; FIG. 8B shows flow cytometry histograms of cell lines used for in vitro studies showing variable PD-L1 expression; and FIG. 8C shows that [$^{64}$Cu]W12 demonstrates increased binding to cells with high PD-L1 expression which could be blocked by excess peptide (PEP);

FIG. 9 shows a representative curve of PD-L1 binding to PD-1; $K_D$=69.66±11.65 nM (95% CI 44.82-94.48 nM);

FIG. 10 shows a representative curve for inhibition of PD-L1 binding to PD-1 with WL12D-$Cu^{2+}$ complex; $IC_{50}$=2.97 nM (95% CI 2.17-40.5 nM) $K_i$=1.38 nM (95% CI 1.01-1.89 nM);

FIG. 11 shows RP-HPLC chromatograms of [$^{64}$Cu]WL12 radiotracer (red) and "cold" WL12-$Cu^{2+}$ complex;

FIG. 12 shows a RP-HPLC chromatogram of the mixture of PDL1-PD and [PDL1-PD-$Cu^{2+}$];

FIG. 13 shows mean fluorescence intensity values of various cell lines used for uptake assays;

FIG. 14 shows the correlation of cell line MFI vs % ID;

FIG. 15A and FIG. 15B show rapid in vivo detection of tumor PD-L1 expression with [$^{64}$Cu]WL12. NSG mice with hPD-L1 (red arrow) and CHO tumors (blue arrow) were administered intravenously with 150 μCi of [$^{64}$Cu]WL12 and images were acquired at 10, 30, 60 and 120 min after the injection of the radiotracer. FIG. 15A shows cross sectional (top) and 3D volume rendered (bottom) images demonstrating specific accumulation of [$^{64}$Cu]WL12 in hPD-L1 tumors; and FIG. 15B shows that PD-L1 IHC demonstrates strong immunoreactivity (brown color) in hPD-L1 tumors;

FIG. 16 shows specific uptake of [$^{64}$Cu]WL12 in hPD-L1 tumors in NSG mice. Representative volume rendered PET-CT image of an NSG mouse harboring hPD-L1 and CHO tumors and injected with [$^{64}$Cu]WL12 at 24 h after the injection of the tracer. Increased uptake in hPD-L1 (red arrow) tumor compared to CHO (blue arrow) tumor confirms PD-L1 mediated uptake of the radiotracer;

FIG. 17 shows ex vivo biodistribution analysis of [$^{64}$Cu]WL12 in NSG mice with hPD-L1 and CHO tumors. NSG mice were administered intravenously with 20 μCi of [$^{64}$Cu]WL12 and tissues were harvested at 60 and 120 min after the injection. For blocking studies, mice received excess of peptide (pep) with the radiotracer injection;

FIG. 18A, FIG. 18B, and FIG. 18C show: (FIG. 18A) the structure of a Wl2-IR800CW conjugate (chemical formula: $C_{137}H_{177}N_{24}O_{34}$, molecular weight: 2864.34), (FIG. 18B) HPLC chromatogram of WL12-IR800CW with UV-Vis spectrum recorded under the peak (insert) indicating conjugation of the dye with peptide; and (FIG. 18C) an ESI-MS spectrum of the WL12-IR800CW conjugate, correlating with the expected molecular weight;

FIG. 19A, FIG. 19B, and FIG. 19C show the evaluation of WL12-IR800CW in mice bearing CHO and hPDL1 tumors: (FIG. 19A) representative images of mouse injected with 5 nmole of WL12-IR800CW and ex vivo organs recorded 24 h post injection of the conjugate, (FIG. 19B, blocking) representative images of mouse injected with 25 nmole of unmodified WL12 and 5 nmole of WL12-IR800CW, acquired 24 h pi; and (FIG. 19C) quantification of ex vivo biodistribution of WL12-IR800CW in selected organs and tumors obtained from mice treated with 1 nmole, 3 nmole, and 5 nmole of the conjugate and blocking with WL12 (number denotes corresponding organs, n=4);

FIGS. 20A, 20B, 20C, and 20D show that [111In]atezolizumab uptake in human NSCLC and TNBC xenografts is not entirely expression dependent. (A) Flow cytometric analysis of various TNBC and NSCLC cell lines showing variable PD-L1 expression; (B) Binding of [$^{111}$In]AtzMab to cancer cell lines is PD-L1 expression dependent; (C) Increased uptake of [$^{111}$In]AtzMab in PD-L1high MDAMB231 TNBC xenografts compared to PD-L1low SUM149; and (D) Increased uptake of [$^{111}$In]AtzMab in PD-L1high H2444 NSCLC xenografts compared to PD-L1low H1155. Corresponding histology is shown. From Chatterjee, et al., Oncotarget, 2016;

FIGS. 21A, 21B, 21C, and 21D show that [$^{64}$Cu]WL12-PET detects AtzMab accumulation in the tumors. (A) Whole body [$^{64}$Cu]WL12 image shows specific accumulation of radioactivity on hPD-L1 tumors by 60 min p.i.; (B) [$^{64}$Cu]WL12 uptake is significantly reduced in hPD-L1 tumors in mice receiving 20 mg/Kg dose of AtzMab 24 h prior to tracer injection; (C) Corresponding biodistribution studies confirming the potential of [$^{64}$Cu]WL12 to detect AtzMab PD-L1 engagement in the tumors; and (D) WL12 inhibits AtzMab binding to PD-L1. hPD-L1 cells incubated with serial dilutions of WL12 were stained with Cy5-AtzMab or commercial BD antibody BD-MIH1-PE. Mean fluorescence intensity (MFI) vs. peptide concentration plot shows an IC50 of 2.5 nM and 37.8 nM for Cy5-AtzMab and BD-MIH1-PE, respectively;

FIG. 22 shows that [64Cu]WL12-PET detects AtzMab accumulation in triple negative breast cancer xenografts. [64Cu]WL12 uptake is significantly reduced in MDAMB231 tumors in mice receiving 20 mg/Kg dose of AtzMab 24 h prior to tracer injection;

FIG. 23A, FIG. 23B, and FIG. 23C show (A) the structure of Wl12-IR800 conjugate (chemical formula: $C_{137}H_{177}N_{24}O_{34}$, molecular weight: 2864.34); (B) HPLC chromatogram of WL12-IR800 with UV-Vis spectrum recorded under the peak (insert) indicating conjugation of the dye with peptide; and (C) ESI-MS spectrum of the WL12-IR800, correlating with expected molecular weight;

FIGS. 24A, 24B, and 24C show the evaluation of WL12-IR800 in mice bearing CHO and hPDL1 tumors: (A) representative images of mouse injected with 5 nmole of WL12-IR800 and ex vivo organs recorded 24 h post injection of the conjugate; (B, blocking) representative images of mouse injected with 25 nmole of unmodified WL12 and 5 nmole of WL12-IR800, acquired 24 h pi; and (C) quantification of ex vivo biodistribution of WL12-IR800 in selected organs and tumors obtained from mice treated with 1 nmole, 3 nmole and 5 nmole of the conjugate and blocking with WL12 (number denotes corresponding organs, n=4);

FIG. 25A and FIG. 25B show the evaluation of [$^{68}$Ga]WL12 in CHO and CHO-hPDL1tumor models: (A) PET-CT (volume rendered) images of [$^{68}$Ga]WL12 uptake in CHO-hPD-L1 (red arrow, high PD-L1 expression) and CHO (black arrow, low PD-L1 expression) tumors (n=3) confirm PD-L1 mediated uptake of the radiotracer; and (B) ex vivo biodistribution analysis at 1 h after the injection of [$^{68}$Ga]WL12 in the same tumor model. Blocking dose cohorts were co-injected with 50 microgram of the cold peptide;

FIG. 26 shows the evaluation of [$^{18}$F]WL12 in CHO and CHO-hPDL1tumor models. (A) PET-CT (volume rendered) images of [$^{18}$F]WL12 uptake in CHO-hPD-L1 (red arrow, high PD-L1 expression) and CHO (blue arrow, low PD-L1 expression) tumors (n=3) confirm PD-L1 mediated uptake of the radiotracer;

FIG. 27 shows mice with MDAMB231 and SUM149 tumors were injected with 20 mg/Kg dose of atezolizumab. Twenty hours after mAb dosing, mice were injected with 20 μCi of [$^{64}$Cu]WL12 and biodistribution studies were performed 24 h after tracer injection. Data demonstrate that atezolizumab binding to PD-L1 in the tumors can be quantified by [$^{64}$Cu]WL12;

FIG. 28 shows dose dependent PD-L1 occupancy determination for PD-L1 therapeutic antibody atezolizumab. Mice with MDAB231 breast tumors were injected with various doses of atezolizumab and 24 h after, mice were injected with [$^{64}$Cu]WL12 and biodistribution studies were performed at 2 h after tracer injection. Data show that [$^{64}$Cu]WL12 accumulation in the tumors is reduced with increasing antibody dose;

FIG. 29 shows time and dose dependence changes in PD-L1 occupancy of atezolizumab measured by [$^{64}$Cu]WL12. MDAMB231 tumor bearing mice received 1 or 10 mg/Kg dose of atezolizumab. At 24 or 120 h after the mAb dosing, mice were injected with [$^{64}$Cu]WL12 and tumor accumulation of radioactivity was measured by biodistribution studies. As anticipated, at 10 mg/Kg dose complete blockade of PD-L1 was observed both at 24 and 120 h.

Figure 32:
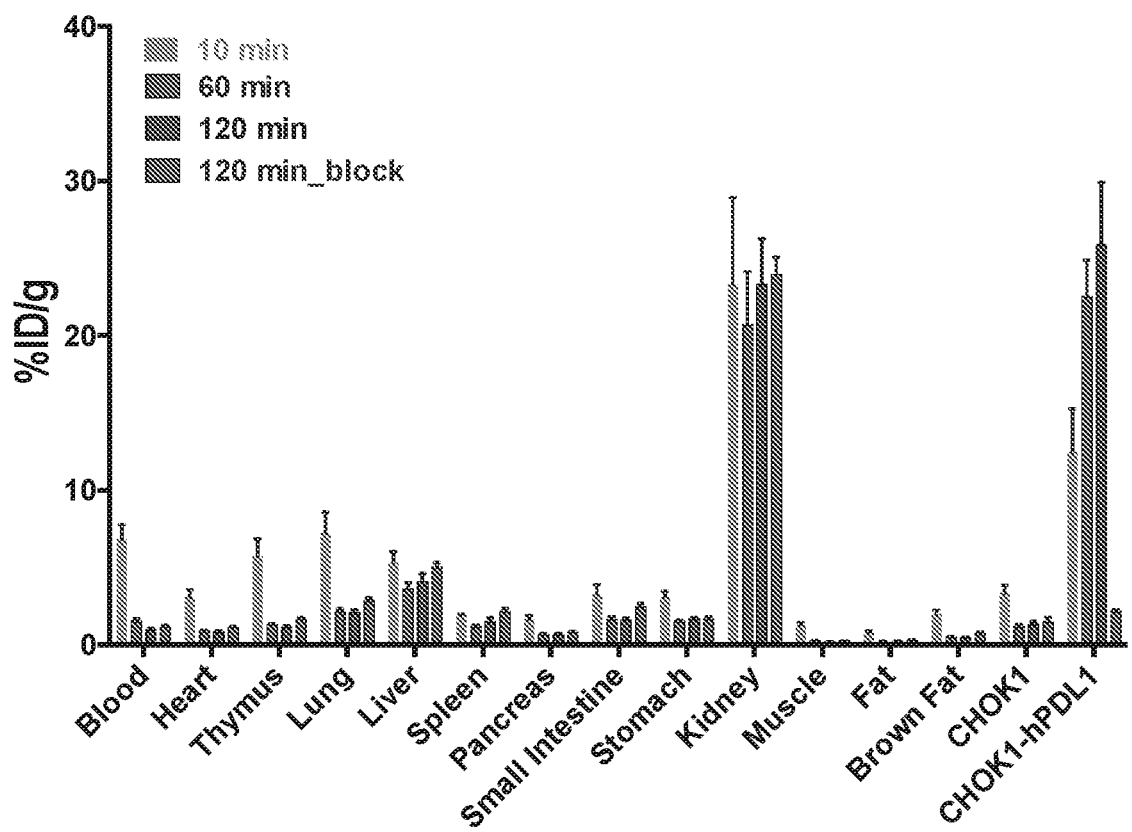
Figure 33A:
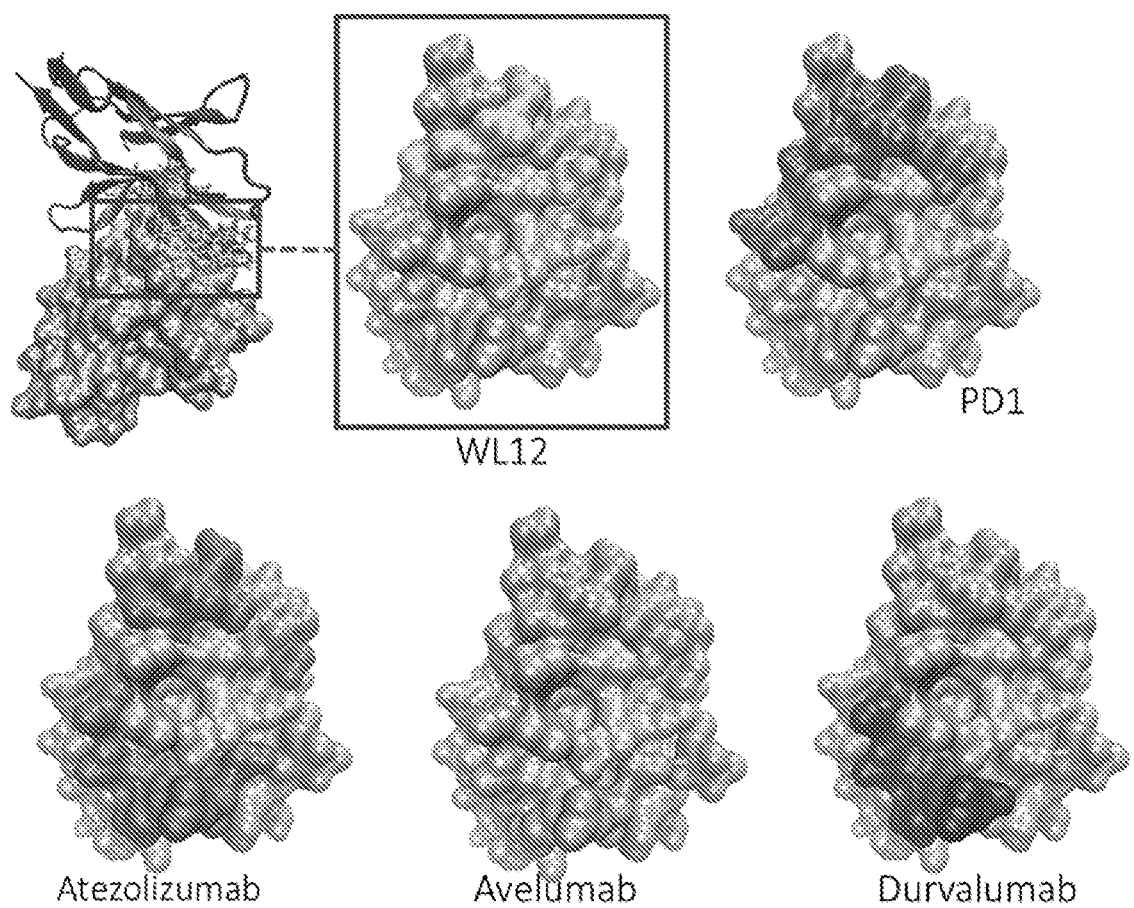
Figure 33B:
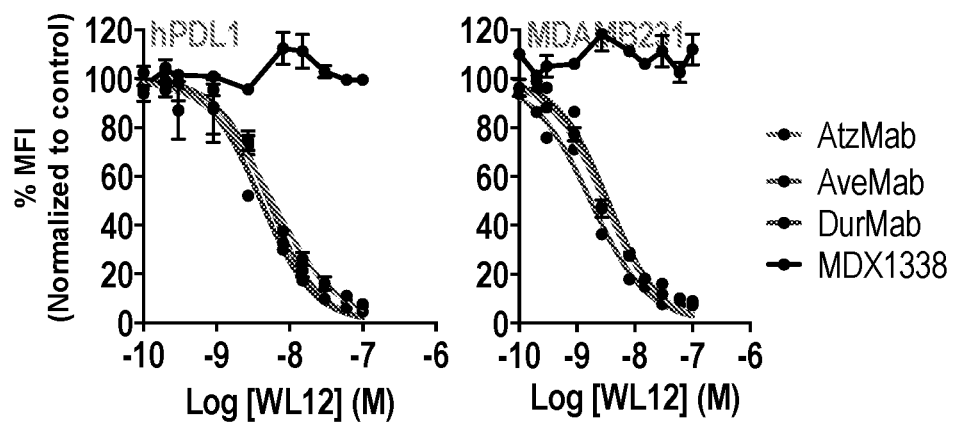
Figure 33C:
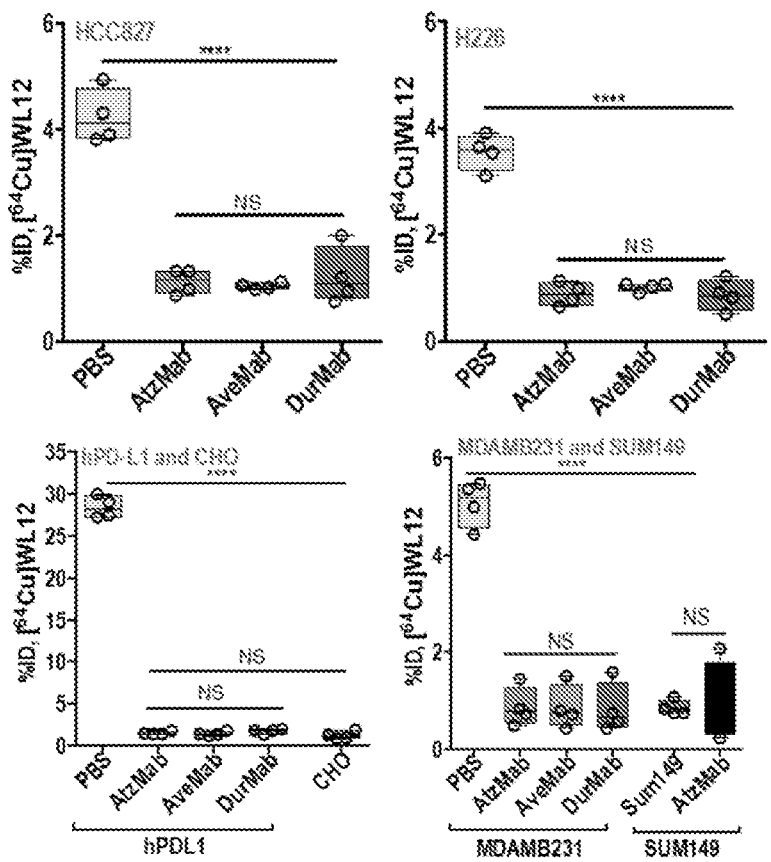
Figure 34A:
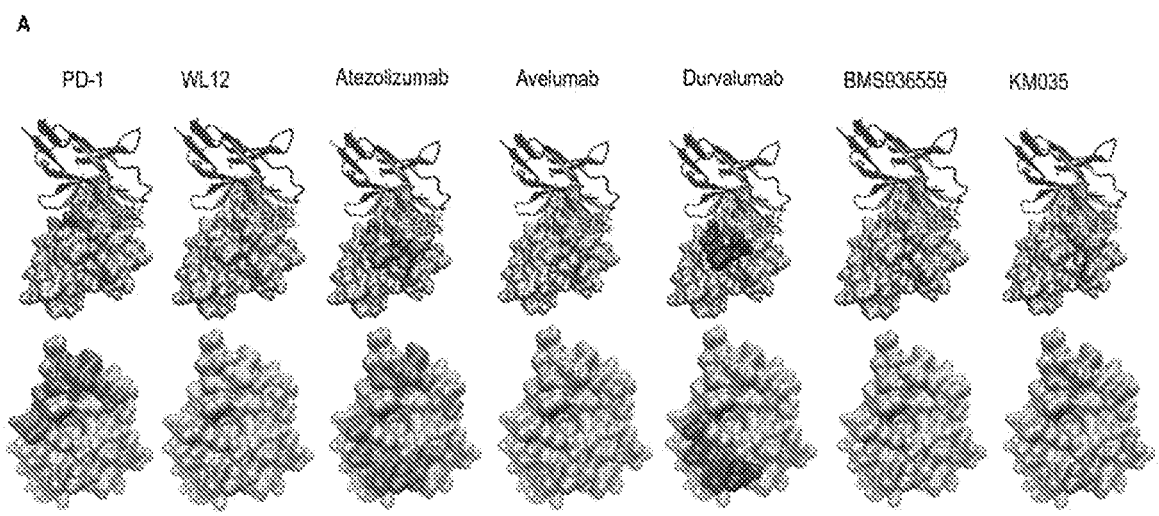
Figure 34B:
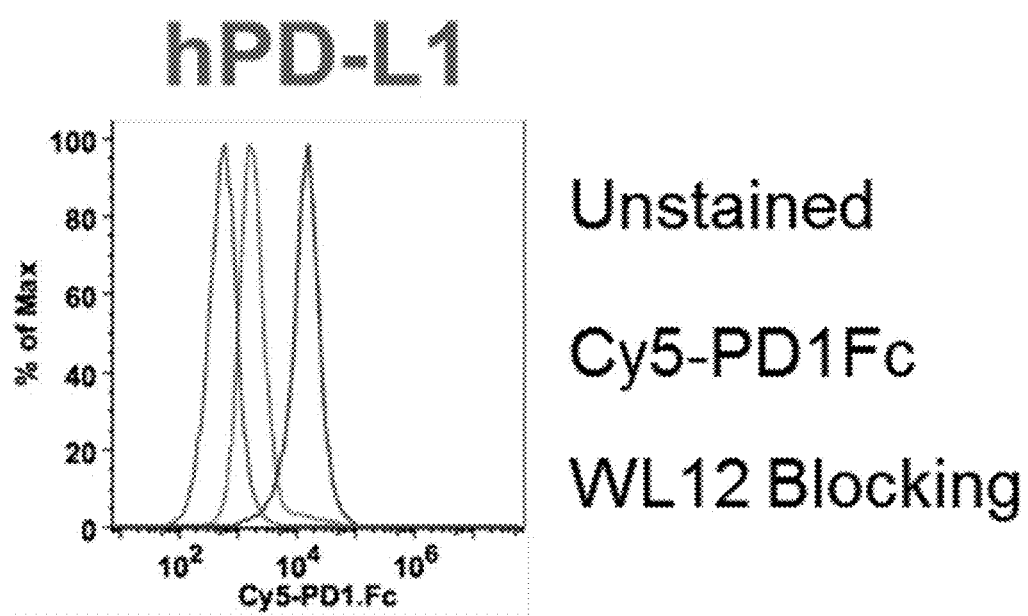
Figure 35A:
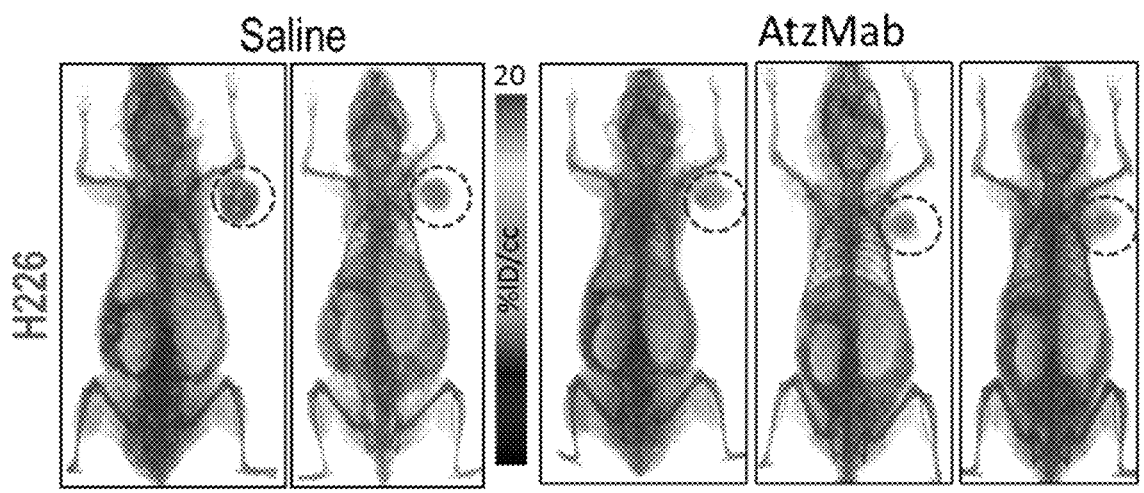
Figure 35B:
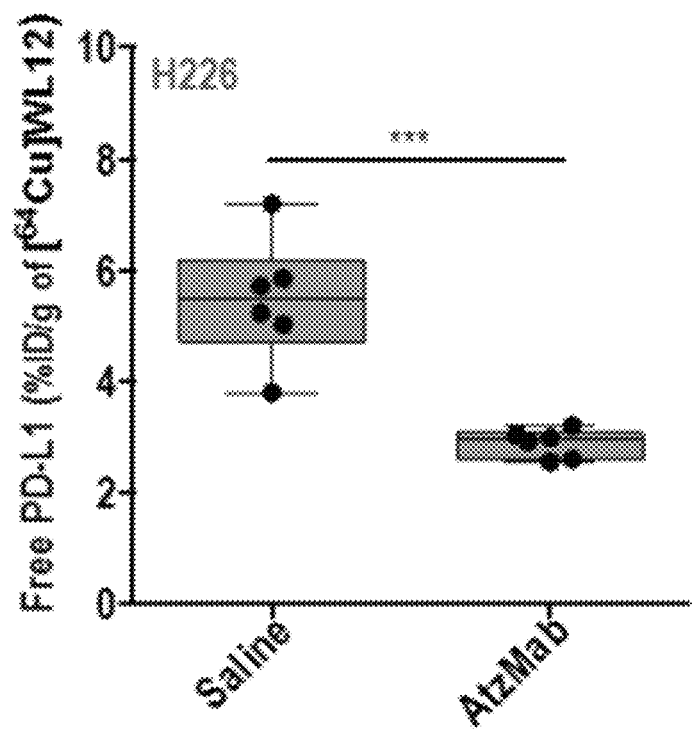
Figure 35C:
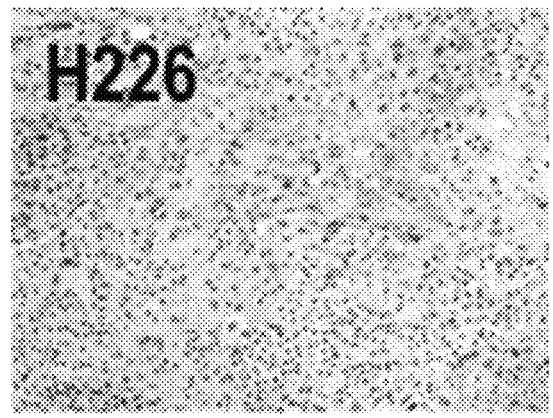
Figure 35D:
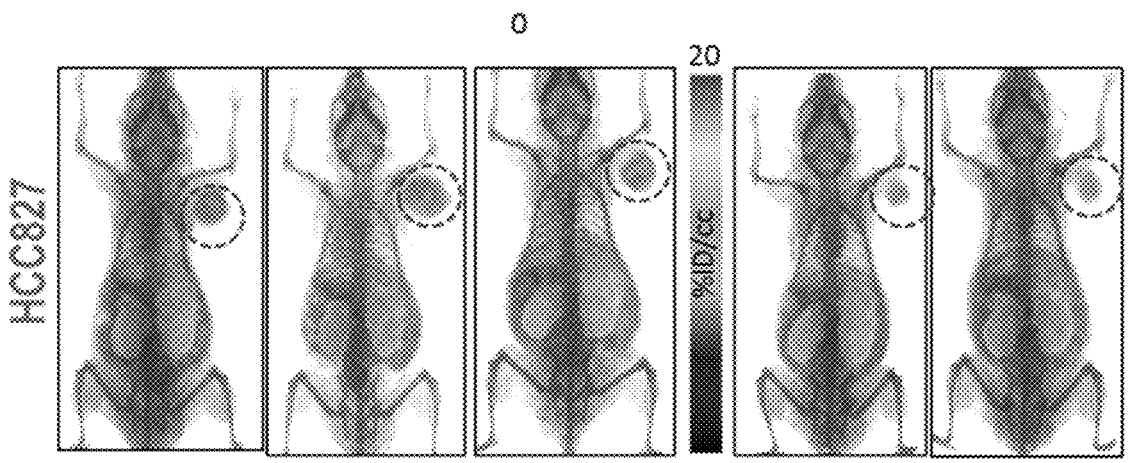
Figure 35E:
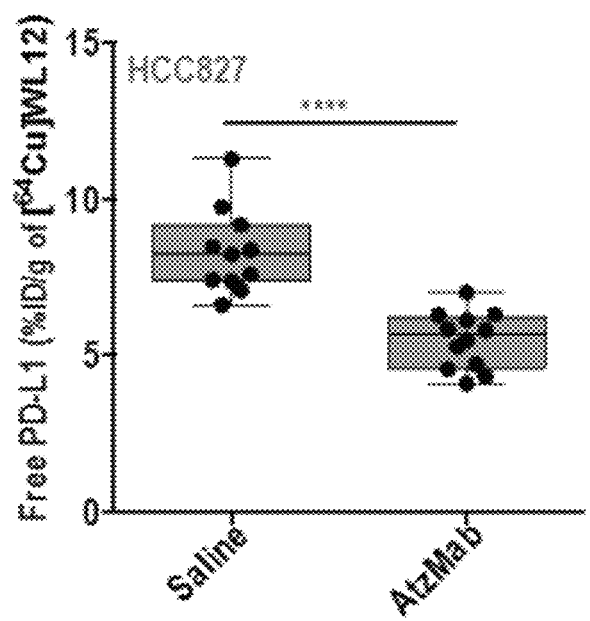
Figure 35F:
Figure 35G:
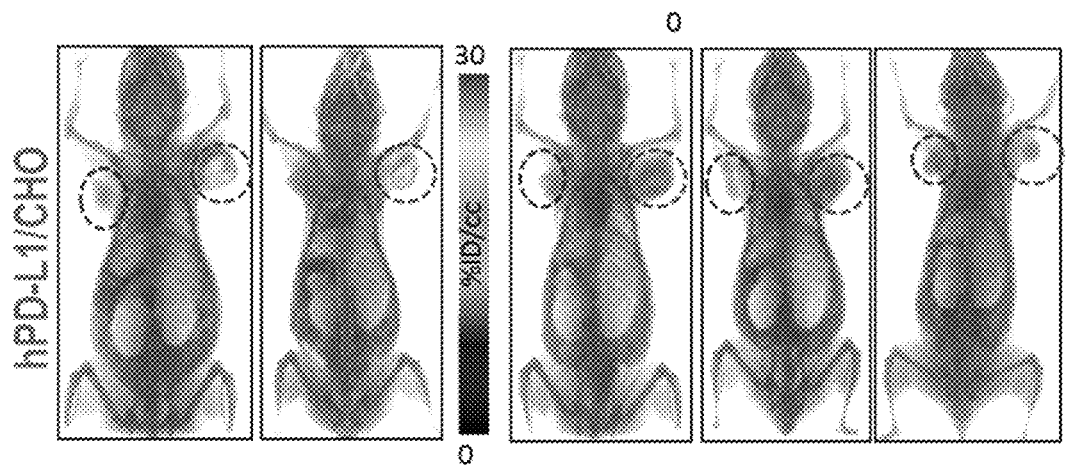
Figure 35H:
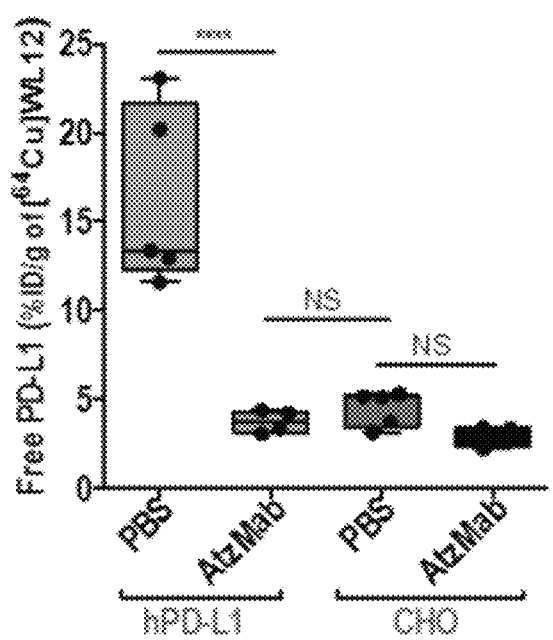
Figure 35I:
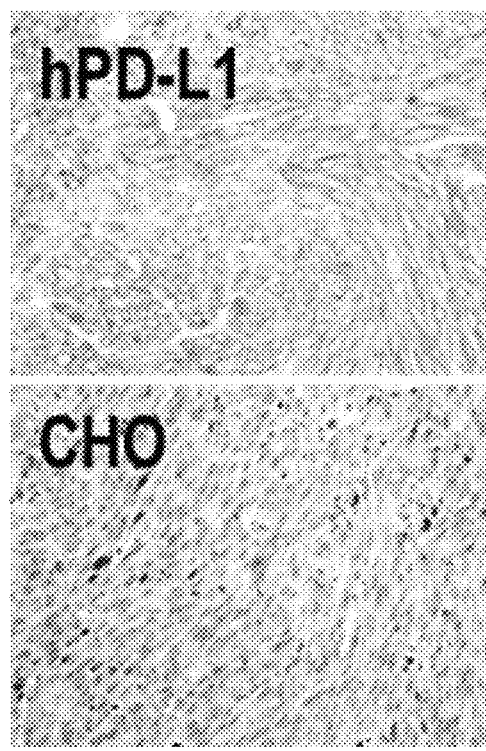
Figure 36A:
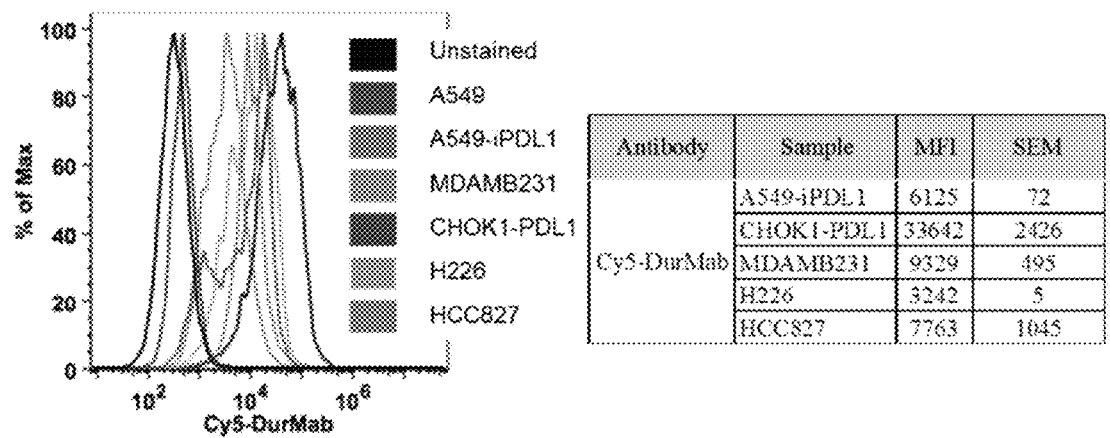
Figure 36B:
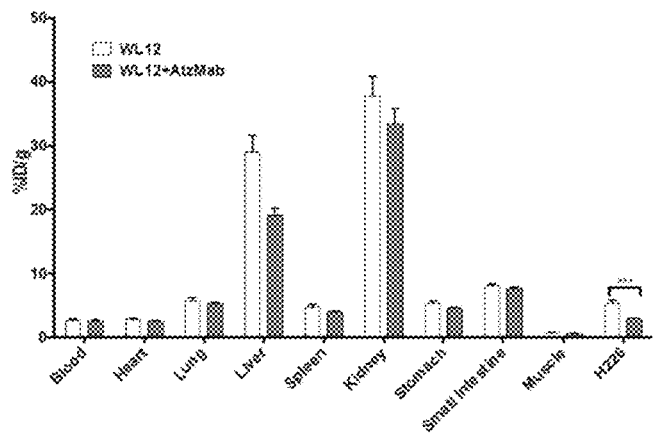
Figure 36C:
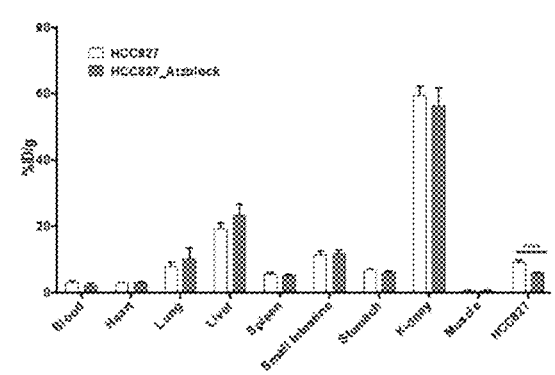
Figure 36D:
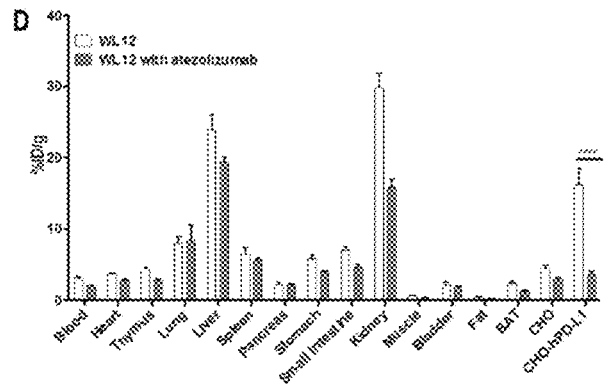
Figure 38:
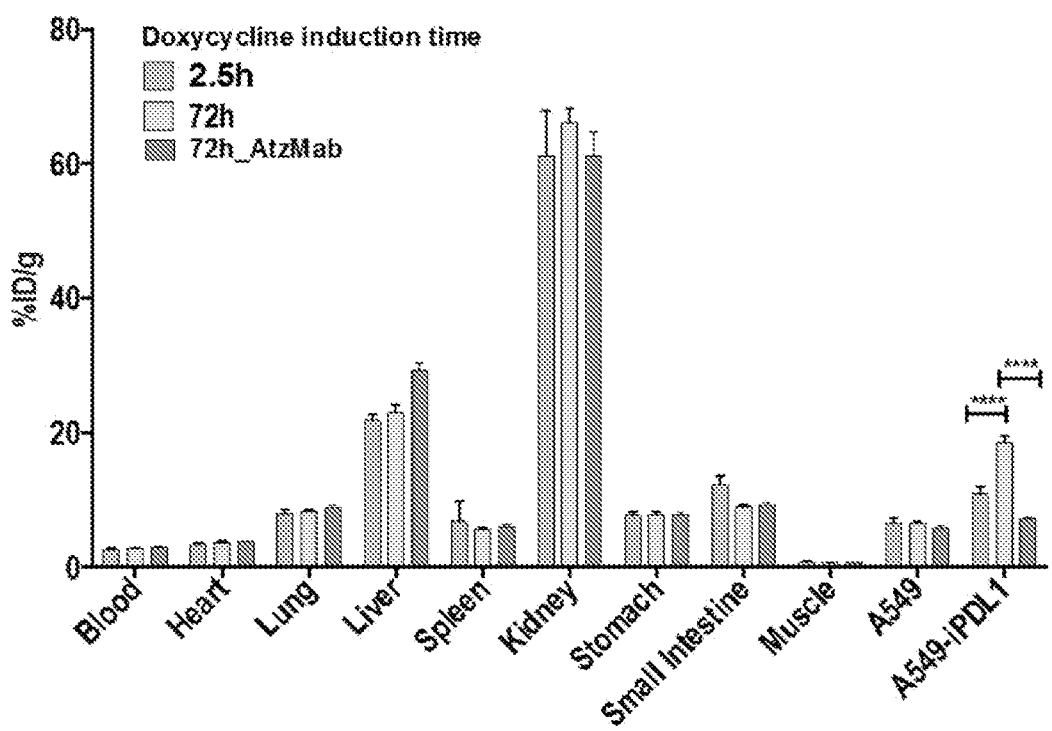
Figure 40:
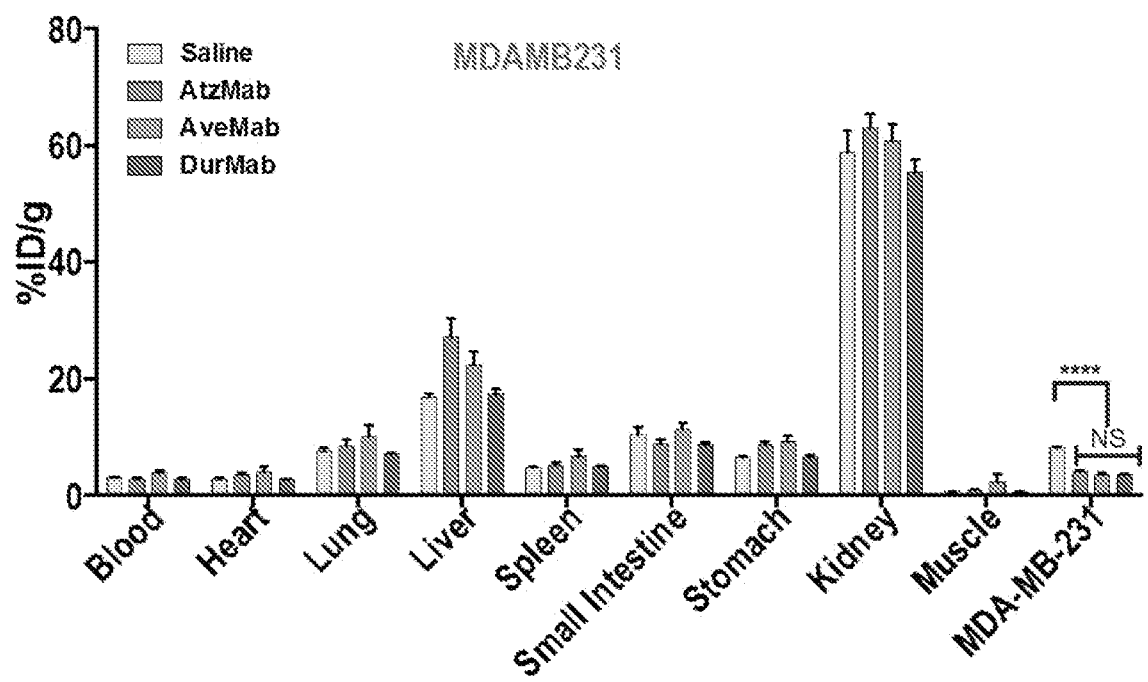
Figure 42:
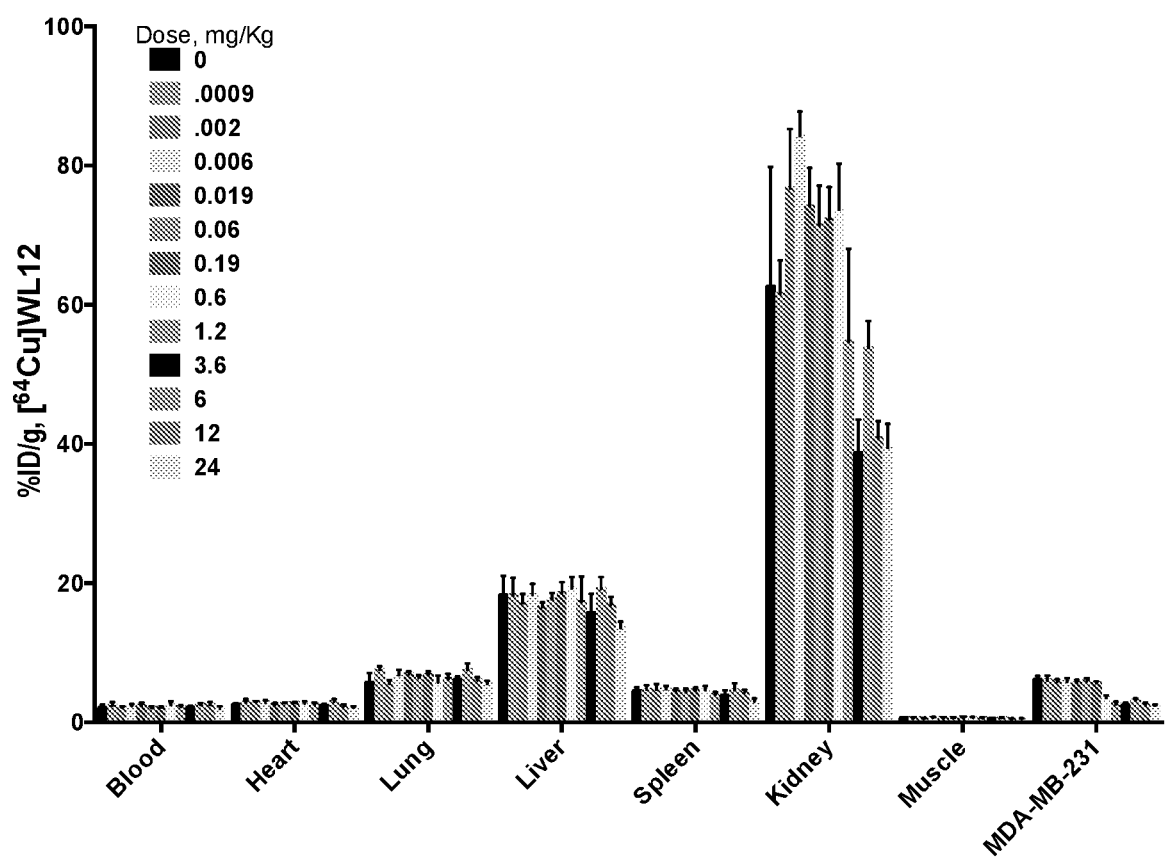
Figure 43:
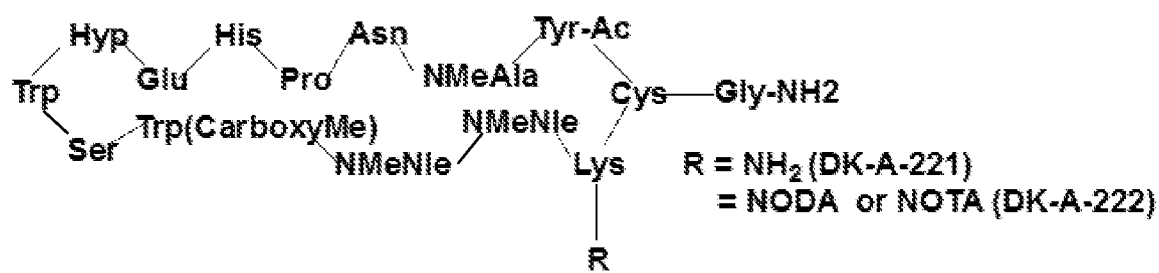

Whereas at 1 mg/Kg dose, increased accumulation of [$^{64}$Cu] WL12 can be seen at 120 h but not at 24 h suggesting a washout of atezolizumab from the tumor over time when low mAb doses are used. These data suggest that PD-L1 therapeutic mAb residence time at the tumor could be analyzed using the presently disclosed peptides;

FIG. 30 shows the chemical structures of DK-A-221 and DK-A-222;

FIG. 31A and FIG. 31B show data regarding the DK222 PD-L1 binding peptide. NOTA conjugated DK222 was synthesized and evaluated in mice bearing CHO/CHO-HPD-L1 tumors. Imaging (A) and biodistribution (B) data show superior pharmacokinetics of [$^{64}$Cu]DK222;

FIG. 32 shows biodistribution of [$^{64}$Cu]DK222 in NSG mice bearing CHO/CHO-hPD-L1 tumors;

FIG. 33A, FIG. 33B, and FIG. 33C demonstrate that WL12 inhibits interaction between PD-1 and PD-L1 therapeutics in vitro. FIG. 33A shows that the WL12 binding mode to PD-L1 (green and cyan) overlaps those of PD-1 to AtzMab (red and cyan), AveMab (orange and cyan) and DurMab (blue and cyan). Non-interacting residues are shown in gray. The variety of contacts encompassing the shared binding region (cyan) illustrates the diverse binding mechanisms of different therapeutic mAbs. FIG. 33B shows that WL12 inhibits Cy5-conjugated-AtzMab, AveMab and DurMab to PD-L1 as demonstrated through competitive inhibition. Mean fluorescence intensities were determined by flow cytometry. FIG. 33C shows that [$^{64}$Cu]WL12 binding to PD-L1-positive HCC827, H226, hPD-L1, and MDAMB231 cells is inhibited in the presence of 60 nM AtzMab, AveMab and DurMab, compared to PBS control. [$^{64}$Cu]WL12 binding in PD-L1-negative CHO and SUM149 cells is also shown. ****, P<0.0001; NS, not significant;

FIG. 34A is a representation of the molecular surface surrounding the PD-L1 interaction interface with PD-1. The common residues involved in interactions with PD-1 competitive therapeutics is shown in cyan, the molecular contacts specific to the PD-1 interactions are shown in purple, and non-interacting residues are shown in grey. To illustrate the overlap in molecular interaction, the structure of bound PD-1 is shown in purple and the predicted conformation of WL12 is shown in green;

FIG. 34B, shows that WL12 inhibits binding of Cy5-conjugated PD-1-Fc protein to PD-L1 in hPD-L1 cells. Mean fluorescence intensity determined by flow cytometry;

FIG. 34C, shows that WL12 (5 nM) inhibits binding of Cy5-conjugated- AtzMab, AveMab and DurMab (2 nM) to PD-L1 in HCC827 and H226 cells. Mean fluorescence intensity determined by flow cytometry and FIG. 34D show mean fluorescence intensity determined by flow cytometry from FIG. 34B and FIG. 34C;

FIG. 35A, FIG. 35B, FIG. 35C, FIG. 35D, FIG. 35E, FIG. 35F, FIG. 35G, FIG. 35H, and FIG. 35I demonstrate that PD-L1 engagement by PD-L1 mAbs is quantified at the tumor using [$^{64}$Cu]WL12 in xenografts with variable PD-L1 expression. FIGS. 35A-35H show reduced uptake of [$^{64}$Cu] WL12 in H226 (FIG. 35A, FIG. 35B), HCC827 (FIG. 35C, FIG. 35D), and hPD-L1/CHO (FIG. 35G, FIG. 35H) xenografts in mice treated with 20 mg/kg of AtzMab 24 h prior to radiotracer injection, compared to saline treated controls. Whole-body, volume-rendered [$^{64}$Cu]WL12 PET-CT images (FIG. 35A, FIG. 35D, FIG. 35G) and ex vivo biodistribution (FIG. 35B, FIG. 35E, FIG. 35H). FIG. 35C, FIG. 35F and FIG. 35I show IHC staining for PD-L1 is shown from the corresponding tumor **, P<0.0001; *, P<0.001; NS, not significant;

FIG. 36A, FIG. 36B, FIG. 36C, and FIG. 36D show FIG. 36A, PD-L1 expression in various cell lines and the corresponding mean fluorescence intensity values. FIG. 36B, FIG. 36C, and FIG. 36D, Ex vivo biodistribution of [$^{64}$Cu] WL12 in tumor bearing mice bearing H226 (B), HCC827 (C) or hPD-L1/CHO (D) tumors receiving 20 mg/Kg dose of AtzMab 24 h prior to tracer injection. Data shown is mean±SEM. **, P<0.0001; *, P<0.001; NS, not significant;

FIG. 37A, FIG. 37B, FIG. 37C, FIG. 37D, FIG. 37E, and FIG. 37F demonstrate dynamic changes in tumor PD-L1 expression and its engagement by AtzMab detected using [$^{64}$Cu]WL12. FIG. 37A shows increased PD-L1 cell surface expression in A549-iPDL1 cells treated with doxycycline for 6 h and 72 h. Flow cytometry histogram. FIG. 37B shows that WL12 inhibits (5 nM) binding of Cy5-conjugated-AtzMab, AveMab and DurMab (2 nM) to A549-iPD-L1 cells treated with doxycycline for 72 h. FIG. 37C shows that [$^{64}$Cu]WL12 binding to A549-iPDL1 cells (72 h doxycycline) is significantly reduced in the presence of 60 nM AtzMab, compared to controls. FIG. 37D and FIG. 37E show that [$^{64}$Cu]WL12 uptake in A549-iPDL1 xenografts is significantly lower in mice receiving intravenous AtzMab 24 h prior to radiotracer injection, compared to saline controls and similar to parent A549 xenografts. Volume rendered whole body PET-CT images (D), and ex vivo quantification (FIG. 37E). FIG. 37F shows IHC staining for PD-L1 of the corresponding tumors. ****, P<0.0001; NS, not significant;

FIG. 38 shows ex vivo biodistribution of [$^{64}$Cu]WL12 in A549-iPDL1 and A549 control tumor bearing mice given doxycycline for 72 h and treated with 20 mg/Kg of AtzMab 24 h prior to radiotracer injection. ****, P<0.0001; NS, not significant;

FIG. 39A, FIG. 39B, FIG. 39C, FIG. 39D, FIG. 39E, FIG. 39F demonstrate tumor PD-L1 engagement by three different PD-L1 therapeutic mAbs quantified using [$^{64}$Cu]WL12. FIG. 39A-FIG. 39E. [$^{64}$Cu]WL12 uptake in MDAMB231 xenografts is significantly reduced in mice receiving AtzMab (20 mg/kg), AveMab (10 mg/kg), or DurMab (10 mg/kg) 24 h prior to radiotracer injection. Whole body volume rendered [$^{64}$Cu]WL12 PET-CT images of saline (FIG. 39A), AtzMab (FIG. 39B), AveMab (FIG. 39C), DurMab (FIG. 39D) treated mice, and ex vivo biodistribution (FIG. 39E)). FIG. 39F shows IHC staining for PD-L1 in the corresponding tumor.****, P<0.0001; NS, not significant;

FIG. 40 shows, Ex vivo biodistribution of [$^{64}$Cu]WL12 in MDAMB231 bearing mice treated with AtzMab (20 mg/Kg), AveMab (10 mg/Kg), or DurMab (10 mg/Kg) for 24 h prior to radiotracer injection. ****, P<0.0001; NS, not significant;

FIG. 41A, FIG. 41B, FIG. 41C, FIG. 41D, and FIG. 41E demonstrate the effect of dose and time on tumor PD-L1 occupancy by AtzMab quantified using [$^{64}$Cu]WL12. FIG. 41A shows dose-exposure relationship depicting the decrease in free PD-L1 ligands, in MDA-MB-231 tumors in mice, with increase in AtzMab dose (mg/kg). Whole body [$^{64}$Cu]WL12 PET-CT images of MDAMB231 tumor-bearing mice receiving 0.06 mg/kg, 0.6 mg/kg and 3.2 mg/kg of AtzMab (FIG. 41A). FIG. 41B and FIG. 41C show ex vivo quantification of [$^{64}$Cu]WL12 uptake in tumors of mice treated with escalating doses of AtzMab (0.0009 to 24 mg/kg). AtzMab was injected 24 h prior to radiotracer injection (FIG. 41B). Percentage of free PD-L1 ligand was calculated relative to the median free PD-L1 ligands measured at 0 mg/kg (FIG. 41C). Blue open dots: measured free PD-L1 ligands for each dose level in mice. Red dashed line:

mean model-predicted dose-response relationship. FIG. 41D and FIG. 41E show the AtzMab (mg/kg) dose effect on tumor PD-L1 occupancy over time depicting an increase in free PD-L1 ligands in 0.6 or 1 mg/kg dose of AtzMab, but not with 10 or 20 mg/kg AtzMab dose recapitulating the non-linear kinetics of mAb. Whole body volume rendered [$^{64}$Cu]WL12 PET-CT images (D) and ex vivo biodistribution (E).****, P<0.0001; NS, not significant;

FIG. 42 shows ex vivo biodistribution of [$^{64}$Cu]WL12 in MDAMB231tumor bearing mice, with escalating dose of AtzMab (0.0009 to 12 mg/Kg) 24 h prior to tracer injection;

FIG. 43 shows structural representation of DK-A-221 and DK-A-222 and its analogs and the amino acid sequence of DK-A-221 (DK-A-221amino acid sequence=cyclo-)-Ac-Tyr-NMeAla-Asn-Pro-His-Glu-Hyp-Trp-Ser-Trp(Carboxymethyl)-NMeNle-NMeNle-Lys-Cys-)-Gly-NH2).

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Compositions Comprising Imaging Agents

In some embodiments, the presently disclosed subject matter provides highly specific peptide-based positron emission tomography (PET) imaging agents for detecting an immune checkpoint protein, such as PD-L1. These imaging agents can be used to detect tumor PD-L1 expression specifically and soon after administration to a subject.

Accordingly, in some embodiments, the presently disclosed subject matter provides an imaging agent comprising a conjugate of a peptide having a binding specificity for programmed death ligand 1 (PD-L1) and a reporting moiety, and optionally a linker, wherein the linker, when present connects the peptide and the reporting moiety, and when the linker is absent, the reporting moiety is attached directly to the peptide through a primary amine of an amino acid of the peptide. In other embodiments, the reporting moiety is directly incorporated into the peptide, for example, wherein the reporting moiety comprises a radiolabeled amino acid of the peptide, such as radiolabeled iodotyrosine or fluorotyrosine.

In some embodiments, the peptide having binding specificity for programmed death ligand 1 (PD-L1) may interact with four specific amino acids of PD-L1. In particular embodiments, the peptide may interact with amino acids Y56, E58, D61, and A113 of PD-L1. In some embodiments, the peptide having binding specificity for PD-L1 may interact with five specific amino acids of PD-L1. In particular embodiments, the peptide may interact with amino acids Y56, E58, A113, M115 and Y123 of PD-L1. In some embodiments, the peptide that interacts with PD-L1 is the peptide WL12. The peptide WL12 may have the amino acid sequence of Cyclo-(-Ac-Tyr-NMeAla-Asn-Pro-His-Leu-Hyp-Trp-Ser-Trp(methyl)-NMeNle-N MeNle-Lys-Cys-)-Gly-NH2 (SEQ ID NO.:1). In some embodiments, WL12 may interact with four amino acids of PD-L1. In particular embodiments, WL12 may interact with amino acids Y56, E58, D61, and A113 of PD-L1. In some embodiments, WL12 may interact with five amino acids of PD-L1. In particular embodiments, WL12 may interact with amino acids Y56, E58, A113, M115 and Y123 of PD-L1. In other embodiments, the peptide that interacts with PD-L1 is DK-A-221. The peptide DK-A-221 may have the amino acid sequence of Cyclo-(-Ac-Tyr-NMeAla-Asn-Pro-His-Glu-Hyp-Trp-Ser-Trp(Carboxymethyl)-NMeNle-N MeNle-Lys-Cys-)-Gly-NH2 (SEQ ID NO.: 2). In some embodiments, DK-A-221 may interact with four amino acids of PD-L1. In particular embodiments, DK-A-221 may interact with amino acids Y56, E58, D61, and A113 of PD-L1. In some embodiments, DK-A-221 may interact with five amino acids of PD-L1. In particular embodiments, DK-A-221 may interact with amino acids Y56, E58, A113, M115 and Y123 of PD-L1. In other embodiments, the peptide that interacts with PD-L1 is DK-A-222. In some embodiments, DK-A-222 may interact with four amino acids of PD-L1. In particular embodiments, DK-A-222 may interact with amino acids Y56, E58, D61, and A113 of PD-L1. In some embodiments, DK-A-222 may interact with five amino acids of PD-L1. In particular embodiments, DK-A-222 may interact with amino acids Y56, E58, A113, M115 and Y123 of PD-L1.

In some embodiments, the peptide having a binding specificity for PD-L1 may have at least 80% sequence identity to SEQ ID NO.: 1. The peptide having a binding specificity for PD-L1 may have at least 80% sequence identity to SEQ ID NO.: 2. The peptide having a binding specificity for PD-L1 may have at least 85% sequence identity to SEQ ID NO.: 1. The peptide having a binding specificity for PD-L1 may have at least 85% sequence identity to SEQ ID NO.: 2. The peptide having a binding specificity for PD-L1 may have at least 90% sequence identity to SEQ ID NO.: 1. The peptide having a binding specificity for PD-L1 may have at least 90% sequence identity to SEQ ID NO.: 2. The peptide having a binding specificity for PD-L1 may have at least 95% sequence identity to SEQ ID NO.: 1. The peptide having a binding specificity for PD-L1 may have at least 95% sequence identity to SEQ ID NO.: 2. The peptide having a binding specificity for PD-L1 may have 100% sequence identity to SEQ ID NO.: 1. The peptide having a binding specificity for PD-L1 may have 100% sequence identity to SEQ ID NO.: 2.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS*. 5:151-153) with the default parameters, including default parameters for pairwise alignments.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

The terms "naturally occurring amino acid" and "naturally encoded amino acid" are used interchangeably and refer to an amino acid that is encoded by the genetic code, as well as those amino acids that are encoded by the genetic code that are modified after synthesis, e.g., hydroxyproline, γ-carboxyglutamate, and O-phosphoserine.

An "amino acid analog" is a compound that has the same basic chemical structure as a naturally occurring amino acid, i.e., an α-carbon that is bound to a hydrogen, a carboxyl group, an amino group, and an R group, e.g., homoserine, norleucine, methionine sulfoxide, or methionine methyl sulfonium. Such analogs can have modified R groups (e.g., norleucine) or modified peptide backbones, but will retain the same basic chemical structure as a naturally occurring amino acid.

The terms "non-naturally occurring amino acid" and "non-naturally encoded amino acid" are used interchangeably and refer to a compound that has the same basic chemical structure as a naturally occurring amino acid, but is not incorporated into a growing polypeptide chain by the translation complex. "Non-naturally occurring amino acid" also includes, but is not limited to, amino acids that occur by modification (e.g., posttranslational modifications) of a naturally encoded amino acid (including but not limited to, the 20 common amino acids) but are not themselves naturally incorporated into a growing polypeptide chain by the translation complex. A non-limiting list of examples of non-naturally occurring amino acids that can be inserted into a polypeptide sequence or substituted for a wild-type residue in polypeptide sequence includes β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMcCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK). Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), Nα-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminopropionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp). γ-carboxyglutamate, ε-N,N,N-trimethyllysine, €-N-acetyllysine, O-phosphoserine, N-acetylserine, N-formylmethionine, 3-methylhistidine, 5-hydroxylysine, ω-methylarginine, 4-Amino-O-Phthalic Acid (4APA), N-acetylglucosaminyl-L-serine, N-acetylglucosylaminyl-L-threonine, O-phosphotyrosine and other similar amino acids, and derivatized forms of any of those specifically listed.

A "peptide" or "protein" comprises a string of at least three amino acids linked together by peptide bonds. The terms "protein" and "peptide" may be used interchangeably. Peptide may refer to an individual peptide or a collection of peptides. Also, one or more of the amino acids in a presently disclosed imaging agent may be modified, for example, by the addition of a chemical entity, such as a carbohydrate group, a phosphate group, a farnesyl group, an isofarnesyl group, a sulphoxide group, a fatty acid group, a linker for conjugation, functionalization, or other modification, and the like. In some embodiments, other modifications may include the incorporation of D-amino acids, other molecules conjugated to the N-terminus and C-terminus, conjugation of fluorescent probes, biomolecules, such as poly(ethylene glycol), targeting ligands, and the like, retro-inversion and the like. None of the modifications should substantially interfere with the desired biological activity of the peptide.

In some embodiments of the presently disclosed imaging agent, the reporting moiety is selected from the group consisting of a chelating agent, a radiolabeled substrate, a fluorescent dye, a photoacoustic reporting molecule, and a Raman-active reporting molecule.

In some embodiments of the presently disclosed imaging agent, the reporting moiety is a chelating agent and the chelating agent is selected from the group consisting of DOTAGA (1,4,7,10-tetraazacyclododececane,1-(glutaric acid)-4,7,10-triacetic acid), DOTA (1,4,7,10-tetraazacyclododecane-1,4,7,10-tetraacetic acid), DOTASA (1,4,7,10-tetraazacyclododecane-1-(2-succinic acid)-4,7,10-triacetic acid), CB-DO2A (10-bis(carboxymethyl)-1,4,7,10-tetraazabicyclo[5.5.2]tetradecane), DEPA (7-[2-(Bis-carboxymethylamino)-ethyl]-4,10-bis-carboxymethyl-1,4,7,10-tetraazacyclododec-1-yl-acetic acid)), 3p-C-DEPA (2-[(carboxymethyl)][5-(4-nitrophenyl-1-[4,7,10-tris (carboxymethyl)-1,4,7,10-tetraazacyclododecan-1-yl] pentan-2-yl)amino]acetic acid)), TCMC (2-(4-isothiocyanotobenzyl)-1,4,7,10-tetraaza-1,4,7,10-tetra-(2-carbamonyl methyl)-cyclododecane), oxo-DO3A (1-oxa-4, 7,10-triazacyclododecane-5-S-(4-isothiocyanatobenzyl)-4, 7,10-triacetic acid), p-NH₂-Bn-Oxo-DO3A (1-Oxa-4,7,10-tetraazacyclododecane-5-S-(4-aminobenzyl)-4,7,10-triacetic acid), TE2A ((1,8-N,N'-bis-(carboxymethyl)-1,4,8,11-tetraazacyclotetradecane), MM-TE2A, DM-TE2A, CB-TE2A (4,11-bis(carboxymethyl)-1,4,8,11-tetraazabicyclo[6.6.2]hexadecane), CB-TE1A1P (4,8,11-tetraazacyclotetradecane-1-(methanephosphonic acid)-8-(methanecarboxylic acid), CB-TE2P (1,4,8,11-tetraazacyclotetradecane-1,8-bis(methanephosphonic acid), TETA (1,4,8,11-tetraazacyclotetradecane-1,4,8,11-tetraacetic acid), NOTA (1,4,7-triazacyclononane-N,N',N''-triacetic acid), NODA (1,4,7-triazacyclononane-1,4-diacetate); NODAGA (1,4,7-triazacyclononane,1-glutaric acid-4,7-acetic acid), (NOTAGA) 1,4,7-triazonane-1,4-diyl)diacetic acid DFO (Desferoxamine), NETA ([4-[2-(bis-carboxymethylamino)-ethyl]-7-carboxymethl-[1,4,7]triazonan-1-yl}-acetic acid), TACN-TM (N,N',N'', tris(2-mercaptoethyl)-1,4,7-triazacyclononane), Diamsar (1,8-Diamino-3,6,10,13,16,19-hexaazabicyclo(6,6,6)eicosane, 3,6,10,13,16,19-Hexaazabicyclo[6.6.6]eicosane-1,8-diamine), Sarar (1-N-(4-aminobenzyl)-3,6,10,13,16,19-hexaazabicyclo[6.6.6]eicosane-1,8-diamine), AmBaSar (4-((8-amino-3,6,10,13,16,19-hexaazabicyclo [6.6.6] icosane-1-ylamino) methyl) benzoic acid), and BaBaSar.

In some embodiments, the peptide, linker, reporter conjugate is prepared via click chemistry. See for example, International patent application publication no. WO/2017/027870 to Pomper et al., for Triazole Conjugated Ureas, Thioureas, Carbamates, and "Reversed" Carbamates for PSMA-Targeted Imaging Agents and Uses Thereof, published Feb. 16, 2017, and U.S. patent application publication no. 20140341804 for Homomultivalent and Heteromultivalent Inhibitors of Prostate Specific Membrane Antigen (Pmsa) and Uses Thereof, to Pomper et al., published Nov. 20, 2014, each of which is incorporated by reference in its entirety.

In particular embodiments, the chelating agent has a structure selected from the folloing:

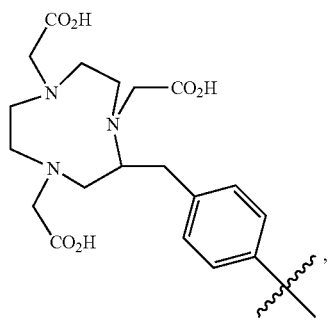

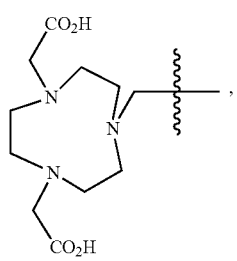

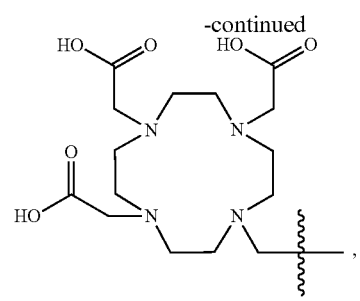

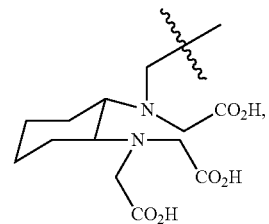

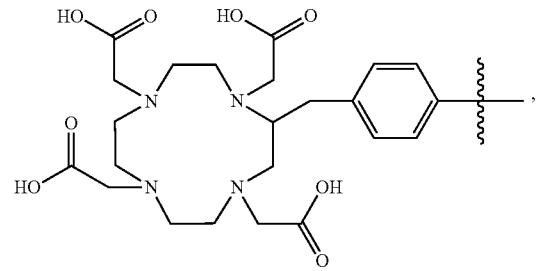

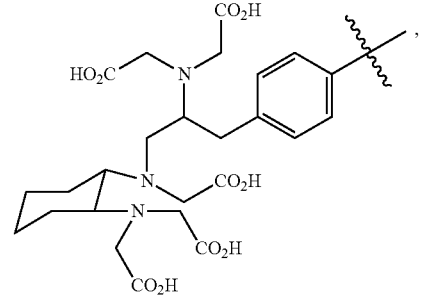

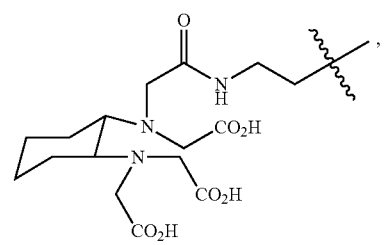

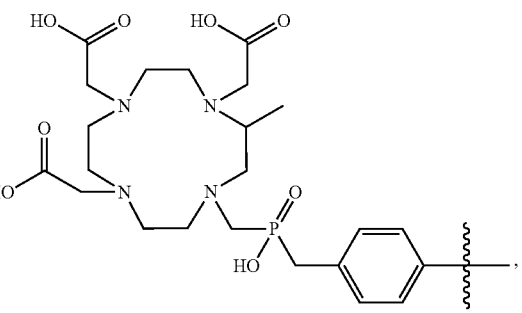

-continued
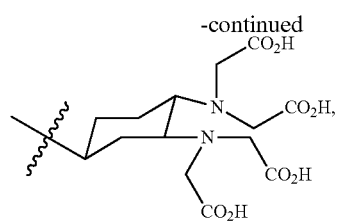,
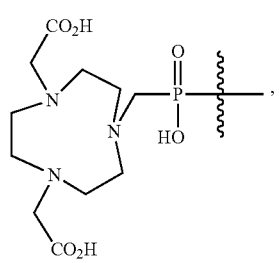,
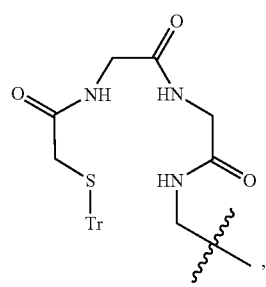,
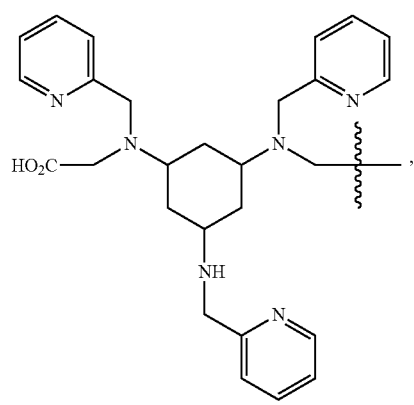,
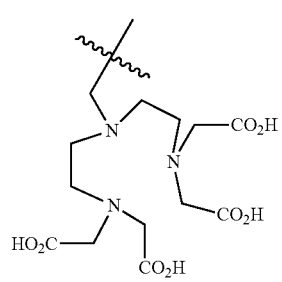,
-continued
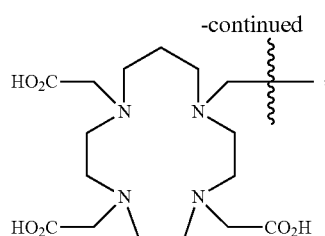,
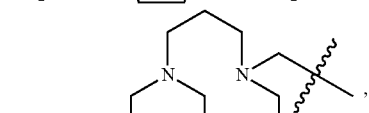,
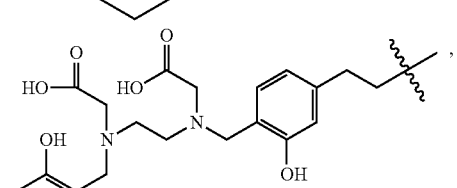,
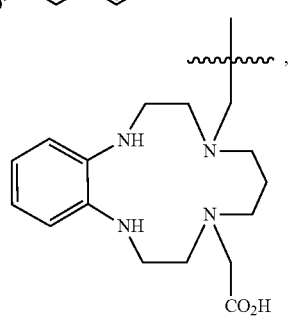,
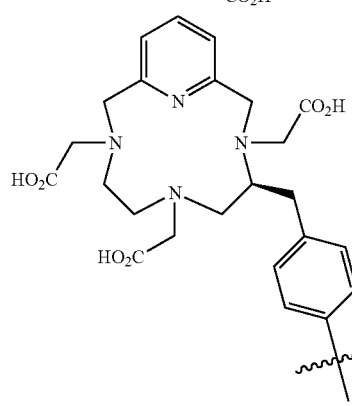,
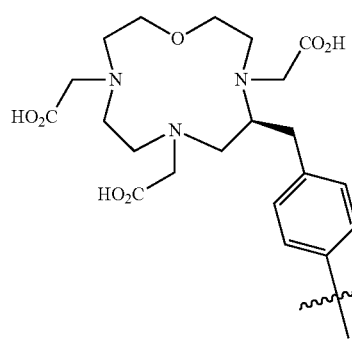 and -continued

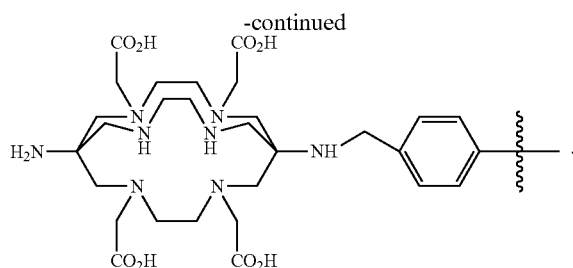

In yet more particular embodiments, the reporting moiety is a chelating agent and the chelating agent further comprises a radiometal selected from the group consisting of $^{94m}Tc$, $^{99m}Tc$, $^{111}In$, $^{67}Ga$, $^{68}Ga$, $^{86}Y$, $^{90}Y$, $^{177}Lu$, $^{186}Re$, $^{188}Re$, $^{60}Cu$, $^{61}Cu$, $^{62}Cu$, $^{64}Cu$, $^{67}Cu$, $^{55}Co$, $^{57}Co$, $^{47}Sc$, $^{225}Ac$, $^{213}Bi$, $^{212}Bi$, $^{153}Sm$, $^{166}Ho$, $^{152}Gd$, $^{82}Rb$, $^{89}Zr$, and $^{166}Dy$.

In other embodiments of the presently disclosed imaging agents, the reporting moiety is a radiolabeled substrate and the radiolabeled substrate comprises a radioisotope selected from the group consisting of $^{11}C$, $^{13}N$, $^{15}O$, $^{123}I$, $^{124}I$, $^{125}I$, $^{126}I$, $^{131}I$, $^{75}Br$, $^{76}Br$, $^{77}Br$, $^{80}Br$, $^{80m}Br$, $^{82}Br$, $^{83}Br$, and $^{211}At$. In particular embodiments, the radiolabeled substrate comprises an $^{18}F$-labeled substrate. In yet more particular embodiments, the $^{18}F$-labeled substrate is selected from the group consisting of 2-fluoro-PABA, 3-fluoro-PABA, 2-fluoro-mannitol, and N-succinimidyl-4-fluorobenzoate. In some embodiments, the substrate is labeled with $^{18}F$ using the AlF method, for example, based on the chelation of aluminum fluoride by NOTA, NODA, or any other suitable chelator known in the art. See, for example, Liu S., et al., "One-step radiosynthesis of $^{18}F$-AlF-NOTA-RGD$_2$ for tumor angiogenisis PET imaging. Eur J Nucl Med Mol Imaging. 2011, 38(9):1732-41; McBride W. J., et al., "A novel method of $^{18}F$ radiolabeling for PET. J Nucl Med. 2009; 50:991-998; McBride W. J, D'Souza C A, Sharkey R M, Sharkey R M, Karacay H, Rossi E A, Chang C-H, Goldenberg D M. Improved $^{18}F$ labeling of peptides with a fluoride-aluminum-chelate complex. Bioconjug Chem. 2010; 21:1331-1340.

In other embodiments of the presently disclosed imaging agents, the reporting moiety is a fluorescent dye and the fluorescent dye is selected from the group consisting of: carbocyanine, indocarbocyanine, oxacarbocyanine, thuicarbocyanine, merocyanine, polymethine, coumarine, rhodamine, xanthene, fluorescein, a boron-dipyrromethane (BODIPY) dye, or derivatives thereof, including, but not limited to, BODIPY FL, BODIPY R6G, BODIPY TR, BODIPY TMR, BODIPY 581/591, BODIPY 630/650, and BODIPY 650/665, Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IR800 (Dimethyl{4-[1,5,5-tris(4-dimethylaminophenyl)-2,4-pentadienylidene]-2,5-cyclohexadien-1-ylidene}ammonium perchlorate), IRDye 800CW, IRDye 800RS, IRDye 700DX, ADS780WS, ADS830WS, and ADS832WS.

In other embodiments of the presently disclosed imaging agents, the reporting moiety is a photoacoustic reporting molecule and the photoacoustic reporting molecule is selected from the group consisting of a dye or a nanoparticle. In particular embodiments, the dye comprises a fluorescent dye. In yet more particular embodiments, the fluorescent dye is selected from the group consisting of indocyanine-green (ICG), Alexa Fluor 750, Evans Blue, BHQ3, QXL680, IRDye880CW, MMPSense 680, Methylene Blue, PPCy-C8, and Cypate-C18. See Wu et al., Int. J. Mol. Sci., 15, 23616-23639 (2014).

In other embodiments, the nanoparticle is selected from the group consisting of a plasmonic nanoparticle, including, but not limited to, a gold nanosphere, a gold nanoshell, a gold nanorod, a gold nanocage, a gold nanostar, and a gold nanocluster, a quantum dot, a nanodiamond, a polypyrrole nanoparticle, a copper sulfide nanoparticle, a graphene nanosheet, an iron oxide-gold core-shell nanoparticle, a $Gd_2O_3$ nanoparticle, a single-walled carbon nanotube, a dye-loaded perfluorocarbon nanoparticle, and a superparamagnetic iron oxide nanoparticle.

In other embodiments of the presently disclosed imaging agents, the reporting moiety is a Raman-active reporting molecule and the Raman-active reporting molecule is selected from the group consisting of a single-walled carbon nanotube (SWNT) and a surface-enhanced Raman scattering (SERS) agent. In particular embodiments, the SERS agent comprises a metal (e.g., gold or silver) nanoparticle labeled with a Raman-active reporter molecule. In yet more particular embodiments, the Raman-active reporter molecule comprises a fluorescent dye. In certain embodiments, the fluorescent dye is selected from the group consisting of Cy3, Cy5, rhodamine, and a chalcogenopyrylium dye.

In other embodiments of the presently disclosed imaging agents, the linker is selected from the group consisting of:

(a)

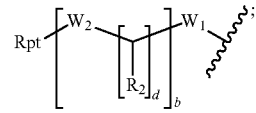

wherein: Rpt is the reporting moiety; $W_1$ is selected from the group consisting of $C_1$-$C_6$ alkylene, $C_3$-$C_6$ cycloalkylene, and arylene; $W_2$ is selected from the group consisting of —NR$^1$—(C=O)—, —NR$^1$—(C=S)—, —(C=O)—NR$^1$—, —(C=S)—NR$^1$—, and —S—, wherein each R$^1$ is independently H or $C_1$-$C_4$ alkyl; each $R_2$ is independently H or —COOR$_3$, wherein each $R_3$ is independently H, $C_1$-$C_6$ alkyl, $C_2$-$C_{12}$ aryl or $C_4$-$C_{16}$ alkylaryl; b is an integer selected from the group consisting of 0, 1, 2, and 3; d is an integer selected from the group consisting of 1, 2, 3, 4, 5, 6, 7, and 8; and wherein the wavy line indicates a point of attachment between the linker and the peptide;

(b) Rpt—X—Y—Z—W$_3$— wherein: Rpt is the reporting moiety; X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_4$; Y and $W_3$ are each independently —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond; p is 0, 1, or 2; $R_4$, for each occurrence, is halogen, hydroxy, amino, cyano, nitro, $CO_2H$, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and $R_B$, for each occurrence, is optionally substituted alkyl, optionally substituted alkoxy, optionally substituted mono or dialkylamino, optionally substituted alkylthio, optionally substituted aryl, or optionally substituted heteroaryl; or (c) an amino acid linker.

In particular embodiments, the imaging agent is a compound selected from the group consisting of formula (I), formula (II), and formula (III):

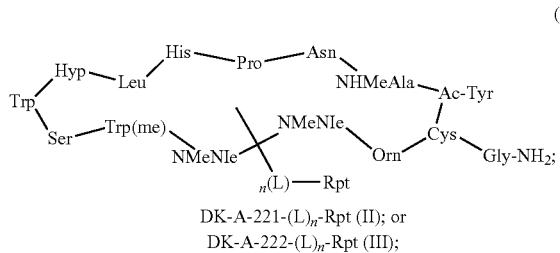

DK-A-221-(L)$_n$-Rpt (II); or
DK-A-222-(L)$_n$-Rpt (III);

wherein: n is an integer selected from the group consisting of 0 and 1; L is a linker; and Rpt is a reporting moiety; and wherein the reporting moiety or linker, when present, is attached to a primary amine group of the peptide comprising the imaging agent of formula (I), formula (II), or formula (III).

In certain embodiments, the linker, when present, is attached to an $^{13}$ornithine (Orn) primary amine group of the compound of formula (I). In particular embodiments, the reporting moiety comprises a DOTAGA chelating agent. In yet more particular embodiments, the DOTAGA chelating agent further comprises a $^{64}$Cu radiometal.

In yet more certain embodiments, the compound of formula (I) is:

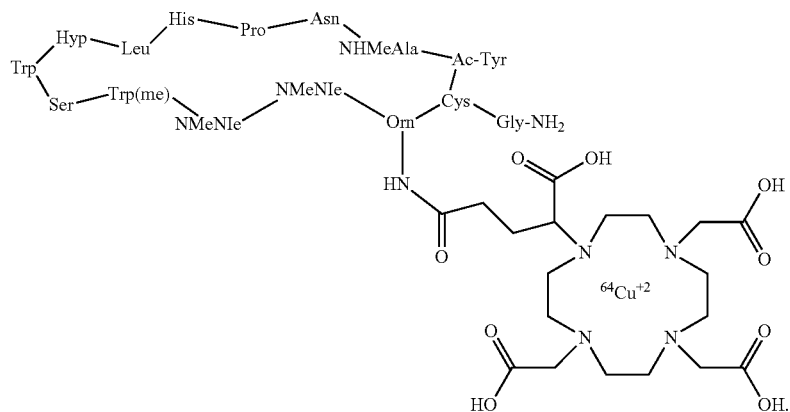

One of ordinary skill in the art would recognize upon review of the presently disclosed subject matter that a variety of combinations of chelating agents/radiometal ions are suitable for use with the presently disclosed imaging agents. Representative chelating agents are known in the art. By way of non-limiting examples, certain chelating agents and linkers are disclosed in U.S. patent application publication numbers 2015/0246144 and 2015/0104387, each of which is incorporated herein by reference in their entirety.

In some embodiments, the imaging agent is capable of detecting PD-L1 in vitro, in vivo, and/or ex vivo. In some embodiments, the imaging agent is capable of detecting PD-L1 in vivo. PD-L1 is expressed by a variety of tumors, and its over-expression is induced in tumor cells as an adaptive mechanism in response to tumor infiltrating cytotoxic T-cells (Topalian et al., 2016). One of skill will recognize that PD-L1 may comprise modifications and/or mutations and still be applicable for the presently disclosed methods, as long as it still can be detected by a presently disclosed imaging agent.

In some embodiments, the $IC_{50}$ of a presently disclosed imaging agent to inhibit PD-L1 interaction with its ligand Programmed Cell Death Protein 1 (PD-1) has a range from about 100 nM to about 1 pM. In some embodiments, the IC50 is less than 100 nM, in other embodiments, less than 10 nM, in other embodiments, less than 8 nM, in other embodiments, less than 5 nm, in other embodiments, less than 4 nm, and in other embodiments, less than 3 nM.

The term "binding affinity" is a property that describes how strongly two or more compounds associate with each other in a non-covalent relationship. Binding affinities can be characterized qualitatively, (such as "strong", "weak", "high", or "low") or quantitatively (such as measuring the $K_d$).

II. Methods of Detection Using Imaging Agents

In some embodiments, the presently disclosed subject matter provides methods for detecting an immune checkpoint protein, such as PD-L1. In some embodiments, the presently disclosed subject matter provides methods for detecting diseases, disorders, or conditions that result in over-expression of PD-L1, such as cancer, inflammation, infection, and the like.

In some embodiments, the presently disclosed subject matter provides an imaging method for detecting Programmed Death Ligand 1 (PD-L1) comprising: (a) providing an effective amount of an imaging agent comprising a conjugate of a peptide having a binding specificity for programmed death ligand 1 (PD-L1) and a reporting moiety, and optionally a linker, wherein the linker, when present connects the peptide and the reporting moiety, and when the linker is absent, the reporting moiety is attached directly to the peptide through a primary amine of an amino acid of the peptide, as described immediately hereinabove (b) contacting one or more cells or tissues with the imaging agent; and (c) making an image to detect PD-L1.

As used herein, the term "imaging" or "making an image" refers to the use of any imaging technology to visualize a detectable compound by measuring the energy emitted by the compound. In some embodiments, the term "imaging" refers to the use of any imaging technology to visualize a detectable compound after administration to a subject by measuring the energy emitted by the compound after localization of the compound following administration. In some embodiments, imaging techniques involve administering a compound to a subject that can be detected externally to the subject. In some embodiments, images are generated by virtue of differences in the spatial distribution of the imaging agents that accumulate in various locations in a subject. In some embodiments, administering an imaging agent occurs by injection.

The term "imaging agent" is intended to include a compound that is capable of being imaged by, for example, positron emission tomography (PET). As used herein, "positron emission tomography imaging" or "PET" incorporates all positron emission tomography imaging systems or equivalents and all devices capable of positron emission tomography imaging. The methods of the presently disclosed subject matter can be practiced using any such device, or variation of a PET device or equivalent, or in conjunction with any known PET methodology. See, e.g., U.S. Pat. Nos. 6,151,377; 6,072,177; 5,900,636; 5,608,221; 5,532,489; 5,272,343; 5,103,098, each of which is incorporated herein by reference. Animal imaging modalities are included, e.g., micro-PETs (Corcorde Microsystems, Inc.).

Depending on the reporting moiety, the presently disclosed imaging agents can be used in PET, single-photon emission computed tomography (SPECT), near-infrared (fluorescence), photoacoustic, and Raman imaging.

In some embodiments, the imaging includes scanning the entire subject or patient, or a particular region of the subject or patient using a detection system, and detecting the signal. The detected signal is then converted into an image. The resultant images should be read by an experienced observer, such as, for example, a physician. Generally, imaging is carried out about 1 minute to about 48 hours following administration of the imaging agent. The precise timing of the imaging will be dependent upon such factors as the clearance rate of the compound administered, as will be readily apparent to those skilled in the art. The time frame of imaging may vary based on the radionucleotide being used. In particular embodiments, imaging is carried out between about 1 minute and about 4 hours following administration, such as between 15 minutes and 30 minutes, between 30 minutes and 45 minutes, between 45 minutes and 60 minutes, between 60 minutes and 90 minutes, and between 60 minutes and 120 minutes. In some embodiments, detection of the PD-L1 occurs as soon as about 60 minutes after administration of the imaging agent to the subject. In some embodiments, the imaging may take place 24 hours post injection with a peptide labeled with Zr-89. In some embodiments, the imaging may take place 24 hours post injection with a peptide labeled with I-124.

Once an image has been obtained, one with skill in the art can determine the location of the compound. Using this information, the artisan can determine, for example, if a condition, such as an infection, inflammation, or cancer, is present, the extent of the condition, or the efficacy of the treatment that the subject is undergoing.

In some embodiments, contacting the cells or tissues with the imaging agent is performed in vitro, in vivo, or ex vivo. "Contacting" means any action that results in at least one imaging agent of the presently disclosed subject matter physically contacting at least one cell or tissue. It thus may comprise exposing the cell(s) or tissue(s) to the imaging agent in an amount sufficient to result in contact of at least one imaging agent with at least one cell or tissue. In some embodiments, the method can be practiced in vitro or ex vivo by introducing, and preferably mixing, the imaging agent and cells or tissues in a controlled environment, such as a culture dish or tube. In some embodiments, the method can be practiced in vivo, in which case contacting means exposing at least one cell or tissue in a subject to at least one imaging agent of the presently disclosed subject matter, such as administering the imaging agent to a subject via any suitable route. In some embodiments, contacting the cells or tissues with the imaging agent is performed in a subject.

The term "effective amount" of an imaging agent is the amount necessary or sufficient to provide a readable signal when imaged using the techniques described herein, e.g., positron emission tomography (PET). The effective amount can vary depending on such factors as the size and weight of the subject, the type of illness, or the particular compound. For example, the choice of the compound can affect what constitutes an "effective amount." One of ordinary skill in the art would be able to study the factors contained herein and make the determination regarding the effective amount of the compound without undue experimentation.

The subject diagnosed or treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the diagnosis or treatment of an existing disease, disorder, condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like). In some embodiments, the subject is a human, rat, mouse, cat, dog, horse, sheep, cow, monkey, avian, or amphibian.

Generally, the presently disclosed imaging agents can be administered to a subject for detection of a disease, disorder, or condition by any suitable route of administration, including orally, nasally, transmucosally, ocularly, rectally, intravaginally, or parenterally, including intravenous, intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration", "administered systemically", "peripheral administration" and "administered peripherally" as used herein mean the administration of compositions such that they enter the subject's or patient's system and, thus, are subject to metabolism and other like processes, for example, subcutaneous or intravenous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

In some embodiments, the imaging agent exhibits a target to non-target ratio of at least 3:1. In some embodiments, the term "target" refers to the cells or tissues that show over-expression of the PD-L1 protein and the term "non-target" refers to cells or tissues that do not show over-expression of the PD-L1 protein.

In some embodiments, the imaging method is used to detect a cancer. A "cancer" in a subject or patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. Cancer as used herein includes newly diagnosed or recurrent cancers, including without limitation, blastomas, carcinomas, gliomas, leukemias, lymphomas, melanomas, myeloma, and sarcomas. Cancer as used herein includes, but is not limited to, head cancer, neck cancer, head and neck cancer, lung cancer, breast cancer, such as triple negative breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, renal cancer, bladder cancer, brain cancer, and adenomas. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic.

A "tumor," as used herein, refers to all neoplastic cell growth and proliferation, whether malignant or benign, and all precancerous and cancerous cells and tissues. A "solid tumor", as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the imaging method is used to detect a solid tumor. In yet other embodiments, the imaging method is used to detect a metastatic cancer.

In some embodiments, the imaging method is used to detect an infection. Infectious disease, such as infection by any fungi or bacteria, is contemplated for detection using the presently disclosed subject matter. As used herein, the term "infection" refers to the invasion of a host organism's bodily tissues by disease-causing organisms, their multiplication, and the reaction of host tissues to these organisms and the toxins they produce. Infections include, but are not restricted to, nosocomial infections, surgical infections, and severe abdominal infections, such as peritonitis, pancreatitis, gall bladder empyema, and pleura empyema, and bone infections, such as osteomyelitis. Detection of septicemia, sepsis and septic shock, infections due to or following use of immuno-suppressant drugs, cancer chemotherapy, radiation, contaminated i.v. fluids, haemorrhagic shock, ischaemia, trauma, cancer, immuno-deficiency, virus infections, and diabetes are also contemplated. Examples of microbial infection, such as bacterial and/or fungal infection include, but are not limited to, infections due to *Mycobacterium tuberculosis, E. coli, Klebsiella* sp., *Enterobacter* sp., *Proteus* sp., *Serratia marcescens, Pseudomonas aeruginosa, Staphylococcus* spp., including *S. aureus* and coag.-negative *Staphylococcus, Enterococcus* sp., *Streptococcus pneumoniae, Haemophilus influenzae, Bacteroides* spp., *Acinetobacter* spp., *Helicobacter* spp., *Candida* sp., etc. Infections due to resistant microbes are included, for example methicillin-resistant *Staphylococcus aureus* (MRSA) and vancomycin-resistant *Enterococcus faecalis* (VRE). In some embodiments, the infection is a bacterial infection. In some embodiments, the infection is a chronic bacterial infection. In some embodiments, the bacterial infection is tuberculosis. In some embodiments, the infection is disseminated tuberculosis. In some embodiments, the infection may be hepatitis A, hepatitis B, hepatitis C, and/or human immunodeficiency virus.

In some embodiments, the imaging method is used to detect inflammation. Examples of disorders associated with inflammation include, but are not limited to, asthma, autoimmune diseases, autoinflammatory diseases, Celiac disease, diverticulitis, glomerulonephritis, hidradenitis suppurativa, hypersensitivities, inflammatory bowel diseases, interstitial cystitis, otitis, pelvic inflammatory disease, reperfusion injury, rheumatic fever, rheumatoid arthritis, sarcoidosis, transplant rejection, lupus, including, systemic lupus erythematosus, and vasculitis. In some embodiments, the inflammation is caused by rheumatoid arthritis or systemic lupus erythematosus.

PD-L1 binds to its receptor, PD-1, found on activated T cells, B cells, and myeloid cells, to modulate activation or inhibition. Accordingly, the presently disclosed imaging agents, which detect PD-L1 expression, can be used to detect immune cells, such as T cells, B cells, and myeloid cells. In some embodiments, the presently disclosed imaging agents detect immune cells in a tumor. In some embodiments, the presently disclosed imaging agents detect the distribution of immune cells systemically in a subject. In some embodiments, the imaging method is used to detect immune cell responses in infectious cells. In some embodiments, the imaging method is used to detect immune cell responses in inflammatory cells.

In some embodiments, the presently disclosed imaging method detects and/or measures a change in PD-L1 expression, such as a treatment-induced change in PD-L1 expression. Such methods can be used to ascertain the efficacy of a particular treatment method and/or to determine efficacious therapeutic dosage ranges.

III. Kits Comprising Imaging Agents

In some embodiments, the presently disclosed subject matter provides a kit for detecting Programmed Death Ligand 1 (PD-L1), the kit comprising an imaging agent comprising a conjugate of a peptide having a binding specificity for programmed death ligand 1 (PD-L1) and a reporting moiety, and optionally a linker, wherein the linker, when present connects the peptide and the reporting moiety, and when the linker is absent, the reporting moiety is attached directly to the peptide through a primary amine of an amino acid of the peptide, as described hereinabove.

Typically, the kits of the presently disclosed subject matter comprise a presently disclosed imaging agent and instructions for how to perform at least one presently disclosed method. The imaging agent is generally supplied in the kits in an amount sufficient to detect PD-L1 in at least one subject or patient at least one time. The kits can also comprise some or all of the other reagents and supplies necessary to perform at least one embodiment of the presently disclosed method.

In its simplest form, a kit according to the presently disclosed subject matter comprises a container containing at least one type of imaging agent according to the presently disclosed subject matter. In some embodiments, the kit comprises multiple containers, each of which may contain at least one imaging agent or other substances that are useful for performing one or more embodiments of the presently disclosed methods.

The container can be any material suitable for containing a presently disclosed composition or another substance useful in performing a presently disclosed method. Thus, the container may be a vial or ampule. It can be fabricated from any suitable material, such as glass, plastic, metal, or paper or a paper product. In embodiments, it is a glass or plastic ampule or vial that can be sealed, such as by a stopper, a stopper and crimp seal, or a plastic or metal cap. The amount of imaging agent contained in the container can be selected by one of skill in the art without undue experimentation based on numerous parameters that are relevant according to the presently disclosed subject matter.

In embodiments, the container is provided as a component of a larger unit that typically comprises packaging materials (referred to below as a kit for simplicity purposes). The presently disclosed kit can include suitable packaging and instructions and/or other information relating to the use of the compositions. Typically, the kit is fabricated from a sturdy material, such as cardboard and plastic, and can contain the instructions or other information printed directly on it. The kit can comprise multiple containers containing the composition of the invention. In such kits, each container can be the same size, and contain the same amount of composition, as each other container, or different containers may be different sizes and/or contain different amounts of compositions or compositions having different constituents. One of skill in the art will immediately appreciate that numerous different configurations of container sizes and contents are envisioned by this invention, and thus not all permutations need be specifically recited herein.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Rapid Tumor PD-L1 Detection with PET Using a Highly Specific Peptide 1.1 Background. Increased PD-L1 in the tumor microenvironment (TME) causes immune suppression by deactivation of immune infiltrates via binding to programmed cell death protein 1 (PD-1) receptor, expressed by active immune infiltrates (Okazaki et al., 2007, and Topalian et al., 2015). PD-L1 expression on tumor cells and in the TME is considered a potential biomarker for patient stratification and therapeutic monitoring (Herbst et al., 2014). A complementary diagnostic test based on PD-L1 IHC was recently approved by the U.S. Food and Drug Administration, suggesting that PD-L1 may be a suitable target for imaging in vivo (Roach et al., 2016).

Currently, immunohistochemical (IHC) detection is the best-studied predictive biomarker for therapeutic monitoring of PD-L1/PD-1 targeted therapies, but this approach and its available FDA-approved diagnostic IHC tests for PD-L1 have significant limitations, Roach et al., 2016; Mansfield and Dong, 2016; and Phillips et al., 2015, hampered by inconsistent definitions of antigen-positivity, discordant detection antibodies, insufficient inter-assay agreement, and intra- and inter-tumoral heterogeneities that compromise accuracy and reliability, and thus therapeutic decision-making. Also, tissue samples acquired by biopsy for testing are typically very limited, and may be needed for molecular profiling to identify targetable oncogenic mutations in other pathways (e.g., epidermal growth factor receptor (EGFR), anaplastic lymphoma kinase, DNA repair genes) that confer sensitivity or resistance to existing therapies. Such precious samples make it often impractical to perform multiple PD-L1 assessments for reliable representation of PD-L1 expression. It is anticipated that novel PET imaging agents that enable non-invasive assessment of PD-L1 expression levels, dynamics and distribution, and do so within the standard clinical workflow of imaging within 60 min of administration, will overcome the shortcomings of available (IHC-based) methods for evaluating PD-L1 expression status.

The dynamic nature of the tumor immune microenvironment provides rationale for development of PET tracers that allow for rapid evaluation of TME. In this regard, low molecular weight, peptide-based PET tracers are desirable candidates for clinical application due to their fast clearance and synthetic tractability (Reubi et al., 2008; Sun et al., 2016). Peptide-based PET tracers targeting somatostatin receptors and chemokine receptor 4 (CXCR4) produce high target-to-non-target ratios in patients (Herrmann et al., 2016; Gourni et al., 2011).

Recently, peptides that specifically bind to PD-L1 have been reported (see International PCT patent application publication no. WO2016039749 to Miller, et al., for Macrocyclic Inhibitors of the PD-1/PD-L1 and CD80 (B7-1)/PD-L1 Protein/Protein Interactions, published Mar. 17, 2016; International PCT patent application publication no. WO 2016/100285 to Mapelli, et al., for Immunomodulators, published Jun. 23, 2016; International PCT patent application publication no. WO 2016/100608 to Sun, et al. for Immunomodulators, published Jun. 23, 2016; International PCT patent application publication no. WO 2016/126646 to Miller et al., for Immunomodulators, published Aug. 11, 2016, each of which is incorporated herein in their entirety); however, their potential to detect PD-L1 expression in vivo has not been established. It was hypothesized that those PD-L1 binding peptides have the potential to detect PD-L1 expression in tumors rapidly and with high specificity. To test this hypothesis, a peptide, WL12, was selected from a reported peptide library that is most suitable for conjugation and possesses a single primary amine and its binding mode to PD-L1 was assessed. A DOTAGA chelator was conjugated to WL12 for radiolabeling with $^{64}Cu$ to generate [$^{64}Cu$]WL12 (Eisenwiener et al., 2000), the binding affinities of the peptide derivatives to PD-L1 were assessed, and the in vitro uptake of [$^{64}Cu$]WL12 in cell lines with variable PD-L1 expression was determined. As proof-of-concept, the ability of the [$^{64}Cu$]WL12 to detect PD-L1 expression in vivo by PET imaging was evaluated in NSG mice harboring Chinese hamster ovary (CHO) tumors with constitutive human PD-L1 expression (hPD-L1) and isogenic negative control tumors (CHO). Tissue distribution and target specificity of [$^{64}Cu$]WL12 were confirmed by ex vivo biodistribution and blocking studies.

1.2 Results and Discussion 1.2.1 WL12 binds PD-L1 in a similar mode to that of PD-1. To assess the binding mode of WL12 to PD-L1, the co-crystal structure of human PD-L1 bound to PD-1 (PDB ID: 4ZQK) (Zak et al., 2015) to dock WL12 in the place of PD-1 was used. Given the structural complexity of the macrocycle, WL12, we first performed a conformational search and the conformers were docked into the PD-1 binding site on PD-L1 using Glide (Friesner et al., 2004; Halgren et al., 2004). WL12 forms a beta sheet like structure with two hydrogen bonds made between the backbone of the two macrocycle strands (FIG. 1B). This conformation is supported by circular dichroism experiments (FIG. 2). An overlay of the structure of PD-1 with the bound WL12 reveals the similarities in binding mode between the two. The two beta strands of PD-1 that form the binding interface with PD-L1 overlap with the pseudo-strands of WL12 (FIG. 1C). The L-leucine of WL12 inserts into the same small, hydrophobic pocket as Ile134 of PD-1, and one of the two norleucine residues ligns with Ile126 of PD-1. In addition to these hydrophobic interactions, a number of hydrogen bonds are present between WL12 and PD-L1. The carboxamide of the asparagine on WL12 forms a hydrogen bond with Tyr123, the glycine amide forms hydrogen bonds with the backbone of Gly120, and the serine hydroxyl interacts with Gln66. The ornithine residue is exposed and does not participate in binding with PD-L1. Without wishing to be bound to any one particular theory, this suggests that conjugation of a suitable label via amine-coupling methods would not disrupt WL12 binding to PD-L1.

1.2.2 [$^{64}Cu$]WL12 shows PD-L1-specific cellular uptake in vitro. The $^{13}$ornithine (Orn) primary amine was utilized to conjugate DOTAGA, which was then used to prepare a non-radioactive $Cu^{2+}$ analog (WL12-Cu) and to radiolabel with $^{64}Cu$. The resulting WL12D and the corresponding WL12-Cu were purified by HPLC, characterized by mass spectrometry (FIG. 2, FIG. 3, FIG. 4, FIG. 5, FIG. 6, and FIG. 7), and subjected to in vitro evaluation. To assess the half-maximal inhibitory concentration ($IC_{50}$) of WL12 and its derivatives to inhibit PD-L1 interaction with PD-1, a previously described in vitro assay that relies on fluorescence resonance energy transfer (Woodard et al., 2014) was optimized. $IC_{50}$ values of 22, 23, and 2.9 nM were observed for WL12, WL12D, and WL12-Cu, respectively (FIG. 8A, FIG. 9, FIG. 10 and Table 1 below). These data indicate that WL12 retains high binding affinity to PD-L1 upon modification of $^{13}$Orn side chain with DOTAGA and chelation to $Cu^{2+}$.

TABLE 1

WL12-unmodified peptide; WL12D-peptide conjugated with DOTAGA, WL-$Cu^{2+}$-copper complex of WL12D. 95% CI-95% confidence intervals.

| Compound | $IC_{50}$ [nM] | 95% CI [nM] | $K_i$ [nM] | 95% CI [nM] |
|---|---|---|---|---|
| WL12 | 20.3 | 11.4-46.1 | 1.1 | 5.3-21.5 |
| WL12D | 22.2 | 14.7-33.7 | 10.4 | 6.8-15.7 |
| WL-$Cu^{2+}$ | 2.97 | 2.17-4.5 | 1.38 | 1.01-1.89 |

To demonstrate PD-L1 specificity and cell uptake, [$^{64}$Cu]WL12 was generated with high specific radioactivity (1.9±0.1 mCi/µg) and radiochemical purity (>95%) (FIG. 11 and FIG. 12). hPD-L1 cells incubated with [$^{64}$Cu]WL12 for 1 h showed >50% uptake of the incubated dose and a 43-fold increase in bound radioactivity compared to the negative control CHO cells (FIG. 8C). The binding specificity was then tested by incubating hPD-L1 cells with [$^{64}$Cu]WL12 alone or in the presence of a 1 µM blocking dose of WL12. A >95% reduction in bound [$^{64}$Cu]WL12 was observed in the presence of the peptide indicating that [$^{64}$Cu]WL12 binding to PD-L1 is specific (FIG. 8C). The ability of [$^{64}$Cu]WL12 to detect endogenous PD-L1 expression was further tested in two triple negative breast cancer (TNBC) cell lines, MDAMB231 and SUM149, which show high and low PD-L1 expression respectively (FIG. 8B). Two-fold higher uptake of radioactivity in MDAMB231 cells compared to SUM149 cells further confirmed the specificity of [$^{64}$Cu]WL12 for PD-L1 (FIG. 8C). Flow cytometry analysis for PD-L1 expression demonstrated the mean fluorescence intensity values in the following order: hPD-L1>MDAMB231>SUM149>CHO, which correlated with the uptake of radioactivity (r=0.9977, FIG. 13 and FIG. 14). Collectively, those results demonstrate that [$^{64}$Cu]WL12 binds cancer cells in vitro in a PD-L1 expression-dependent manner.

1.2.3 [$^{64}$Cu]WL12 specifically accumulates in tumors with high PD-L1 expression. To gain insight into the in vivo specificity and distribution of [$^{64}$Cu]WL12, PET-CT imaging studies were performed in mice harboring hPD-L1 and CHO tumors (n=4). PET imaging studies showed robust uptake of [$^{64}$Cu]WL12 in hPD-L1 tumors. The increased uptake in hPD-L1 tumors could be observed as early as 10 min and retained through 24 h post-injection (FIG. 15A and FIG. 16), with PD-L1 expression confirmed by IHC (FIG. 15B). In addition to tumors, high uptake also was observed in kidneys and liver. To confirm the PET imaging observations, biodistribution studies were performed at 1 and 2 h after the injection of [$^{64}$Cu]WL12 (n=3 and n=5, respectively). Considering the rapid uptake observed in PD-L1-positive tumors, it was thought that biodistribution at 1 and 2 h would be more informative for the development of an $^{18}$F-labeled analog. Consistent with the imaging studies, hPD-L1 tumors demonstrated radioactivity uptake in percentage of injected dose/g (% ID/g) values of 14.9±0.8 at 1 h. By contrast, control CHO tumor uptake was 4.0±0.6% ID/g (FIG. 17). Uptake in the kidneys and liver also was relatively high, with uptake values of 34.4±3.1 and 24.2±2.5% ID/g, respectively. The tumor-to-muscle and tumor-to-blood ratios for hPD-L1 tumors were 25.6±1.9 and 4.7±1.2, respectively, consistent with the ability of [$^{64}$Cu]WL12 to provide PD-L1 specific images with high signal-to-noise ratios (FIG. 15A and FIG. 15B).

Biodistribution studies performed at 2 h showed a similar profile with a trend toward decreased radioactivity in kidneys, liver and the tumor (FIG. 17). To demonstrate in vivo specificity, [$^{64}$Cu]WL12 was co-injected with excess WL12 (50 µg, 2 mg/kg) and performed biodistribution studies at 2 h. A >75% reduction in % ID/g values in hPD-L1 tumors (P<0.0001) was observed and no significant difference in control CHO tumors was observed. Kidneys also showed reduced uptake. No significant differences in uptake of radioactivity were observed in other tissues. Increased uptake in the liver, a trend often observed with $^{64}$Cu-based imaging agents (Anderson et al., 2009), could be due to dissociation of $Cu^{2+}$ from the chelator and subsequent transchelation to plasma proteins, such as albumin and ceruloplasmin (Smith-Jones et al., 1991; Wadas et al., 2007; and Boswell et al., 2004). Increased kidney uptake also suggests predominantly renal clearance of the peptide. Low uptake observed in spleen, thymus and brown fat, tissues that are known to express PD-L1 and reported to show increased radiolabeled antibody uptake (Chatterjee et al., 2016; Hettich et al., 2016; and Josefsson et al., 2016), suggests that [$^{64}$Cu]WL12 has very low or no affinity for mouse PD-L1. Further supporting the [$^{64}$Cu]WL12 specificity to human PD-L1, no significant differences in uptake were noted in those tissues between control and blocking dose groups, except for kidney. The imaging and biodistribution studies collectively demonstrate that [$^{64}$Cu]WL12 binds rapidly and specifically to human PD-L1.

1.2.4 CD results. To evaluate secondary structure of WL12 in aqueous and membrane mimicking solutions, CD spectroscopy was run in combinations of water, DPC, and SDS. As presented in FIG. 2, Trp residues have significant impact on the CD spectra of WL12 peptide in the region of 220-240 nm. In surfactant-free solution a minimum at ca. 220 nm and a positive shoulder at ca. 230 nm are observed. Upon addition of surfactants, both bands are slightly red-shifted and an increase in the intensity of the latter is noticed. These bands are attributable to Trp-Trp coupling. Both Trp chromophores are in close proximity and they behave as a single absorbing unit. Consequently, their excited states interact and the excited states of the dimeric system are delocalized over both monomers. This phenomenon referred to as the exciton effect, gives rise to a splitting of the excited state into two components, one of which arises from in-phase combination of the two monomeric excitations and the other from the out-of-phase combination. (Grishina 1994, and Kelly 2000).

The CD spectra of unordered peptides are typically characterized by a single band below 200 nm, whereas α-helix presents two negative bands at 208 and 222 nm with one positive band at 192 nm, and β-sheet structures usually show a negative band at 217 nm with a positive one at 195 nm. Therefore, strong negative band at ~205 nm and strong positive band at 190 nm on the CD spectra of WL12 peptide may suggest a mixture a random coil conformation and more ordered structure. Deconvolution of the CD spectra indicates high β-sheet content (~40%) under all the measurement conditions. Nevertheless, the strong contribution of Trp chromophores to the far-UV CD spectra of WL12 affects the precision of quantitative analysis of the secondary structure content and the results should be interpreted with a caution.

1.3 Summary. In summary, rapid tumor PD-L1 detection and PD-L1 selectivity were demonstrated in vitro and in vivo with PET using a highly specific PD-L1 binding peptide [$^{64}$Cu]WL12. The pharmacokinetics and biodistribution of

[$^{64}$Cu]WL12 indicate that PD-L1 detection is feasible to fit within the standard clinical workflow of imaging patients within 60 min of radiotracer administration. Rapid and non-invasive detection of PD-L1 expression in all malignant lesions in entirety provides unprecedented opportunities to stratify patients for immune modulation therapies.

1.4 Materials and Methods 1.4.1 Materials: PD-L1 binding peptide, WL12, was custom synthesized by CPC Scientific (Sunnyvale, Calif.) with >95% purity. All other chemicals were purchased from Sigma-Aldrich or Fisher Scientific unless otherwise specified. 2,2′,2″-(10-(2,6-dioxotetrahydro-2H-pyran-3-yl)-1,4,7,10-tetraazacyclododecane-1,4,7-triyl)triacetic acid (DOTAGA anhydrate) and [$^{64}$Cu]Cl$_2$ were purchased from CheMatech Macrocycle Design Technologies (catalog #C109; Dijon, France) and The University of Wisconsin, respectively. All cell culture related reagents were purchased from Invitrogen, unless otherwise specified. Polyclonal anti-human IgG-Eu$^{3+}$Cryptate (catalog #61HFCKLA) and XL665-conjugated mouse monoclonal anti-6Histidine antibody (catalog #61HISXLA) were purchased from Cisbio Assays (Bedford, Mass.). Recombinant Human PD-1 Fc chimera Protein (catalog #1086-PD-050) and recombinant human PD-L1(B7-H1)-His-tag protein (catalog #9049-B7) were obtained from R&D systems (Minneapolis, Minn.).

1.4.2 Docking studies: To perform the docking of WL12 to PD-L1, the crystal structure of human PD-1 bound to PD-L1 (PDB ID: 4ZQK) was used as a template. The model was first prepared using the Protein Preparation Wizard in Maestro (Schrödinger Release 2016-2: Maestro, version 10.6, Schrödinger, LLC, New York, N.Y., 2016) (Sastry et al., 2013). This involves the assignment of bond orders and formal charges, the addition of hydrogen atoms and the addition of missing side-chains. The hydrogen bonding network within the protein is optimized (including the reorientation of thiol and hydroxyl groups, sampling Asn, Gln and His side chains, and the prediction of the protonation states of His, Asp and Glu), followed by a brief minimization. The structure of PD-1 was removed. A conformational search was performed on the structure of WL12 using Prime Conformational Search (Schrödinger Release 2016-2: Prime, version 4.4, Schrödinger, LLC, New York, N.Y., 2016). The 100 lowest energy conformers were selected for docking experiments. Docking was performed with Glide (Schrödinger Release 2016-2: Glide, version 7.1, Schrödinger, LLC, New York, N.Y., 2016) using default settings and input ring conformations (Friesner et al., 2004, Halgren et al., 2004). Software used for these computations was curated by SBGrid (Morin et al., 2013).

1.4.3 Circular dichroism (CD) measurements: CD spectra of the peptide in the aqueous surfactant-free and in the aqueous micellar solutions of dodecylphosphatidylcholine (DPC), sodium dodecylsulphate (SDS) and mixed DPC:SDS micelles at molar ratio 5:1 were acquired using a Jasco J-815 spectropolarimeter (Jasco, Easton, Md.). All measurements were done using 0.15 mg/mL peptide solutions at 25° C. Experiments were carried out over the 185-260 nm range and performed in triplicate to increase signal-to-noise ratios. Final spectra were corrected by background subtraction and analyzed as mean residue molar ellipticity, MRME (degree× cm$^2$×dmol$^{-1}$) vs. wavelength $\lambda$ (nm). The content of the secondary structure was calculated from the spectra using a CONTIN method (Sreerama et al., 2000).

1.4.4 Synthesis of WL12-DOTAGA (WL12D): Three mg of the peptide (1.5 µmol) was dissolved in 0.5 mL of DMF and mixed with 3.7 mg of DOTAGA anhydride (7.51 µmol in 0.5 mL of DMF) and 20 µL of diisopropylethylamine (DIPEA). Reaction mixture was stirred for 2 h at room temperature and product was purified on a reversed phase high performance liquid chromatography (RP-HPLC) system (Varian ProStar) with an Agilent Technology 1260 Infinity photodiode array detector (Agilent Technologies, Wilmington, Del.) using a semi-preparative C-18 Luna column (5 mm, 10×250 mm Phenomenex, Torrance, Calif.) and a gradient elution starting with 98% H$_2$O (0.1% TFA) and 2% MeOH (0.1% TFA) reaching 100% of MeOH in 60 min at a flow rate of 4 mL/min. The desired WL12D was collected at 44.5 min, evaporated, dissolved in deionized water and lyophilized yielding 3.1 mg (1.3 µmol) of the product as a white powder (yield: 82.9%, FIG. 2). The resulting conjugate, solubilized in H$_2$O-MeOH 50% (v/v) with 0.1% of formic acid, was analyzed by electron spray ionization mass spectrometry (ESI MS, Esquire 3000 Plus spectrometer, Bruker Daltonics, Billerica, Mass.) (FIG. 4). Theoretical chemical formula: $C_{91}H_{128}N_{22}O_{20}S_2$. Observed ESI-MS m/z: 2340.9–(M+1)$^{+1}$, 1171.1–(M+2)$^{+2}$/2 and 781.1–(M+2)$^{+3}$/3. (Expected: 2340.65)

1.4.5 Preparation of WL12-Cu$^{2+}$ complex: 1.5 mg of WL12D (0.64 µmol) was dissolved in 200 µL of sodium acetate (0.1M, pH=4.5 adjusted with glacial acetic acid) and 55 µL of 0.02M CuCl$_2$ aqueous solution (1.1 µmol) was added. Resulting reaction mixture was incubated at 65° C. for 30 min and purified by RP-HPLC as described for WL12D (FIG. 5), lyophilized and the resulting light blue powder was analyzed by ESI MS (FIG. 6). WL12-Cu$^{2+}$ complex was then used to optimize RP-HPLC conditions, as a standard for radiolabeling, and for PD-L1 and PD-1 competition binding assay (FIG. 7). Theoretical chemical formula: $C_{110}H_{156}N_{26}O_{29}S$. Observed ESI-MS m/z: 2402.6–(M+1)$^{+1}$, 1201.9–(M+2)$^{+2}$/2 (Expected: 2402.18)

1.4.6 PD-L1 and PD-1 binding inhibition assay: A competitive inhibition assay for PD-L1 binding to PD-1 was optimized from a previously described fluorescence resonance energy transfer (FRET)-based assay in discussion with Cisbio (Woodard et al., 2014). All binding/inhibition assays were performed in 21 µL of FRET assay buffer (dPBS, bovine serum albumin (0.1%, w/v), Tween-20 (0.05% v/v) and sodium fluoride (400 mM)). Assay conditions were first optimized for PD-1 and PD-L1 concentrations. PD-1-Ig at final concentration of 10 nM, 20 nM and 40 nM was incubated for 15 min with PD-L1-His-tag at final concentrations ranging from 0.65 to 320 nM (each concentration in triplicates), followed by addition of 10 µL FRET buffer containing anti-human IgG-Eu$^{3+}$ cryptate (IgG-Eu, final concentration 2 nM) and anti-6HIS-XL665 monoclonal antibody (anti-6HIS-XL665, final concentration 40 nM). After incubation at room temperature for one hour, 1 µL of NaF assay buffer solution was added (final concentration, 400 mM) and plate was read using a Perkin Elmer Victor3 1420 multi-label counter (Perkin Elmer, Waltham, Mass.).

For competitive inhibition assay, inhibitors (WL12, WL12D and WL12-Cu$^{2+}$, range: 1 pM to 1 mM) were pre-incubated with PD-L1-His-tag (80 nM final) in 10 µL assay buffer for 15 min, followed by addition of 5 µL of assay buffer containing PD-1-Ig (final concentration 20 nM) and incubated for 15 min. Then 5 µL of assay buffer with IgG-Eu (final concentration 2 nM) and anti-6HIS-XL665 (final concentration 40 nM) was added. After 1 h incubation at room temperature 1 µL of NaF was added (final concentration 400 mM) and plate was read on a Perkin Elmer Victor3 1420 multi-label counter. IC$_{50}$ and K$_i$ values were calculated by fitting the data to a sigmoidal dose response curve and the Cheng-Prusoff equation with derived $K_D$=70 nM for PD-L1 at a concentration of 80 nM. All experiments were performed in triplicate and repeated three times.

1.4.7. Generation of [$^{64}$Cu]WL12: $^{64}$CuCl$_2$, purchased from University of Wisconsin, was evaporated to a small volume and transformed into $^{64}$Cu(OAc)$_2$ by titrating with 0.1 M sodium acetate solution. For radiolabeling, approximately 10 μg of WL12D peptide conjugate (4.27 nmol) in 100 μL of sodium acetate was mixed with ~185 MBq (~5 mCi) of $^{64}$Cu(OAc)$_2$ and incubated at 65° C. for 30 min. Resulting radiotracer was purified on a C-18 (Luna, 5 μm, 10×250 mm; Phenomenex) semi-preparative column using a Varian ProStar system equipped with a radioactive single-channel radiation detector (model 105S; Bioscan, Poway, Calif.) and a Varian ProStar UV absorbance detector set to 280 nm. Gradient elution starting with 98% H$_2$O (0.1% TFA) and 2% MeOH (0.1% TFA) reaching 90% MeOH over 70 min at flow rate of 5 mL/min was applied. [$^{64}$Cu]WL12 was collected at 56.2 min (retention time for unlabeled peptide: 53.6 min) evaporated, diluted with saline containing 5% DMSO and two drops of Tween 20, used for in vitro and in vivo evaluation. [$^{64}$Cu]WL12 was obtained in 52.09+– 6.3% yield with a specific activity of 1.9±0.11 mCi/μg.

1.4.7. Cell lines: Chinese hamster ovary cell line CHO-K1 (henceforth referred to as CHO) and triple negative breast cancer (TNBC) cell line MDAMB231 were purchased from the American Type Culture Collection (ATCC, Manassas, Va.) and passaged for fewer than 3 months after which new cultures were initiated from vials of frozen cells. The SUM149 cell line was kindly provided by Dr. Stephen P. Ethier, Medical University of South Carolina, and authenticated by STR profiling at the Johns Hopkins genetic resources facility. SUM149 cells were maintained in Ham's F-12 medium with 5% FBS, 1% P/S and 5 μg/mL insulin, and 0.5 μg/mL hydrocortisone. All other cell lines were cultured in ATCC recommended media in an incubator at 37° C. in an atmosphere containing 5% CO$_2$. CHO cell line stably expressing human PD-L1 (henceforth referred to as hPD-L1) was generated in our laboratory (Chatterjee et al., 2016) and maintained in F-12K medium with 10% FBS, 1% P/S and 2 mg/mL G418.

1.4.8. Flow cytometry: Cells in suspension were harvested by centrifugation and adherent cells were detached using enzyme-free, PBS-based cell dissociation buffer (Thermo Fisher Scientific, Waltham, Mass.). The harvested cells were washed twice with flow cytometry buffer (1×PBS with 2 mM EDTA and 0.5% FBS). Cells were stained with anti-human PD-L1 antibody conjugated with phycoerythrin (denoted as BD-MIH-PE, clone #MIH1, catalog #557924, Becton Dickinson, Franklin Lakes, N.J.) according to the manufacturer's protocol and were analyzed on a FACSCalibur flow cytometer (Becton Dickinson). At least 20,000 events were recorded.

1.4.9. In vitro binding: In vitro binding of [$^{64}$Cu]WL12 to hPD-L1, CHO, MDAMB231 and SUM149 cells was determined by incubating 1 μCi of the radiotracer with 1×10$^6$ cells for 1 h at 37° C. After incubation, cells were washed three times with cold PBS prior to counting on an automated gamma counter (1282 Compugamma CS, Pharmacia/LKB-Nuclear, Inc., Gaithersburg, Md.). To demonstrate PD-L1 specific binding of [$^{64}$Cu]WL12, PD-L1 blocking was performed with 1 μM of either WL12 peptide or humanized anti-PD-L1 antibody atezolizumab. Mean fluorescence intensity values were correlated with % incubated dose (% ID) uptake. All the cell uptake studies were performed in triplicate for each cell line and repeated three times.

1.4.10. Animal Models: Animal studies were performed according to the protocols approved by the JHU Animal Care and Use Committee (ACUC). Six-to-eight week old, female, non-obese diabetic severe-combined immunodeficient gamma (NSG) mice were obtained from the JHU Immune Compromised Animal Core. Mice were implanted subcutaneously in opposite sides of the upper flanks with 10×10$^6$ of CHO-PDL1 and CHO cells. Mice were used for imaging orbiodistribution experiments when the tumors reached a volume of 200-300 mm$^3$.

1.4.11. PET-CT imaging of mouse xenografts: Mice were injected with 150 μCi of [$^{64}$Cu]WL12 in 200 μL of saline intravenously (n=3), anesthetized under 3% isofluorane prior to being placed on the scanner. Mice were maintained at 1% Isofluorane levels during imaging. PET images were acquired in two bed positions at 10 min/bed in an ARGUS small-animal PET/CT scanner (Sedecal, Madrid, Spain). A CT scan (512 projections) was performed at the end of each PET scan for anatomical co-registration. PET data were reconstructed using the two-dimensional ordered subsets-expectation maximization algorithm (2D-OSEM) and corrected for dead time and radioactive decay. The % ID per cc values were calculated based on a calibration factor obtained from a known radioactive quantity. Final data visualization and image generation was accomplished using Amira® (FEI, Hillsboro, Oreg.).

1.4.12. Ex vivo biodistribution: Mice harboring hPD-L1 and CHO tumors with high and low PD-L1 expression (n=5), respectively were injected intravenously with 40 μCi of [$^{64}$Cu]WL12. Blood, tumors, and selected tissues were harvested, weighed and counted in an automated gamma counter (Perkin Elmer—2480 Automatic Gamma counter—Wizard2 3" Wallac) at 1 h and 2 h after [$^{64}$Cu]WL12 injection. For the blocking study, mice were co-injected with 2 mg/kg (50 μg) of unmodified peptide with the radiotracer. The percentage of injected dose per gram of tissue (% ID/g) values were calculated based on signal decay correction and normalization to external [$^{64}$Cu] standards, which were measured in triplicate. Biodistribution data shown is mean±the standard error of the mean (SEM).

1.4.13. Data analysis: Statistical analysis was performed using an unpaired two tailed t-test using a Prism 6 Software (GraphPad Software, La Jolla, Calif.). P-values<0.05 were considered to be significant and the comparative reference was cell line or tumor with low PD-L1 expression. Flow cytometry data was analyzed using FlowJo software (Tree Star, Ashland, Oreg.). IC$_{50}$ and K$_i$ values were calculated by using Prism 6 software (GraphPad).

Example 2

PD-L1 Directed PET to PD-L1 Targeted Drug Development 2.1 Overview. Cancer immunotherapy (CIT) is improving patient survival by producing durable responses in a variety of malignancies. However, nearly 70% of the patients treated with immune checkpoint targeted therapies do not respond to monotherapy (Lipson, et al., 2015; Topalian, et al., 2015). There is an unmet need to identify determinants of response for precision immunotherapy. Checkpoint combination therapies have prolonged survival, but often at the expense of increased immune related adverse events (irAE), suggesting that increased knowledge on combination strategies is needed to mitigate toxicity (Marrone, et al., 2016). Focused research to identify new biomarkers for immune checkpoint therapies and their combinations to enhance their breadth and durability and to reduce the irAEs is badly needed. Accordingly, one aspect of the presently disclosed subject matter is to develop strategies to use PD-L1 based PET imaging in development and evaluation of PD-L1 targeted therapeutic drugs. Unlike the current strategies that rely on plasma or tissue (biopsy)-based biomarkers that are invasive and impractical in advanced stage patients proposed inventions will establish the dose vs. occupancy relationships of PD-L1 targeted therapeutics (antibodies, peptides, small molecules) in the tumor in relevant in vivo models using PD-L1 PET imaging.

2.1.1. Advances enabled by PET-based quantification of PD-L1 dynamics: It has been recently discovered that accumulation of the PD-L1-targeted therapeutic AtzMab and its mouse chimera (PRO) within NSCLC, TNBC and colon tumors is not entirely PD-L1 expression-dependent, as H2444 NSCLC xenografts that have high PD-L1 expression accumulated substantially lower amounts of radiolabeled AtzMab vs. those seen in breast cancer xenografts with low PD-L1 expression, as detected by IHC and flow cytometry (Chatterjee, et al., 2016). Similarly, in syngeneic mouse tumor models, systemically injected radiolabeled PRO was primarily associated with tumor vasculature, and showed little or no diffusion into tumor parenchyma in tumors (Deng, et al., 2016). Such findings may be attributable to pathophysiological features including elevated interstitial pressure within tumors (Baxter, et al., 1989; Baxter, et al., 1990), that preclude accumulation of therapeutic agents within the tumors, which is a significant contributor to therapeutic resistance (Goel, et al., 2011). Also, such effects might potentially impede access to tumor cells of PD-L1-targeting therapeutic agents, which primarily act upon tumor cells and tumor immune infiltrates. Therefore, peptides such as WL12/[$^{18}$F]WL12 or similar radiolabeled peptides may penetrate tumor tissue to reach target cells more effectively and efficiently than antibodies, owing to their much smaller molecular sizes. By using appropriate analyses and corrections, [$^{18}$F]WL12 measurements or measurement made using similar radiolabeled peptides might therefore aid in identifying/optimizing therapeutic mAb doses needed to achieve desired occupancy within tumor tissue, at the targeted tumor cells.

Therefore, PD-L1-directed PET has been applied to PD-L1-targeted drug development. To assess its potential value, in an innovative strategy [$^{64}$Cu]WL12 has been used to evaluate and compare the tumor PD-L1-engaging characteristics, with respect to dose vs mAb localization in the tumors seen by PET, of therapeutic PD-L1 antibody Atezolizumab (AtzMab). The preclinical observations disclosed herein will have clinically actionable findings. In patients, similar PD-L1 PET-based imaging measurements could potentially be used to guide therapeutic dose intensification to improve therapeutic outcomes (Yang, et al., 2013; Oude Munnink, et al., 2016). Also, such PD-L1 PET measurements could potentially guide future development of new PD-L1-targeted therapeutic agents by enabling quantification of their potential target engagement at the tumor site.

2.1.2. Innovation in using PD-L1 PET in drug development and evaluation: The presently disclosed innovative PD-L1 peptide-based PET imaging strategies allow for evaluation of target engagement potency of current and future anti-PD-L1 therapeutic agents (i.e., occupancy and residence time) at the tumor, where it is most relevant. Dynamic PD-L1 density/turnover, and the extent of PD-L1-expressing tumor burden that impact serum mAb concentrations, along with completeness of tumor perfusion and resultant intratumoral mAb accumulations, significantly impact therapeutic efficacy. Radiolabeled antibodies have been used previously to define required mAb dosing levels and calculate target surface molecule occupancy (Deng, et al., 2016), but a key limitation of that approach is that PD-L1 occupancy at tumor sites of action can only be projected. The presently disclosed approach will effectively address this problem, quantifying PD-L1 occupancy at the tumor site. In addition to thus accounting for the contribution of key tumor physiological parameters to effective mAb doses and accumulations reached, we anticipate that our novel PET tracer-based measures will improve current understanding of why some patients with PD-L1-positive tumors do not respond to CIT, and may guide dose intensification strategies to reach the desired occupancy levels in the tumors.

2.1.3. Assess Utility of PD-L1-PET in Development & Evaluation of PD-L1-Targeted Therapeutic rugs:

2.1.3.1 Rationale

Therapeutic antibodies targeting PD-L1 and PD-1 have shown exceptional efficacy in a small fraction of patients with PD-L1-positive tumors. At currently-used doses, responder and non-responder populations demonstrate approximately 65% PD-L1 occupancy in PBMCs, but the relationship between PD-L1 occupancy in PBMCs and that in tumors, which is dynamic, is poorly understood (Brahmer, et al., 2012). Also, studies in tumor models found that in some tumors, PD-L1 antibodies are restricted to tumor vasculature (Deng, et al., 2016). Preliminary results with radiolabeled AtzMab recapitulated these findings in NSCLC xenografts (Chatterjee, et al., 2016). Taken together, these findings suggest that improved understanding of PD-L1 occupancy at the tumor and its dependence on dose, and of residence times of anti-PD-L1 antibodies at the tumor, are needed to better-inform PD-L1-directed therapies. Without wishing to be bound to any one particular theory, it is thought that PD-L1 PET will provide a valuable tool to assess such PK measures of anti-PD-L1 antibodies (or peptides and small molecules) with respect to target engagement and residence times. Also, it is thought that PET-informed dosing will lead to immune profile changes within tumors that can be quantified by PD-L1 PET and correlated with therapy-induced changes in tumor PD-L1 expression and immune cell infiltrates.

2.1.3.2 Representative Data: Radiolabeled versions of available anti-PD-L1 antibodies and PD-1 derivatives have been used to detect PD-L1 expression non-invasively (Chatterjee, et al., 2016; Deng, et al., 2016; Hettich, et al., 2016; Josefsson, et al., 2016; Lesniak, et al., 2016; Heskamp, et al., 2015; Maute, et al., 2015). To do so, the therapeutic antibody AtzMab was selected for its human and mouse cross-reactivity and specificity of its PD-L1 detection was demonstrated, by PET, SPECT and optical imaging, in human TNBC and NSCLC xenografts in immunocompromised mice and in the 4T1 syngeneic mammary tumor model (Chatterjee, et al., 2016; Lesniak, et al., 2016) (FIG. 20A, FIG. 20B, FIG. 20C, and FIG. 20D). AtzMab binds both human and mouse PD-L1 with high affinity, with dissociation constants (Kd) of 0.43 nM and 0.13 nM, respectively. (Irving, et al., 2012; Powles, et al., 2014) AtzMab is in clinical evaluation for treatment of advanced or metastatic bladder cancer, (Powles, et al., 2014) melanoma, (Hamid, et al., 2013) NSCLC, (Spigel, et al., 2013) RCC, (Cho, et al., 2013) TNBC and several other cancers.

Accumulation of radiolabeled AtzMab within tumors was found to be PD-L1-specific in both cancer types (NSCLC and TNBC) (Chatterjee, et al., 2016; Lesniak, et al., 2016). [$^{111}$In]AtzMab accumulation within tumors also was found to be not entirely PD-L1 expression-dependent, suggesting that interstitial fluid pressure, tumor convection, and spatial variation in extravasation could be some of the contributing factors, an issue often observed with antibodies (Baxter, et al., 1989). MDAMB231 TNBC xenografts showed higher tissue accumulations (as percentage of injected dose per gram; % ID/g) than subcutaneous and orthotopic H2444 NSCLC tumors, which showed higher PD-L1 expression by both flow cytometry and IHC analyses (Chatterjee, et al., 2016). By exploiting the specificity and flexibility of our novel peptide-based PD-L1 PET tracer, we analyzed the kinetics of AtzMab accumulation within PD-L1-expressing tumors in vivo, by an entirely different approach that accounts for multitude of factors influencing antibody distribution in the tumors and can be applied to a variety of PD-L1 targeted antibodies.

Figure 21:
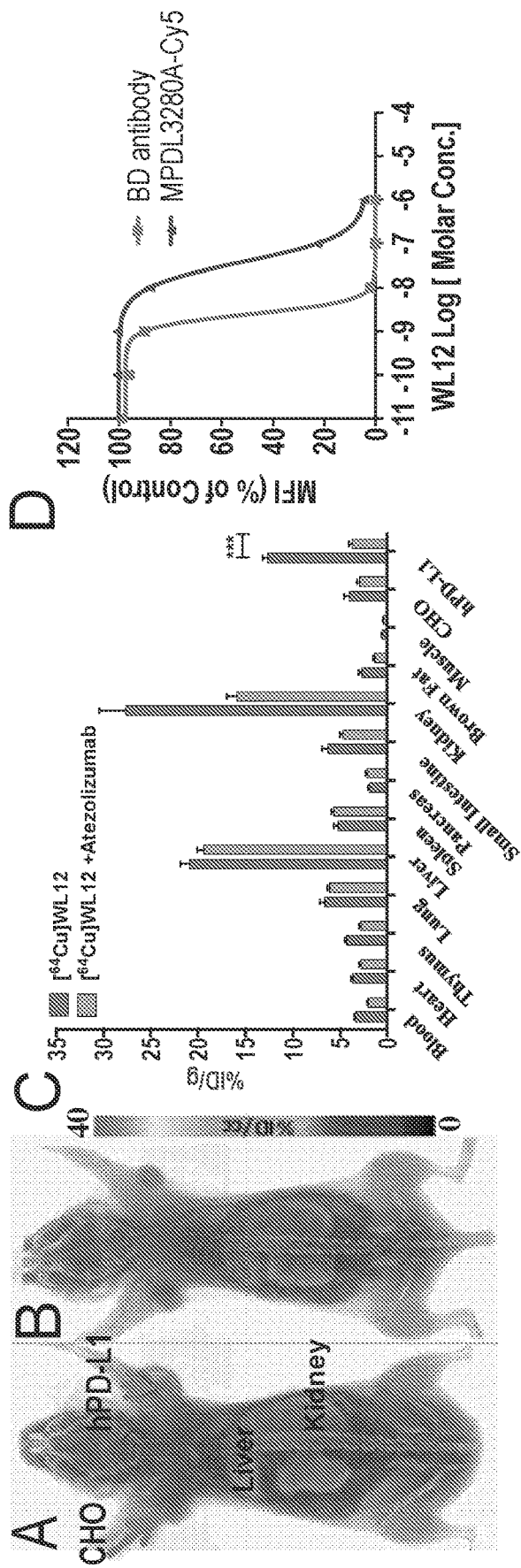

2.1.3.3 PD-L1 therapeutic antibody accumulation in the tumors by PD-L1 PET: While evaluating the specificity of WL12 for PD-L1, it was discovered that WL12 competes with AtzMab to the same binding site on PD-L1. This provides a novel and previously unanticipated means to evaluate AtzMab therapy at tumor sites, where it is needed, using PD-L1-directed PET. Improved understanding of the distribution of PD-L1 antibodies in tumors may impact clinical antibody dosing and therapeutic monitoring. Therefore, the ability of [$^{64}$Cu]WL12-PET to assess AtzMab binding to PD-L1 within tumors was tested. Accumulation of radioactivity in hPD-L1 tumors was reduced by 80% in mice injected with AtzMab (20 mg/kg) as quantified by [$^{64}$Cu]WL12-PET and biodistribution studies (FIG. 21A, FIG. 21B, and FIG. 21C). A reduced, but not significant differences in radioactivity uptakes in other tissues except for kidneys was observed, indicating that [$^{64}$Cu]WL12 binding is specific to human PD-L1 (Lesniak, et al., 2016). By in vitro binding studies we found that unlabeled WL12 concentration-dependently inhibited binding of Cy5-conjugated AtzMab to PD-L1, with $IC_{50}$ of 37.8 nM, confirming that both ligands compete for PD-L1 binding (FIG. 21D), although AtzMab was more potent than WL12 at inhibiting [$^{64}$Cu]WL12 binding and should allow to detect unoccupied PD-L1 levels in the tumor upon AtzMab dosing. Collectively, these results demonstrate that binding sites of WL12 and AtzMab overlap and indicate the potential utility of [$^{64}$Cu]WL12-PET for evaluating AtzMab target engagement and residence time (target engagement potency) in the PD-L1-expressing tumors. The applicability of this approach was extended to cancer cell lines with native increase in PD-L1 expression. In triple breast cancer xenografts, the ability of [$^{64}$Cu]WL12 to detect AtzMab accumulation in high PD-L1 expressing MDAMB231 xenografts was observed (FIG. 22). A significant reduction in PD-L1 PET imaging agent uptake in mice receiving 20 mg/Kg AtzMab dose also was observed.

It is thought that similar application with other PD-L1 targeting therapeutic antibodies such as Avelumab (AvMab). AvMab is a human IgG1 antibody now in multiple phase III clinical trials in several cancers including NSCLC (NCT02395172), advanced RCC and gastric cancer. The crystal structure of PD-L1 complexed with AvMab was analyzed, and it was found that AvMab interacts with some of the same amino acids on PD-L1 (R113, D61, and E58) as does WL12 (Liu, et al., 2016), indicating a potentially advantageous utility of WL12-based tracers for evaluating in vivo target engagement by AvMab and perhaps other PD-L1-directed therapeutic mAbs. These studies will validate the potential of PD-L1-PET to evaluate an ongoing PD-L1 mAb therapy with respect to its target engagement potency.

Example 3

Non-Invasive Quantification of PD-L1 Engagement by Theranostic Antibodies 3.1 Overview. Programmed death ligand-1 (PD-L1) targeted antibody therapeutics are employed in nearly a quarter of clinical trials that involve immune checkpoint inhibitors. Total PD-L1 levels, their occupancy by PD-L1 therapeutics and the relevance of dosing to degree and duration of target engagement within tumors to ensure optimum immune response remain unknown. Occupancy of PD-L1 within tumors could be influenced by dynamic changes in expression of PD-L1, and tumor intrinsic and extrinsic parameters that alter plasma and tumor antibody concentrations. Such key variations, however, are not captured by peripheral pharmacokinetic and pharmacodynamics assessments. To address the gap in dose-medication exposure relationships of PD-L1 therapeutics, a radiolabeled PD-L1 binding peptide that enabled quantification of dynamic changes in PD-L1 expression was investigated. Structural analyses showed an overlap in peptide and therapeutic monoclonal antibody (mAbs) interactions with PD-L1 allowing occupancy of therapeutic mAbs in the tumors to be measured using positron emission tomography (PET). In multiple xenograft models, PET imaging and biodistribution studies showed that variable PD-L1 expression, and its saturation by PD-L1 therapeutic antibodies, can be quantified. Furthermore, PD-L1 occupancy at the tumor by three distinct antibodies was measured and the dose and time effects on PD-L1 occupancy at the tumor were quantified. Peptide-based PD-L1 PET is promising as a tool for optimizing dose and therapeutic regimens, with the goal of reducing immune-related adverse events.

More particularly, the presently disclosed subject matter uses quantitative positron emission tomographic (PET) imaging to address the need to characterize PD-L1 expression levels and PD-L1 mAb target engagement at the tumor, in vivo. It is effective for repeated measures of target expression in tumors (Willman, et al., 2008) and in drug development and evaluation, but is used only rarely for receptor occupancy studies in oncology (Rathkopf, et al., 2013), and has specifically not been realized for pharamacokinetic and pharmacodynamic evaluation of PD-L1 or PD-1 mAbs (Peterson, et al., 2008; Linden, et al., 2006).

A small peptide radiolabeled with $^{64}$Cu, [$^{64}$Cu]WL12, which binds with high affinity and specificity to human PD-L1, and generates high contrast images within 120 min of radiotracer administration was recently developed (Chatterjee, et al., 2017). This example describes [$^{64}$Cu]WL12-PET for PD-L1 detection and quantify dynamic changes in PD-L1 expression in experimental models of lung and breast cancer. The ability of [$^{64}$Cu]WL12 PET to assess PD-L1 engagement by three different FDA-approved mAbs, atezolizumab, avelumab and durvalumab (DurMab) was evaluated. Furthermore, the relevance of PD-L1 mAb dose on the degree and duration of PD-L1 engagement at the tumor was non-invasively assessed.

3.2 Background. Cancer immunotherapy (CIT) produces durable responses to a variety of malignancies. One of the preferred CIT targets is the checkpoint protein programmed death-ligand 1 (PD-L1). PD-L1 is expressed by many tumors as a means of evading tumor-infiltrating cytotoxic T cells (Topalian, et al., 2016), causing immune suppression via binding directly to PD-1 receptor (Okazaki, et al., 2007; Topalian, et al., 2015). Multiple PD-L1 targeted monoclonal antibody therapeutics (mAbs) that inhibit PD-L1:PD-1 interaction are in clinical trials, and nearly 30% of patients receiving these treatments demonstrate durable responses (Topalian, et al., 2015; Lipson, et al., 2015). In spite of the successes, however, there is an incomplete understanding of biological mechanisms that contribute to unusual response patterns, such as delayed or mixed tumor regression, that pose clinical challenges and limit the ability of clinicians to advance checkpoint therapies.

Therapeutic action of anti-PD-L1 mAbs is primarily considered to take place within the tumor microenvironment (Topalian, et al., 2015). Pharmacodynamic (PD) data, however, are limited; they are not reflective of target engagement at the site of action (the tumor), they are reported in only a limited number of trials, and they are obtained using peripheral blood mononuclear cells (PBMCs). For PD-L1 antibody BMS-936559, a uniform target occupancy of 64-70% has been reported for doses ranging from 0.1 mg/kg to 10 mg/kg (Brahmer, et al., 2012). Much remains unknown about the disposition of the PD-L1 mAbs at the most relevant site, namely, the tumor, and the relevance of dosing to degree and duration of target engagement to ensure optimum immune response.

The best-studied predictive biomarker for therapeutic monitoring of PD-L1/PD-1 targeted therapies is PD-L1 immunohistochemistry (IHC) (Gibney, et al., 2016). That method, however, has significant limitations, as it requires biopsy specimens of limited availability, and may not correctly reflect the temporally dynamic immune tumor microenvironment (TME), and the intra- and inter-tumoral heterogeneity of PD-L1 expression (Mansfield, et al., 2016; McLaughlin, et al., 2016). There is an unmet need for non-invasive assessment of PD-L1 expression levels, dynamics, and PD-L1 therapeutic drug disposition in primary and metastatic tumors, and to do so within the standard clinical workflow of imaging.

3.3 Results 3.3.1 Structural analysis and in vitro validation of PD-L 1 interaction with WL12 and PD-L1 mAbs. WL12 is a 14 amino acid peptide that inhibits PD-L1:PD-1 interaction with high affinity (IC50: 20 nM) (Chatterjee, et al., 2017). Earlier molecular modeling analysis suggested an overlap in the interaction surface of PD-L1:WL12 and PD-L1:PD-1 with four amino acids of PD-L1 (Y56, E58, D61 and A113) contributing to significant molecular interactions (Chatterjee, et al., 2017). The buried surface of PD-L1 in complex with the therapeutic antibody atezolizumab (AtzMab) (2,106 Å$^2$) is larger than that of PD-1 (1,970 Å$^2$) (Lee, et al., 2017). Without wishing to be bound to any one particular theory, it was thought that the WL12 interaction surface on PD-L1 also overlaps with that of clinically available therapeutic mAbs because they are similarly designed to inhibit PD-L1:PD-1 interaction. To test that, the predicted binding conformations of WL12 were compared with those of PD-L1 mAbs. The overlap of AA contacts between all of the mAbs, as well as PD-1 and WL12, reveal a common binding domain composed of PD-L1 residues Y56, E58, A113, M115 and Y123. As revealed in the visualization of the PD-L1 molecular surfaces (FIG. 33A, FIG. 34A), the overlapping region (cyan) forms a deep pocket, and acts as an anchor point for all of the points of interaction. In terms of surface area AtzMab (red) interacts with more of the PD-L1 surface with loops from the antibody generating molecular contacts with residues on all sides of the common binding core with overlap with the interaction surfaces from PD-1 (purple), WL12 (green), avelumab (AveMab, orange), and durvalumab (DurMab, blue).

To support the aforementioned structural analysis Cy5-labeled AtzMab, AveMab and DurMab were prepared through conjugation of the antibody to the commercially available Cy5 fluorescent N-hydroxysuccinimide ester, followed by competitive inhibition assays with WL12 in CHO cells constitutively expressing PD-L1 (Cho-hPD-L1) and MDAMB231 breast cancer cells, which naturally express PD-L1 (Chatterjee, et al., 2016). WL12 dose-dependent inhibition of Cy5-PD-L1 mAb binding to PD-L1 was observed, with inhibitory concentrations from 2-5 nM (FIG. 33B). HCC827 and H226 non-small cell lung cancer (NSCLC) cells also were tested. Each of which naturally expresses PD-L1, incubated with fluorescent versions of AtzMab, AveMab and DurMab in the presence of 5 nM WL12. Flow cytometry showed a significant reduction (P<0.001) in bound fluorescence, further demonstrating the capacity of WL12 to disrupt antibody-PD-L1 interactions (FIGS. 34C and 34D). Further confirmation of the specificity of the WL12:PD-L1 interaction was obtained by not observing a change in bound fluorescence when MDX1338, a CXCR4-specific antibody, was used. PD-L1-positive (HCC827, H226, MDAMB231 and hPD-L1) and PD-L1-negative (Sum149 and CHO) cells were incubated with a WL12-analog radiolabeled with $^{64}$Cu ([$^{64}$Cu]WL12). It was previously demonstrated that WL12 analogs bound PD-L1 with high affinity (IC$_{50}$<20 nM) and selectivity in vitro and in vivo in hPD-L1/CHO cells, but have not been validated in human cancer cell lines with variable expression (Chatterjee, et al., 2017). High, expression-dependent uptake of [$^{64}$Cu]WL12 in PD-L1 positive cells were observed compared to PD-L1 negative cells (P<0.0001). Furthermore, significant blockade of [$^{64}$Cu]WL12 uptake in all the PD-L1 positive cells (P<0.0001) was observed when treated with 60 nM mAbs compared to PBS treated controls, as a further check on PD-L1 binding specificity (FIG. 33C). The results indicate that [$^{64}$]WL12 could be used to detect free PD-L1 levels in tumors and monitor PD-L1 engagement by PD-L1 mAbs.

3.3.2 Quantifying Tumor PD-L1 engagement by AtzMab. To evaluate PD-L1 engagement by the therapeutic mAbs at the tumor non-invasively in vivo, NSCLC xenograft models were studied. Those models were selected because nearly 50% of NSCLCs are PD-L1-positive and PD-L1 IHC is used as a predictive biomarker in patients with NSCLC undergoing immune checkpoint therapy (Mansfield, et al., 2016). NOD scid gamma mice bearing H226 and HCC827 cell-derived xenografts that exhibit low and moderate PD-L1 expression, respectively (FIG. 36A), were treated them with a single dose of AtzMab (20 mg/kg for 24 h) administered intravenously. PET images acquired 2 h after [$^{64}$Cu]WL12 injection showed higher accumulation of [$^{64}$Cu]WL12 in HCC827 tumors compared to H226. There is a clear reduction in the accumulation of radioactivity in tumors of AtzMab-treated mice, indicating reduced levels of available PD-L1 sites, compared to treated controls (FIG. 35A and FIG. 35B). The PET imaging results were further confirmed by ex vivo measurements of biodistribution (FIG. 35D and FIG. 35E, FIG. 36B and FIG. 36C), which showed significant reductions in [$^{64}$Cu]WL12 percent of injected dose per gram values (% ID/g) in AtzMab-treated mice compared to saline controls: 34% (P<0.0001) in mice with H226 and 47% (P<0.001) in HCC827 xenografts. PD-L1 expression levels were confirmed by PD-L1 IHC of the xenografts (FIG. 35C and FIG. 35F). The results demonstrate that [$^{64}$Cu]WL12 can be used to quantify in vivo targeting of PD-L1 at the tumor by AtzMab.

To assess the effect of a single dose of AtzMab on targeting different PD-L1 levels in the tumors, PET and biodistribution studies were performed in tumors derived from the CHO-hPDL1 cell line, which has four- to ten-fold higher PD-L1 expression than NSCLC cells (FIG. 36). The CHO-hPDL1/CHO tumor-bearing mice treated with Atz-Mab (20 mg/kg for 24 h) showed significant reduction in [$^{64}$Cu]WL12 uptake in CHO-hPDL1 tumors, compared to controls FIG. 35G). Biodistribution studies showed a 77% reduction in [$^{64}$Cu]WL12 binding in the CHO-hPDL1 tumors compared to AtzMab-treated tumors (FIG. 35H, FIG. 36D) (P<0.0001), demonstrating measurement of tumor PD-L1 targeting by AtzMab. A low level of [$^{64}$]WL12 uptake was observed in PD-L1-negative CHO tumors, which was similar to that of hPD-L1 tumors treated with AtzMab. Those observations were confirmed by strong and week immunoreactivity observed in hPD-L1 and CHO tumors, respectively (FIG. 35I). The results demonstrate that [$^{64}$Cu]WL12-PET can detect graded levels of PD-L1 expression in tumors, and that a single 20 mg/kg AtzMab dose can engage a wide range of PD-L1 levels in the tumors.

3.3.3. Quantifying dynamic changes in PD-L1 expression. PD-L1 is known to be upregulated in response to various cytokines, importantly interferon gamma (IFNγ), which contributes to dynamic and spatiotemporal heterogeneity in PD-L1 expression (Taube, et al., 2015; Taube, et al., 2012). The robustness of [$^{64}$Cu]WL12 to quantify inducible PD-L1 expression within tumors in vivo was evaluated to determine whether the blockade of such upregulated PD-L1 by AtzMab treatment can be monitored by [$^{64}$Cu]WL12 PET (FIG. 37A, FIG. 37B, FIG. 37C, FIG. 37D, FIG. 37E, and FIG. 37F).

To do so, an A549 NSCLC cell line with doxycycline-inducible PD-L1 expression (A549-iPD-L1) was generated. A549 is a Kras G12S lung adenocarcinoma cell line that expresses low PD-L1 at baseline. It has been transduced with PD-L1 in the all-in-one lentivirus pINDUCER20 vector (Meerbrey, et al., 2011), selected with G418, confirmed for PD-L1 induction by flow cytometry (FIG. 37A) and used for in vitro and in vivo studies. Cy5-PD-L1-mAbs binding to doxycycline-treated A549-iPDL1 cells was blocked by WL12 validating the specificity of WL12 (FIG. 37B). Also, incubation of cells with [$^{64}$Cu]WL12 showed a 5.5-fold increase in radioactivity uptake in doxycycline treated vs. untreated and PD-L1-low A549 cells (P<0.0001). [$^{64}$Cu]WL12 binding to doxycycline-treated A549-iPDL1 cells was significantly decreased (65%, P>0.0001) in the presence of 60 nM AtzMab, AveMab and DurMab (FIG. 37C). Those in vitro studies were validated by in vivo studies showing that accumulation of [$^{64}$Cu]WL12 in A549-iPDL1 NSCLC tumors after 72 h of doxycycline treatment was 65% higher than in the A549 control tumors (P>0.0001). That increase in [$^{64}$Cu]WL12 uptake in the tumors was decreased >75% in the 20 mg/kg AtzMab treatment group, compared to control A549 tumors, as quantified by [$^{64}$Cu]WL12-PET and biodistribution studies (FIG. 37D and FIG. 37E). IHC analysis of the tumors demonstrated an intense PD-L1 signal in A549-iPDL1 but not in A549 tumors confirming imaging and biodistribution results (FIG. 37F). Taken together, the results demonstrate the potential of [$^{64}$Cu]WL12 to detect dynamic changes in PD-L1 expression levels, and its blockade by AtzMab. Accordingly, it is expected that PET will play a key role in quantifying dynamic changes in PD-L1 expression within the standard clinical work flow, providing a novel way to inform therapy decisions.

3.3.4. Quantifying tumor PD-L1 engagement by different antibodies. Radiolabeled anti-PD-L1 antibodies have been developed and their potential to assess PD-L1 expression in human tumor xenografts and syngeneic murine tumor models non-invasively has been demonstrated (Chatterjee, et al., 2016; Heskamp, et al., 2015; Maute, et al., 2015; Deng, et al., 2016; Hettich, et al., 2016; Josefsson, et al., 2016). Although such radiolabeled antibody conjugates are now used clinically to detect PD-L1 (NCT02453984) and imaging other tumor-specific proteins (Gebhart, et al., 2016) and to determine antibody kinetics, their routine clinical application is limited. To enhance contrast and lesion detection (Pandit-Taskar, et al., 2015; Oosting, et al., 2016), radiotracers with faster clearance times (hours vs. days) are needed (Wu, 2014). A further limitation is that observations made using radiolabeled antibodies are highly specific to the antibody under investigation and dependent on antibody properties such as valency, shape, size, isoelectric point, and dosage, each of which influences its pharmacokinetics. Such inherent biophysical characteristics of mAbs also influence plasma half-life, tissue exposure, and ultimately efficacy. A new approach is needed that: (i) accounts for target engagement of PD-L1 antibodies, while (ii) takes into account the properties of mAbs, and (iii) is applicable to all antibodies.

The ability of [$^{64}$Cu]WL12-PET to quantify non-invasively PD-L1 engagement at the tumor by each of the three FDA-approved antibodies, AtzMab, AveMab and DurMab was evaluated. MDAMB231 tumor-bearing NSG mice were treated with AtzMab, or AveMab, or DurMab, and 24 h later imaged them with [$^{64}$Cu]WL12-PET (FIG. 39A, FIG. 39B, FIG. 39C, and FIG. 39D). In all treated mice, the signal was low in the tumors compared to saline controls, confirming low levels of free PD-L1 from tumor PD-L1 engagement and radiotracer blockade by the mAbs. Ex vivo quantification of tumors validated those observations and demonstrated approximately 60% less uptake of [$^{64}$Cu]WL12 in the tumors of mAb treated mice (P<0.0001) compared to saline controls (FIG. 39E), at 120 min after injection. IHC analysis of saline controls demonstrated moderate to high PD-L1 intensity in the tumors (FIG. 39F). The results demonstrate that tumor PD-L1 engagement by PD-L1 therapeutic mAbs can be quantified by [$^{64}$Cu]WL12-PET regardless of the distinct biophysical properties, plasma and tissue kinetics of each antibody.

3.3.5. Effect of Dose on PD-L1 occupancy at the tumor. Antibody kinetics at the tumors is governed by both tumor intrinsic and extrinsic parameters (Agoram, 2009). It was recently discovered that factors other than PD-L1 expression itself can reduce accumulation of the PD-L1-targeted therapeutic AtzMab and its mouse chimera (PRO304397) within NSCLC, TNBC and colon tumors (Chatterjee, et al., 2016). Furthermore, at doses less than 1 mg/kg, systemically injected radiolabeled anti-PD-L1 antibody PRO304397 was primarily associated with tumor vasculature, and showed minimal diffusion into tumor parenchyma in PD-L1-expressing syngeneic mouse tumor models (Deng, et al., 2016). Those findings may be attributable to factors such as elevated intratumoral interstitial pressure (Baxter, et al., 1989; Baxter, et al., 1990), which impedes accumulation of mAbs in tumors, contributing to resistance (Goel, et al., 2011). Such effects might also impede the access of large PD-L1-directed agents' to targeted tumor cells and immune infiltrates. Occupancy measurements of PD-L1 and PD-1 therapeutics have not been reported at the tumor and have been constrained to assessments made using PBMCs.

To evaluate the effect of dose on tumor PD-L1 occupancy at the tumor, mice bearing MDAMB231 tumors were injected with escalating doses of AtzMab from 0.009 to 24 mg/kg body weight. Twenty four hours later imaging and biodistribution studies were performed 2 h after the injection of [$^{64}$Cu]WL12. PET images of mice that received 0.06 mg/kg showed no difference in [$^{64}$Cu]WL12 uptake compared to untreated controls, indicating low PD-L1 occupancy by AtzMab at the tumor (FIG. 41A). At the 0.6 and 3.2 mg/kg dose, there was a proportionate decrease in signal intensity in the tumors indicating—for the 3.2 mg/kg dose—a near 100% target engagement at the tumor by the antibody.

The accumulated radioactivity (% ID/g) in the tumors was then used to fit an inhibitory sigmoidal E. model. The % ID/g data appropriately fitted and described the relationship between the dose of the AtzMab used in our experiment and the decrease in free PD-L1 ligands at the tumor (FIG. 41B and FIG. 41C), detected using the peptide radiotracer [$^{64}$Cu]WL12. The dose of the AtzMab responsible for 50% of the maximum PD-L1 engagement in the tumor ($ID_{50}$) or maximum fractional decrease in free PD-L1 ligands from baseline ($I_{max}$) was estimated to be 0.43 mg/kg (Table 2). The $ID_{90}$ and $ID_{96}$, responsible for 90% and 96% of $I_{max}$, corresponded to 0.87 mg/kg and 1.19 mg/kg, respectively. These dose levels are comparable to the dose of 1 mg/kg reported by Deng et al for PRO304397. (Deng, et al., 2016) Assuming similar average $V_{ss}$ of 50 mL/kg for the anti-PD-L1 and the chimeric anti-PD-L1 antibody PRO304397(21), the expected average plasma concentrations resulting from $ID_{50}$, $ID_{90}$ and $ED_{96}$ were tentatively estimated to be 59 nM (8.6 mcg/mL), 120 nM (17.4 mcg/mL) and 164 nM (23.8 mcg/mL), respectively. These results indicate the potential of using measurements made at the tumor for dose selection and optimization.

The interaction of antibodies with their target is different from that of small molecules, in that antibody binding can influence the natural kinetics of PD-L1 such as stabilization or internalization of the PD-L1 and development of antitherapeutic antibodies, which could have a significant impact on antibody tumor and serum kinetics (Tabrizi, et al., 2006). Earlier pharmacokinetic studies for AtzMab reported a non-linear PK below 0.6-1 mg/kg and linear PK above 1 mg/kg dose and a tendency towards reduced serum antibody concentrations were noted in patients that developed ATAs (Stroh, et al., 2017). The effect of such tumor-intrinsic and extrinsic parameters on PD-L1 antibody PK and occupancy at the tumor, however, is not known.

TABLE 2

Effect of Dose on PD-L1 occupancy at the tumor

| Pharmacodynamic model parameters, units | Mean parameter value (% relative standard error) |
|---|---|
| Baseline$_{free\ PD-L1\ ligands}$, % ID/g | 5.91 (1%) |
| $I_{max}$ | 0.57 (3%) |
| $ID_{50}$, mg/kg | 0.43 (10%) |
| Hill coefficient | 3.12 (19%) |
| Residual error, % ID/g | 0.44 (14%) |

To investigate the ability of [$^{64}$Cu]WL12-PET to detect temporal changes in antibody kinetics at the tumor, MDAMB231 tumor-bearing NSG mice were injected with a 0.6 and 10 or 20 mg/kg dosing of AtzMab that produce non-linear and linear kinetics, respectively, and PET imaging and biodistribution studies were performed at 24 and 120 h. At 24 h, there was a significant reduction in [$^{64}$Cu]WL12 uptake also reflected in tumor uptake values in all three dose groups, compared to untreated controls (FIG. 41D and FIG. 41E). At 120 h, there was a significant increase in [$^{64}$Cu] WL12 uptake in the 0.6 mg/kg dose group compared to 24 h. By contrast, there were no significant temporal difference in [$^{64}$Cu]WL12 uptake in the 10 or 20 mg/kg treatment groups. At 120 h, [$^{64}$Cu]WL12 uptake in the tumor was similar in 0.06 mg/kg treated and saline control groups, suggesting elimination of drug from the tumor, and reflecting the non-linear PK of AtzMab at lower doses. The results show that in a mouse model both dose- and time-dependent changes in PD-L1 engagement can be evaluated by [$^{64}$Cu] WL12-PET.

3.3.6. Discussion

Immune checkpoint therapeutics are being investigated in hundreds of clinical trials, approximately 25% of which target PD-L1. Since only 30% of patients receiving PD-L1 therapeutics respond to treatment, the molecular and cellular basis of response and resistance to these therapies are being investigated using transcriptional, genetic, and epigenetic studies. The relevance of dose to drug accumulation and target saturation, which is relevant to efficacy, at the tumor is unknown. Additionally, the large size of antibody therapeutics limits tumor penetration and poses unique challenges for pharmacodynamic assessments at the site of action. An effective method that accounts for both tumor intrinsic and tumor extrinsic parameters, provides PD-L1 saturation/occupancy data in real-time at the tumor, and that can be widely applied has been lacking. This lack of knowledge impedes dose selection, dose optimization, therapeutic development, and therapy optimization to reduce toxicities. In our present study, it is shown that a radiolabeled PD-L1 binding peptide can non-invasively detect variable and dynamic PD-L1 expression levels and can be used to measure occupancy at the tumor while accounting for tumor intrinsic (PD-L1 expression, recycling, interstitial pressure) and extrinsic parameters (antibody isotype, kinetics, ATAs, catabolism) thus providing an universal means to monitor the therapeutic activity of PD-L1:PD-1 interaction inhibiting PD-L1 antibodies at the tumor.

Although IHC-based clinical tests have previously been developed to assess PD-L1 expression in the tumors (Herbst, et al., 2014; Roach, et al., 2016; Meng, et al., 2015), PD-L1 IHC takes into account only a small fraction (0.1%) of a single lesion. Such an approach has significant limitations, because PD-L1 expression in the tumor microenvironment is spatially and temporally heterogeneous, and immune therapy responses are delayed, complex and abscopal in nature. Also, the tissue samples acquired by biopsy for testing are typically very limited, and may be needed for molecular profiling to identify targetable oncogenic mutations in other pathways (e.g. BRCA1, BRCA2, PARP) that confer sensitivity or resistance to existing therapies (Nolan, et al., 2017). Such precious samples often make it impractical to perform multiple PD-L1 assessments for reliable representation of PD-L1 expression (Gibney, et al., 2016). These issues are compounded in patients with metastatic disease, a population in which immune checkpoint therapeutics are extensively investigated. Such factors contribute to our limited success in advancing immunotherapies. The dynamic nature of both PD-L1 expression and of the broader tumor-immune microenvironment, necessitates development of PET radiotracers that permit rapid evaluation of the TME. The presently disclosed studies with [$^{64}$Cu]WL12 demonstrate that variable and dynamic changes in PD-L1 expression could be quantified within the standard clinical work flow, yielding important clinical implications for patient selection and monitoring therapy.

PD-L1 therapeutic antibodies have become important agents in cancer immunotherapy. For small molecules, in vitro binding affinity measurements and occupancy studies are routinely used for dose selection in CNS diseases and predictive of pharmacological response (Lee, et al., 2006). Large molecules, however, such as antibodies pose unique challenges in predicting in vivo receptor occupancy based on in vitro binding affinity (Agoram, 2009). Concentrations of antibodies in the tumors are influenced by several tumor intrinsic parameters, such as antigen density and turnover, tumor burden, and tumor perfusion that limit intratumoral penetration of mAbs. Tumor and plasma concentrations of mAbs are further influenced by tumor extrinsic factors such as affinity, dose, patient variability, cachexia, and development of anti-therapeutic antibodies (Sheng, et al., 2017). Existing PK/PD prediction models rely on in vitro and PBMC-based measurements to predict the optimal dose (Deng, et al., 2016). The presently disclosed subject matter, however, now demonstrates that PET can be used to measure PD-L1 occupancy by therapeutic antibodies in real-time at the tumor and non-invasively.

Radiolabeled antibodies, such as atezolizumab, supported by peripheral pharmacodynamics assessments and PK/PD modeling, are routinely used to predict the mAb dosing levels required to achieve the desired PD-L1 occupancy at the tumor (Deng, et al., 2016). Those measurements and mathematical modeling derived occupancy predictions are often specific for a given antibody, as plasma and tumor concentrations of antibodies are influenced by antibody isotype and biophysical properties, such as charge and valency, thus limiting generalization of such observations to other PD-L1 mAbs (Kamath, 2016). A tool is needed that can be used to assess antibody kinetics and target engagement potential at the tumor for an ever expanding array of PD-L1 therapeutic mAbs. The presently disclosed subject matter addresses this need. The in silico modeling studies, combined with in vitro and in vivo data using WL12-PET, demonstrate that PD-L1 saturation/occupancy at the tumor can be quantified, a concept that can be applied to all the PD-L1 therapeutic mAbs in clinical trials.

Collectively, the presently disclosed data demonstrate that dynamic changes in PD-L1 expression in the tumors, and PD-L1 saturation/occupancy by therapeutic antibodies, can be non-invasively quantified, with two features, namely being independent of antibody characteristics, and accounting for tumor intrinsic and extrinsic parameters. The presently disclosed results linking the dose to PD-L1 occupancy at the tumor, for three distinct therapeutic antibodies, Atz-Mab, AveMab, DurMab, are expected to have relevance for therapeutic response and dosing efficacy.

3.3.7. Summary

The presently disclosed subject matter demonstrates that a radiolabeled PD-L1 binding peptide can non-invasively detect variable and dynamic PD-L1 expression levels and can be used to measure occupancy at the tumor while accounting for tumor intrinsic (PD-L1 expression, recycling, interstitial pressure) and extrinsic parameters (antibody isotype, kinetics, ATAs, catabolism) thus providing an universal means to monitor the therapeutic activity of PD-L1:PD-1 interaction inhibiting PD-L1 antibodies at the tumor.

The studies with [$^{64}$Cu]WL12 demonstrate that variable and dynamic changes in PD-L1 expression could be quantified within the standard clinical work flow, yielding important clinical implications for patient selection and monitoring therapy.

Existing PK/PD prediction models for antibodies rely on in vitro and PBMC-based measurements to predict the optimal dose (Deng, et al., 2016). The presently disclosed subject matter, however, demonstrates that PET can be used to measure PD-L1 occupancy by therapeutic antibodies in real-time at the tumor and non-invasively.

A tool is needed that can be used to assess antibody kinetics and target engagement potential at the tumor for an ever expanding array of PD-L1 therapeutic mAbs. The presently disclosed subject matter now addressed this need. The in silico modeling studies, combined with in vitro and in vivo data using WL12-PET, demonstrate that PD-L1 saturation/occupancy at the tumor can be quantified, a concept that can be applied to all the PD-L1 therapeutic mAbs in clinical trials.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Agoram, B. M. (2009) Use of pharmacokinetic/pharmacodynamic modelling for starting dose selection in first-in-human trials of high-risk biologics. *Br J Clin Pharmacol* 67, 153-160.

Anderson, C. J., and Ferdani, R. (2009) Copper-64 radiopharmaceuticals for PET imaging of cancer: advances in preclinical and clinical research. *Cancer Biother Radiopharm* 24, 379-93.

Baxter, L. T., and Jain, R. K. (1989) Transport of fluid and macromolecules in tumors. I. Role of interstitial pressure and convection. *Microvasc Res* 37, 77-104.

Baxter, L. T., and Jain, R. K. (1990) Transport of fluid and macromolecules in tumors. II. Role of heterogeneous perfusion and lymphatics. *Microvasc Res* 40, 246-263.

Boswell, C. A., Sun, X., Niu, W., Weisman, G. R., Wong, E. H., Rheingold, A. L., and Anderson, C. J. (2004) Comparative in vivo stability of copper-64-labeled cross-bridged and conventional tetraazamacrocyclic complexes. *J Med Chem* 47, 1465-74.

Brahmer, J. R., Tykodi, S. S., Chow, L. Q., Hwu, W. J., Topalian, S. L., Hwu, P., Drake, C. G., Camacho, L. H., Kauh, J., Odunsi, K., Pitot, H. C., Hamid, O., Bhatia, S., Martins, R., Eaton, K., Chen, S., Salay, T. M., Alaparthy, S., Grosso, J. F., Korman, A. J., Parker, S. M., Agrawal, S., Goldberg, S. M., Pardoll, D. M., Gupta, A., and Wigginton, J. M. (2012) Safety and activity of anti-PD-L1 antibody in patients with advanced cancer. *N Engl J Med* 366, 2455-2465.

Chatterjee, S., Lesniak, W. G., Gabrielson, M., Lisok, A., Wharram, B., Sysa-Shah, P., Azad, B. B., Pomper, M. G., and Nimmagadda, S. (2016) A humanized antibody for imaging immune checkpoint ligand PD-L1 expression in tumors. *Oncotarget* 7, 10215-27.

Chatterjee, S., Lesniak, W. G., Miller, M. S., Lisok, A., Sikorska, E., Wharram, B., Kumar, D., Gabrielson, M., Pomper, M. G., Gabelli, S. B., and Nimmagadda, S. (2017) Rapid PD-L1 detection in tumors with PET using a highly specific peptide. *Biochem Biophys Res Commun* 483, 258-263.

Cho, D. C., Sosman, J. A., Sznol, M., Gordon, M. S., Hollebecque, A., Hamid, O., McDermott, D. F., Delord, J. P., Rhee, I. P., Mokatrin, A., Kowanetz, M., Funke, R. P., Fine, G. D., and Powles, T. (2013) Clinical activity, safety, and biomarkers of MPDL3280A, an engineered PD-L1 antibody in patients with metastatic renal cell carcinoma (mRCC). *J Clin Oncol* 31, 15_suppl, 4505-4505.

Deng, R., Bumbaca, D., Pastuskovas, C. V., Boswell, C. A., West, D., Cowan, K. J., Chiu, H., McBride, J., Johnson, C., Xin, Y., Koeppen, H., Leabman, M., and Iyer, S. (2016) Preclinical pharmacokinetics, pharmacodynamics, tissue distribution, and tumor penetration of anti-PD-L1 monoclonal antibody, an immune checkpoint inhibitor. *MAbs* 8, 593-603.

Eisenwiener, K. P., Powell, P., and Macke, H. R. (2000) A convenient synthesis of novel bifunctional prochelators for coupling to bioactive peptides for radiometal labelling. *Bioorg Med Chem Lett* 10, 2133-5.

Friesner, R. A., Banks, J. L., Murphy, R. B., Halgren, T. A., Klicic, J. J., Mainz, D. T., Repasky, M. P., Knoll, E. H., Shelley, M., Perry, J. K., Shaw, D. E., Francis, P., and Shenkin, P. S. (2004) Glide: a new approach for rapid, accurate docking and scoring. 1. Method and assessment of docking accuracy. *J Med Chem* 47, 1739-49.

Gebhart, G., Lamberts, L. E., Wimana, Z., Garcia, C., Emonts, P., Ameye, L., Stroobants, S., Huizing, M., Aftimos, P., Tol, J., Oyen, W. J., Vugts, D. J., Hoekstra, O. S., Schroder, C. P., Menke-van der Houven van Oordt, C. W., Guiot, T., Brouwers, A. H., Awada, A., de Vries, E. G., and Flamen, P. (2016) Molecular imaging as a tool to investigate heterogeneity of advanced HER2-positive breast cancer and to predict patient outcome under trastuzumab emtansine (T-DM1): the ZEPHIR trial. *Ann Oncol* 27, 619-624.

Gibney, G. T., Weiner, L. M., and Atkins, M. B. (2016) Predictive biomarkers for checkpoint inhibitor-based immunotherapy. *Lancet Oncol* 17, e542-e551.

Goel, S., Duda, D. G., Xu, L., Munn, L. L., Boucher, Y., Fukumura, D., and Jain, R. K. (2011) Normalization of the vasculature for treatment of cancer and other diseases. *Physiol Rev* 91, 1071-1121.

Gourni, E., Demmer, O., Schottelius, M., D'Alessandria, C., Schulz, S., Dijkgraaf, I., Schumacher, U., Schwaiger, M., Kessler, H., and Wester, H. J. (2011) PET of CXCR4 expression by a (68)Ga-labeled highly specific targeted contrast agent. *J Nucl Med* 52, 1803-10.

Grishina, I. B., and Woody, R. W. (1994) Contributions of tryptophan side chains to the circular dichroism of globular proteins: exciton couplets and coupled oscillators. *Faraday discussions* 99, 245-262.

Halgren, T. A., Murphy, R. B., Friesner, R. A., Beard, H. S., Frye, L. L., Pollard, W. T., and Banks, J. L. (2004) Glide: a new approach for rapid, accurate docking and scoring. 2. Enrichment factors in database screening. *J Med Chem* 47, 1750-9.

Hamid, O., Sosman, J. A., Lawrence, D. P., Sullivan, R. J., Ibrahim, N., Kluger, H. M., Boasberg, P. D., Flaherty, K., Hwu, P., Ballinger, M., Mokatrin, A., Kowanetz, M., Chen, D. S., and Hodi, F. S. (2013) Clinical activity, safety, and biomarkers of MPDL3280A, an engineered PD-L1 antibody in patients with locally advanced or metastatic melanoma (mM). *J Clin Oncol* 31, 15_suppl, 9010-9010.

Herbst, R. S., Soria, J. C., Kowanetz, M., Fine, G. D., Hamid, O., Gordon, M. S., Sosman, J. A., McDermott, D. F., Powderly, J. D., Gettinger, S. N., Kohrt, H. E., Horn, L., Lawrence, D. P., Rost, S., Leabman, M., Xiao, Y., Mokatrin, A., Koeppen, H., Hegde, P. S., Mellman, I., Chen, D. S., and Hodi, F. S. (2014) Predictive correlates of response to the anti-PD-L1 antibody MPDL3280A in cancer patients. *Nature* 515, 563-7.

Herrmann, K., Schottelius, M., Lapa, C., Osl, T., Poschenrieder, A., Hanscheid, H., Luckerath, K., Schreder, M., Bluemel, C., Knott, M., Keller, U., Schirbel, A., Samnick, S., Lassmann, M., Kropf, S., Buck, A. K., Einsele, H., Wester, H. J., and Knop, S. (2016) First-in-Human Experience of CXCR4-Directed Endoradiotherapy with 177Lu- and 90Y-Labeled Pentixather in Advanced-Stage Multiple Myeloma with Extensive Intra- and Extramedullary Disease. *J Nucl Med* 57, 248-51.

Heskamp, S., Hobo, W., Molkenboer-Kuenen, J. D., Olive, D., Oyen, W. J., Dolstra, H., and Boerman, O. C. (2015) Noninvasive Imaging of Tumor PD-L1 Expression Using Radiolabeled Anti-PD-L1 Antibodies. *Cancer Res* 75, 2928-36.

Hettich, M., Braun, F., Bartholoma, M. D., Schirmbeck, R., and Niedermann, G. (2016) High-Resolution PET Imaging with Therapeutic Antibody-based PD-1/PD-L1 Checkpoint Tracers *Theranostics* 6, 1629-1640.

International PCT patent application publication no. WO2016039749 to Miller, et al., for Macrocyclic Inhibitors of the PD-1/PD-L1 and CD80 (B7-1)/PD-L1 Protein/Protein Interactions, published Mar. 17, 2016.

International PCT patent application publication no. WO 2016/100285 to Mapelli, et al., for Immunomodulators, published Jun. 23, 2016.

International PCT patent application publication no. WO 2016/100608 to Sun, et al. for Immunomodulators, published Jun. 23, 2016.

International PCT patent application publication no. WO 2016/126646 to Miller et al., for Immunomodulators, published Aug. 11, 2016.

Irving, B., Chiu, H., Maecker, H., Mariathasan, S., Lehar, S. M., Wu, Y., and Cheung, J. (2012) (Office, U. S. P., Ed.), Genentech, Inc., USA.

Irving, B., Chiu, H., Maecker, H., Mariathasan, S., Lehar, S. M., Wu, Y., and Cheung, J. (2012) Anti-PD-L1 Antibodies, compositions and articles of manufacture. (Office, U. S. P., ed), Genentech, Inc., USA.

Josefsson, A., Nedrow, J. R., Park, S., Banerjee, S. R., Rittenbach, A., Jammes, F., Tsui, B., and Sgouros, G. (2016) Imaging, Biodistribution, and Dosimetry of Radionuclide-Labeled PD-L1 Antibody in an Immunocompetent Mouse Model of Breast Cancer. *Cancer Res* 76, 472-9.

Kamath, A. V. (2016) Translational pharmacokinetics and pharmacodynamics of monoclonal antibodies. *Drug Discov Today Technol* 21-22, 75-83.

Kelly, S. M., and Price, N. C. (2000) The use of circular dichroism in the investigation of protein structure and function. *Current protein and peptide science* 1, 349-384.

Lee, C. M., and Farde, L. (2006) Using positron emission tomography to facilitate CNS drug development. *Trends Pharmacol Sci* 27, 310-316.

Lee, H. T., Lee, J. Y., Lim, H., Lee, S. H., Moon, Y. J., Pyo, H. J., Ryu, S. E., Shin, W., and Heo, Y. S. (2017) Molecular mechanism of PD-1/PD-L1 blockade via anti-PD-L1 antibodies atezolizumab and durvalumab. *Sci Rep* 7, 5532.

Lesniak, W. G., Chatterjee, S., Gabrielson, M., Lisok, A., Wharram, B., Pomper, M. G., and Nimmagadda, S. (2016) PD-L1 Detection in Tumors Using [(64)Cu]Atezolizumab with PET. *Bioconjug Chem* 27, 2103-2110.

Linden, H. M., Stekhova, S. A., Link, J. M., Gralow, J. R., Livingston, R. B., Ellis, G. K., Petra, P. H., Peterson, L. M., Schubert, E. K., Dunnwald, L. K., Krohn, K. A., and Mankoff, D. A. (2006) Quantitative fluoroestradiol positron emission tomography imaging predicts response to endocrine treatment in breast cancer. *Journal of clinical oncology: official journal of the American Society of Clinical Oncology* 24, 2793-9.

Lipson, E. J., Forde, P. M., Hammers, H. J., Emens, L. A., Taube, J. M., and Topalian, S. L. (2015) Antagonists of PD-1 and PD-L1 in Cancer Treatment. *Semin Oncol* 42, 587-600.

Liu, K., Tan, S., Chai, Y., Chen, D., Song, H., Zhang, C. W., Shi, Y., Liu, J., Tan, W., Lyu, J., Gao, S., Yan, J., Qi, J., and Gao, G. F. (2016) Structural basis of anti-PD-L1 monoclonal antibody avelumab for tumor therapy. *Cell Res* 10.1038/cr.2016.102.

Mansfield, A. S., and Dong, H. (2016) Implications of Programmed Cell Death 1 Ligand 1 Heterogeneity in the Selection of Patients With Non-Small Cell Lung Cancer to Receive Immunotherapy. *Clin Pharmacol Ther* 100, 220-2.

Marrone, K. A., Ying, W., and Naidoo, J. (2016) Immune-Related Adverse Events From Immune Checkpoint Inhibitors. *Clin Pharmacol Ther* 100, 242-251.

Maute, R. L., Gordon, S. R., Mayer, A. T., McCracken, M. N., Natarajan, A., Ring, N. G., Kimura, R., Tsai, J. M., Manglik, A., Kruse, A. C., Gambhir, S. S., Weissman, I. L., and Ring, A. M. (2015) Engineering high-affinity PD-1 variants for optimized immunotherapy and immuno-PET imaging. *Proc Natl Acad Sci USA* 112, E6506-14.

McLaughlin, J., Han, G., Schalper, K. A., Carvajal-Hausdorf, D., Pelekanou, V., Rehman, J., Velcheti, V., Herbst, R., LoRusso, P., and Rimm, D. L. (2016) Quantitative Assessment of the Heterogeneity of PD-L1 Expression in Non-Small-Cell Lung Cancer. *JAMA Oncol* 2, 46-54.

Meerbrey, K. L., Hu, G., Kessler, J. D., Roarty, K., Li, M. Z., Fang, J. E., Herschkowitz, J. I., Burrows, A. E., Ciccia, A., Sun, T., Schmitt, E. M., Bernardi, R. J., Fu, X., Bland, C. S., Cooper, T. A., Schiff, R., Rosen, J. M., Westbrook, T. F., and Elledge, S. J. (2011) The pINDUCER lentiviral toolkit for inducible RNA interference in vitro and in vivo. *Proc Natl Acad Sci USA* 108, 3665-3670.

Meng, X., Huang, Z., Teng, F., Xing, L., and Yu, J. (2015) Predictive biomarkers in PD-1/PD-L1 checkpoint blockade immunotherapy. *Cancer Treat Rev* 41, 868-876.

Morin, A., Eisenbraun, B., Key, J., Sanschagrin, P. C., Timony, M. A., Ottaviano, M., and Sliz, P. (2013) Collaboration gets the most out of software. *Elife* 2, e01456.

Nolan, E., Savas, P., Policheni, A. N., Darcy, P. K., Vaillant, F., Mintoff, C. P., Dushyanthen, S., Mansour, M., Pang, J. B., Fox, S. B., Kathleen Cuningham Foundation Consortium for Research into Familial Breast, C., Perou, C. M., Visvader, J. E., Gray, D. H. D., Loi, S., and Lindeman, G. J. (2017) Combined immune checkpoint blockade as a therapeutic strategy for BRCA1-mutated breast cancer. *Sci Transl Med* 9, 393, eaal4922.

Okazaki, T., and Honjo, T. (2007) PD-1 and PD-1 ligands: from discovery to clinical application. *Int Immunol* 19, 813-24.

Oosting, S. F., van Asselt, S. J., Brouwers, A. H., Bongaerts, A. H., Steinberg, J. D., de Jong, J. R., Lub-de Hooge, M. N., van der Horst-Schrivers, A. N., Walenkamp, A. M., Hoving, E. W., Sluiter, W. J., Zonnenberg, B. A., de Vries, E. G., and Links, T. P. (2016) 89Zr-Bevacizumab PET Visualizes Disease Manifestations in Patients with von Hippel-Lindau Disease. *J Nucl Med* 57, 1244-50.

Oude Munnink, T. H., Henstra, M. J., Segerink, L. I., Movig, K. L., and Brummelhuis-Visser, P. (2016) Therapeutic drug monitoring of monoclonal antibodies in inflammatory and malignant disease: Translating TNF-alpha experience to oncology. *Clin Pharmacol Ther* 99, 419-431.

Oosting, S. F., van Asselt, S. J., Brouwers, A. H., Bongaerts, A. H., Steinberg, J. D., de Jong, J. R., Lub-de Hooge, M. N., van der Horst-Schrivers, A. N., Walenkamp, A. M., Hoving, E. W., Sluiter, W. J., Zonnenberg, B. A., de Vries, E. G., and Links, T. P. (2016) 89Zr-Bevacizumab PET Visualizes Disease Manifestations in Patients with von Hippel-Lindau Disease. *J Nucl Med* 57, 1244-1250.

Pandit-Taskar, N., O'Donoghue, J. A., Durack, J. C., Lyashchenko, S. K., Cheal, S. M., Beylergil, V., Lefkowitz, R. A., Carrasquillo, J. A., Martinez, D. F., Fung, A. M., Solomon, S. B., Gonen, M., Heller, G., Loda, M., Nanus, D. M., Tagawa, S. T., Feldman, J. L., Osborne, J. R., Lewis, J. S., Reuter, V. E., Weber, W. A., Bander, N. H., Scher, H. I., Larson, S. M., and Morris, M. J. (2015) A Phase I/II Study for Analytic Validation of 89Zr-J591 ImmunoPET as a Molecular Imaging Agent for Metastatic Prostate Cancer. *Clin Cancer Res* 21, 5277-85.

Peterson, L. M., Mankoff, D. A., Lawton, T., Yagle, K., Schubert, E. K., Stekhova, S., Gown, A., Link, J. M., Tewson, T., and Krohn, K. A. (2008) Quantitative imaging of estrogen receptor expression in breast cancer with PET and 18F-fluoroestradiol. *Journal of nuclear medicine: official publication, Society of Nuclear Medicine* 49, 367-74.

Phillips T., Simmons P., Inzunza H. D., Cogswell J., Novotny J. Jr, Taylor C., and Zhang X. (2015) Development of an automated PD-L1 immunohistochemistry (IHC) assay for non-small cell lung cancer, *Appl Immunohistochem Mol Morphol.* 23(8):541-9.

Powles, T., Eder, J. P., Fine, G. D., Braiteh, F. S., Loriot, Y., Cruz, C., Bellmunt, J., Burris, H. A., Petrylak, D. P., Teng, S. L., Shen, X. D., Boyd, Z., Hegde, P. S., Chen, D. S., and Vogelzang, N. J. (2014) MPDL3280A (anti-PD-L1) treatment leads to clinical activity in metastatic bladder cancer. *Nature* 515, 558-562.

Rathkopf, D. E., Morris, M. J., Fox, J. J., Danila, D. C., Slovin, S. F., Hager, J. H., Rix, P. J., Chow Maneval, E., Chen, I., Gonen, M., Fleisher, M., Larson, S. M., Sawyers, C. L., and Scher, H. I. (2013) Phase I study of ARN-509, a novel antiandrogen, in the treatment of castration-resistant prostate cancer. *J Clin Oncol* 31, 3525-3530.

Reubi, J. C., and Maecke, H. R. (2008) Peptide-based probes for cancer imaging. *J Nucl Med* 49, 1735-8.

Roach, C., Zhang, N., Corigliano, E., Jansson, M., Toland, G., Ponto, G., Dolled-Filhart, M., Emancipator, K., Stanforth, D., and Kulangara, K. (2016) Development of a Companion Diagnostic PD-L1 Immunohistochemistry Assay for Pembrolizumab Therapy in Non-Small-cell Lung Cancer. *Appl Immunohistochem Mol Morphol* 24, 392-7.

Sastry, G. M., Adzhigirey, M., Day, T., Annabhimoju, R., and Sherman, W. (2013) Protein and ligand preparation: parameters, protocols, and influence on virtual screening enrichments. *J Comput Aided Mol Des* 27, 221-34.

Sheng, J., Srivastava, S., Sanghavi, K., Lu, Z., Schmidt, B. J., Bello, A., and Gupta, M. (2017) Clinical Pharmacology Considerations for the Development of Immune Checkpoint Inhibitors. *J Clin Pharmacol* 57 Suppl 10, S26-S42.

Smith-Jones, P. M., Fridrich, R., Kaden, T. A., Novak-Hofer, I., Siebold, K., Tschudin, D., and Maecke, H. R. (1991) Antibody labeling with copper-67 using the bifunctional macrocycle 4-[(1,4,8,11-tetraazacyclotetradec-1-yl) methyl]benzoic acid. *Bioconjug Chem* 2, 415-21.

Spigel, D. R., Gettinger, S. N., Horn, L., Herbst, R. S., Gandhi, L., Gordon, M. S., Cruz, C., Conkling, P., Cassier, P. A., Antonia, S. J., Burris, H. A., Fine, G. D., Mokatrin, A., Kowanetz, M., Shen, X. D., Chen, D. S., and Soria, J. C. (2013) Clinical activity, safety, and biomarkers of MPDL3280A, an engineered PD-L1 antibody in patients with locally advanced or metastatic non-small cell lung cancer (NSCLC). *J Clin Oncol* 31, 15_suppl, 8008-8008.

Sreerama, N., and Woody, R. W. (2000) Estimation of protein secondary structure from circular dichroism spectra: comparison of CONTIN, SELCON, and CDSSTR methods with an expanded reference set. *Anal Biochem* 287, 252-60.

Stroh, M., Winter, H., Marchand, M., Claret, L., Eppler, S., Ruppel, J., Abidoye, O., Teng, S. L., Lin, W. T., Dayog, S., Bruno, R., Jin, J., and Girish, S. (2017) Clinical Pharmacokinetics and Pharmacodynamics of Atezolizumab in Metastatic Urothelial Carcinoma. *Clin Pharmacol Ther* 102, 305-312.

Sun, X., Li, Y., Liu, T., Li, Z., Zhang, X., and Chen, X. (2016) Peptide-based imaging agents for cancer detection. *Adv Drug Deliv Rev.*

Sunshine, J., and Taube, J. M. (2015) PD-1/PD-L1 inhibitors. *Curr Opin Pharmacol* 23, 32-8.

Tabrizi, M. A., Tseng, C. M., and Roskos, L. K. (2006) Elimination mechanisms of therapeutic monoclonal antibodies. *Drug Discov Today* 11, 81-88.

Taube, J. M., Anders, R. A., Young, G. D., Xu, H., Sharma, R., McMiller, T. L., Chen, S., Klein, A. P., Pardoll, D. M., Topalian, S. L., and Chen, L. (2012) Colocalization of inflammatory response with B7-h1 expression in human melanocytic lesions supports an adaptive resistance mechanism of immune escape. *Sci Transl Med* 4, 127ra137.

Taube, J. M., Young, G. D., McMiller, T. L., Chen, S., Salas, J. T., Pritchard, T. S., Xu, H., Meeker, A. K., Fan, J., Cheadle, C., Berger, A. E., Pardoll, D. M., and Topalian, S. L. (2015) Differential Expression of Immune-Regulatory Genes Associated with PD-L1 Display in Melanoma: Implications for PD-1 Pathway Blockade. *Clin Cancer Res* 21, 3969-3976.

Topalian, S. L., Drake, C. G., and Pardoll, D. M. (2015) Immune checkpoint blockade: a common denominator approach to cancer therapy. *Cancer Cell* 27, 450-61.

Topalian, S. L., Taube, J. M., Anders, R. A., and Pardoll, D. M. (2016) Mechanism-driven biomarkers to guide immune checkpoint blockade in cancer therapy. *Nat Rev Cancer* 16, 275-87.

Wadas, T. J., Wong, E. H., Weisman, G. R., and Anderson, C. J. (2007) Copper chelation chemistry and its role in copper radiopharmaceuticals. *Curr Pharm Des* 13, 3-16.

Willmann, J. K., van Bruggen, N., Dinkelborg, L. M., and Gambhir, S. S. (2008) Molecular imaging in drug development. *Nat Rev Drug Discov* 7, 591-607.

Woodard, L. E., De Silva, R. A., Behnam Azad, B., Lisok, A., Pullambhatla, M., W, G. L., Mease, R. C., Pomper, M. G., and Nimmagadda, S. (2014) Bridged cyclams as imaging agents for chemokine receptor 4 (CXCR4). *Nucl Med Biol* 41, 552-61.

Wu, D., Huang, L., Jiang, M. S., and Jiang, H. (2014) Contrast agents for photoacoustic and thermoacoustic imaging: A review. *Int. J. Mol. Sci.* 15, 23616-23639.

Wu, A. M. (2014) Engineered antibodies for molecular imaging of cancer. *Methods* 65, 139-147.

Yang, J., Zhao, H., Garnett, C., Rahman, A., Gobburu, J. V., Pierce, W., Schechter, G., Summers, J., Keegan, P., Booth, B., and Wang, Y. (2013) The combination of exposure-response and case-control analyses in regulatory decision making. *J Clin Pharmacol* 53, 160-166, Zak, K. M., Kitel, R., Przetocka, S., Golik, P., Guzik, K., Musielak, B., Domling, A., Dubin, G., and Holak, T. A. (2015) Structure of the Complex of Human Programmed Death 1, PD-1, and Its Ligand PD-L1. *Structure* 23, 2341-8.

Although the foregoing subject matter has been described in some detail by way of illustration and example for purposes of clarity of understanding, it will be understood by those skilled in the art that certain changes and modifications can be practiced within the scope of the appended claims.

---

SEQUENCE LISTING:

SEQ ID NO.: 1
WL12 amino acid sequence = Cyclo-(-Ac-Tyr-NMeAla-Asn-Pro-His-Leu-Hyp-Trp-Ser-Trp(methyl)-NMeNle-NMeNle-Lys-Cys-)-Gly-NH2)

SEQ ID NO.: 2
DK-A-221 amino acid sequence = Cyclo-(-Ac-Tyr-NMeAla-Asn-Pro-His-Glu-Hyp-Trp-Ser-Trp(Carboxy-methyl)-NMeNle-NMeNle-Lys-Cys-)-Gly-NH2

---

That which is claimed:

1. A compound of formula (II):

DK-A-221-(L)$_n$-Rpt            (II);

wherein:

n is an integer selected from the group consisting of 0 and 1;

L is a linker, when present, is attached to a primary amine group of the compound of formula (II); and Rpt is a reporting moiety; and wherein the reporting moiety is attached directly or through the linker, when present, to a primary amine group of an amino acid of the compound of formula (II).

2. The compound of claim 1, wherein the reporting moiety is selected from the group consisting of a chelating agent, a radiolabeled substrate, a fluorescent dye, a photoacoustic reporting molecule, and a Raman-active reporting molecule.

3. The compound of claim 2, wherein the reporting moiety is a chelating agent and the chelating agent is selected from the group consisting of DOTAGA (1,4,7,10-tetraazacyclododececane, 1-(glutaric acid)-4,7,10-triacetic acid), DOTA (1,4,7,10-tetraazacyclododecane-1,4,7,10-tetraacetic acid), DOTASA (1,4,7,10-tetraazacyclododecane-1-(2-succinic acid)-4,7,10-triacetic acid), CB-DO2A (10-bis(carboxymethyl)-1,4,7,10-tetraazabicyclo[5.5.2]tetradecane), DEPA (7-[2-(Bis-carboxymethylamino)-ethyl]-4,10-bis-carboxymethyl-1,4,7,10-tetraaza-cyclododec-1-yl-acetic acid)), 3p-C-DEPA (2-[(carboxymethyl)][5-(4-nitrophenyl-1-[4,7,10-tris(carboxymethyl)-1,4,7,10-tetraazacyclododecan-1-yl]pentan-2-yl)amino]acetic acid)), TCMC (2-(4-isothiocyanotobenzyl)-1,4,7,10-tetraaza-1,4,7,10-tetra-(2-carbamonyl methyl)-cyclododecane), oxo-DO3A (1-oxa-4,7,10-triazacyclododecane-5-S-(4-isothiocyanatobenzyl)-4,7,10-triacetic acid), p-NH$_2$-Bn-Oxo-DO3A (1-Oxa-4,7,10-tetraazacyclododecane-5-S-(4-aminobenzyl)-4,7,10-triacetic acid), TE2A ((1,8-NX-bis-(carboxymethyl)-1,4,8,11-tetraazacyclotetradecane), MM-TE2A, DM-TE2A, CB-TE2A (4,11-bis(carboxymethyl)-1,4,8,11-tetraazabicyclo[6.6.2]hexadecane), CB-TE1A1P (4,8,11-tetraazacyclotetradecane-1-(methanephosphonic acid)-8-(methanecarboxylic acid), CB-TE2P (1,4,8,11-tetraazacyclotetradecane-1,8-bis(methanephosphonic acid), TETA (1,4,8,11-tetraazacyclotetradecane-1,4,8,11-tetraacetic acid), NOTA (1,4,7-triazacyclononane-N,N',N''-triacetic acid), NODA (1,4,7-triazacyclononane-1,4-diacetate), NODAGA (1,4,7-triazacyclononane, 1-glutaric acid-4,7-acetic acid), NOTAGA (1,4,7-triazonane-1,4-diyl)diacetic acid), DFO (Desferoxamine), NETA ([4-[2-(bis-carboxymethylamino)-ethyl]-7-carboxymethl-[1,4,7]triazonan-1-yl}-acetic acid), TACN-TM (N,N',N'', tris(2-mercaptoethyl)-1,4,7-triazacyclononane), Diamsar (1,8-Diamino-3,6,10,13,16,19-hexaazabicyclo(6,6,6)eicosane, 3,6,10,13,16,19-Hexaazabicyclo[6.6.6]eicosane-1,8-diamine), Sarar (1-N-(4-aminobenzyl)-3, 6,10,13,16,19-hexaazabicyclo[6.6.6] eicosane-1,8-diamine), AmBaSar (4-((8-amino-3,6,10,13,16,19-hexaazabicyclo [6.6.6] icosane-1-ylamino) methyl) benzoic acid), and BaBaSar.

4. The compound of claim 2, wherein the chelating agent is selected from the group consisting of:

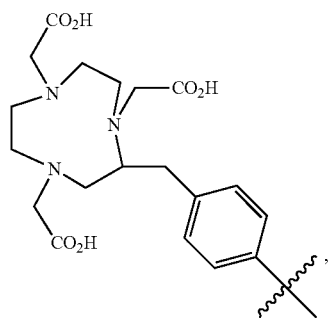

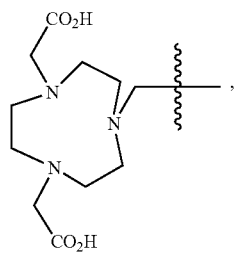

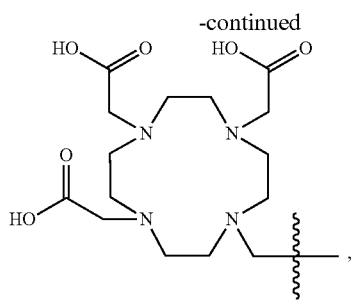

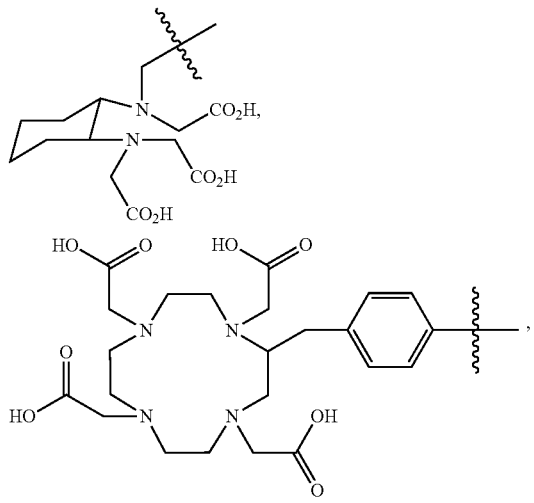

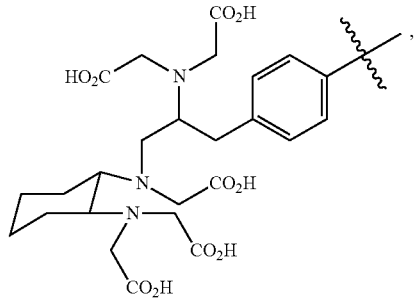

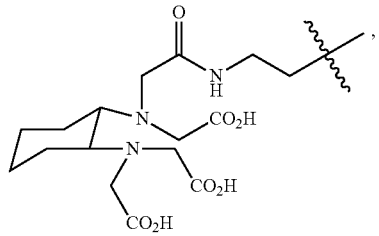

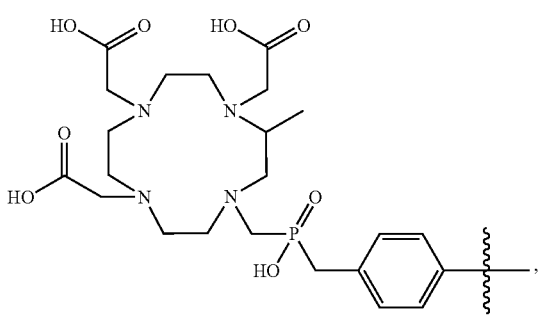

55
-continued
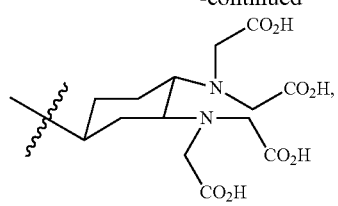
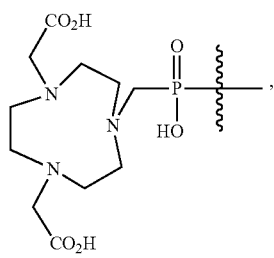
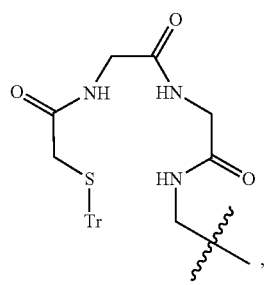
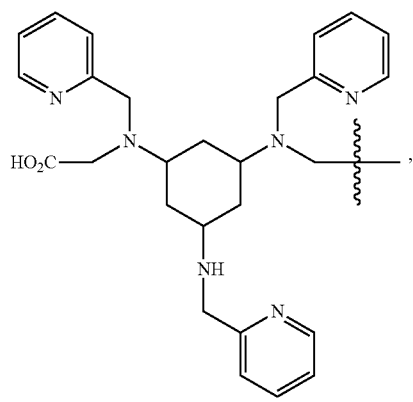
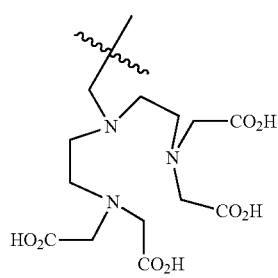
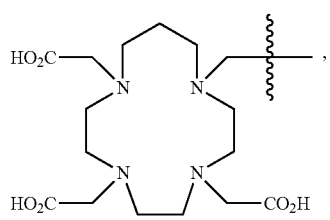
56
-continued
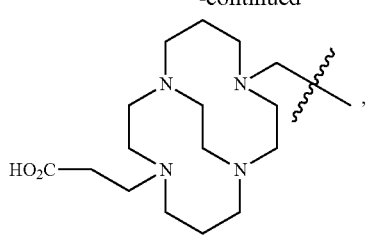
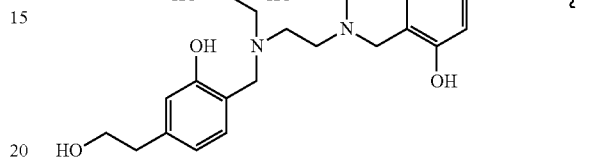
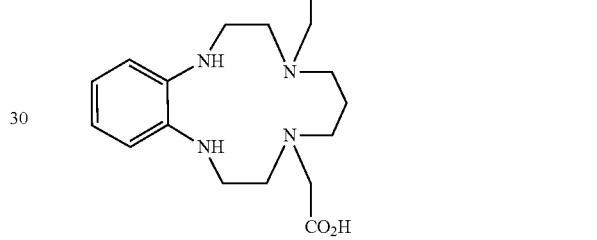
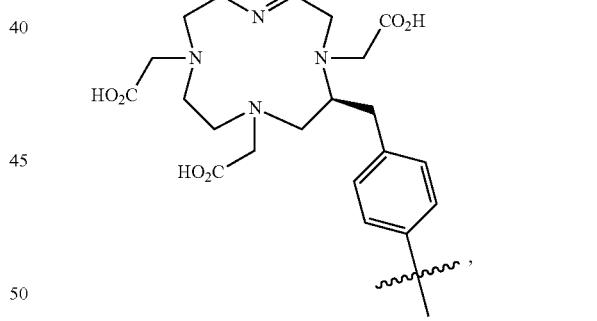
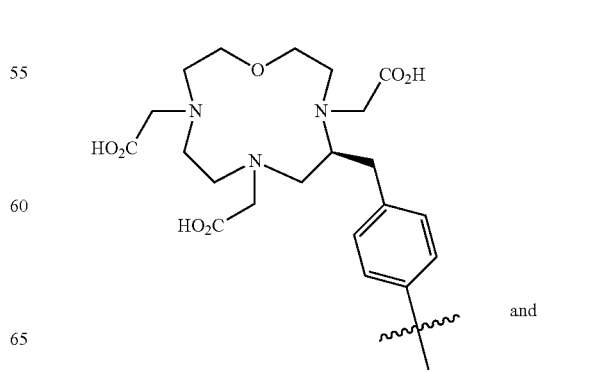
and -continued

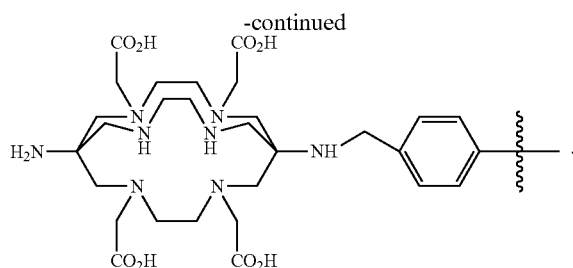

5. The compound of claim 2, wherein the reporting moiety is:

(a) a chelating agent and the chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, and $^{166}$Dy;

(b) a radiolabeled substrate and the radiolabeled substrate comprises a radioisotope selected from the group consisting of $^{11}$C, $^{13}$N, $^{15}$O, $^{123}$I, $^{124}$I, $^{125}$I, $^{126}$I, $^{131}$I, $^{75}$Br, $^{76}$Br, $^{77}$Br, $^{80}$Br, $^{80m}$Br, $^{82}$Br, $^{83}$Br, $^{18}$F, $^{211}$At, and an $^{18}$F-labeled substrate, wherein the $^{18}$F-labeled substrate is selected from the group consisting of 2-fluoro-PABA, 3-fluoro-PABA, 2-fluoro-mannitol, and N-succinimidyl-4-fluorobenzoate;

(c) a fluorescent dye and the fluorescent dye is selected from the group consisting of a carbocyanine, indocarbocyanine, oxacarbocyanine, thuicarbocyanine, merocyanine, polymethine, coumarin, rhodamine, xanthene, fluorescein, and a boron-dipyrromethane dye;

(d) a photoacoustic reporting molecule and the photoacoustic reporting molecule is a dye or a nanoparticle; wherein the dye comprises a fluorescent dye selected from the group consisting of indocyanine-green (ICG), Evans Blue, Methylene Blue, PPCy-C8, and Cypate-C18 and wherein the nanoparticle is selected from the group consisting of a plasmonic nanoparticle, a quantum dot, a nanodiamond, a polypyrrole nanoparticle, a copper sulfide nanoparticle, a graphene nanosheet, an iron oxide-gold core-shell nanoparticle, a $Gd_2O_3$ nanoparticle, a single-walled carbon nanotube, a dye-loaded perfluorocarbon nanoparticle, and a superparamagnetic iron oxide nanoparticle; or (e) a Raman-active reporting molecule and the Raman-active reporting molecule is selected from the group consisting of a single-walled carbon nanotube (SWNT) and a surface-enhanced Raman scattering (SERS) agent; wherein the SERS agent comprises a metal nanoparticle labeled with a Raman-active reporter molecule; and wherein the Raman-active reporter molecule comprises a fluorescent dye; and wherein the fluorescent dye is selected from the group consisting of a carbocyanine, rhodamine, and a chalcogenopyrylium dye.

6. The compound of claim 2, wherein the linker is selected from the group consisting of:

(a)

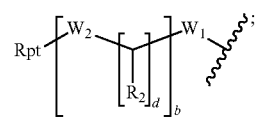

wherein:
Rpt is the reporting moiety;
$W_1$ is selected from the group consisting of $C_1$-$C_6$ alkylene, $C_3$-$C_6$ cycloalkylene, and arylene;
$W_2$ is selected from the group consisting of —NR$^1$—(C=O)—, —NR$^1$—(C=S)—, —(C=O)—NR$^1$—, —(C=S)—NR$^1$—, and —S—, wherein each R$^1$ is independently H or $C_1$-$C_4$ alkyl;
each $R_2$ is independently H or —COOR$_3$, wherein each $R_3$ is independently H, $C_1$-$C_6$ alkyl, $C_2$-$C_{12}$ aryl or $C_4$-$C_{16}$ alkylaryl;
b is an integer selected from the group consisting of 0, 1, 2, and 3;
d is an integer selected from the group consisting of 1, 2, 3, 4, 5, 6, 7, and 8; and
wherein the wavy line indicates a point of attachment between the linker and the primary amine group;

(b) Rpt-X—Y—Z—W$_3$— wherein:
Rpt is the reporting moiety;
X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_4$;
Y and $W_3$ are each independently —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—, —CO—NH—, —CO$_2$—NH—, —CO—NR$_B$—, —CO$_2$—NR$_B$—, or a bond;
p is 0, 1, or 2;
$R_A$, for each occurrence, is halogen, hydroxy, amino, cyano, nitro, $CO_2H$, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and R$_B$, for each occurrence, is optionally substituted alkyl, optionally substituted alkoxy, optionally substituted mono or dialkylamino, optionally substituted alkylthio, optionally substituted aryl, or optionally substituted heteroaryl; and (c) an amino acid linker.

7. The compound of claim 1, wherein the compound is a compound of formula (II), n is 0, the reporting moiety comprises a NODAGA chelating agent, and the compound has the following structure:

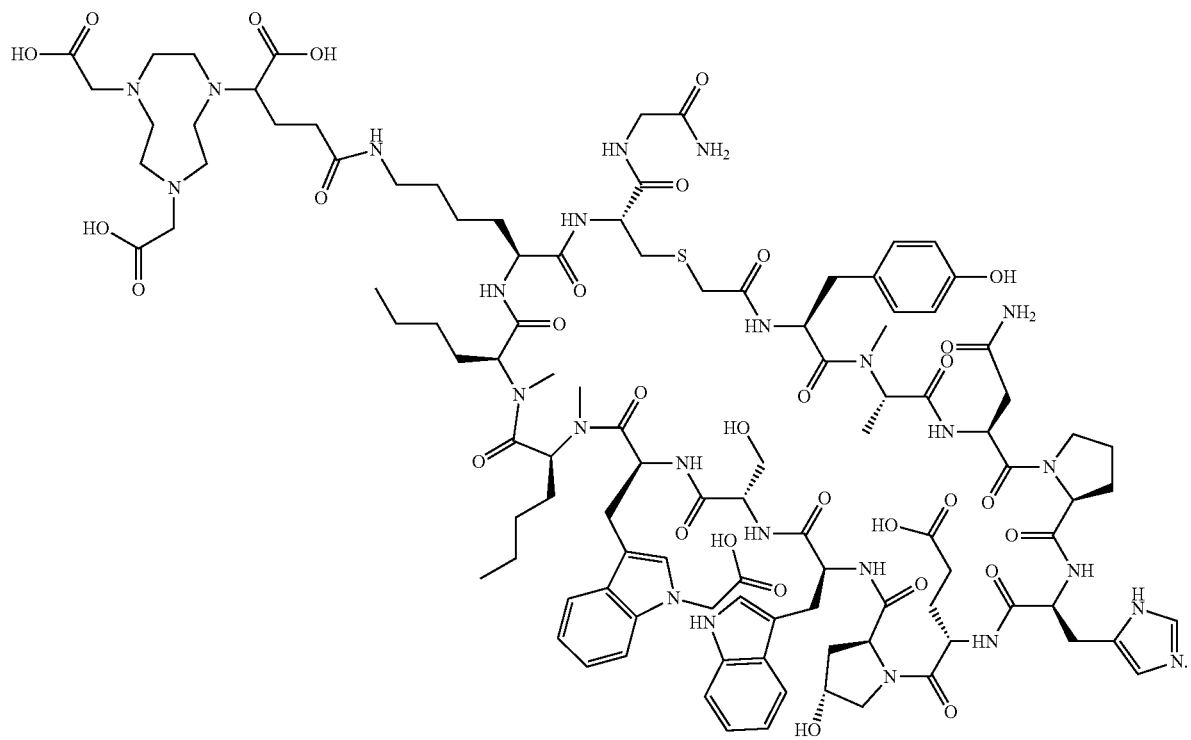 [SMILES: CCCC[C@H]1C(=O)N(C)[C@@H](CCCC)C(=O)N[C@@H](CCCCNC(=O)CCC(C(=O)O)N2CCN(CC(=O)O)CCN(CC(=O)O)CC2)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

8. The compound of claim 7, wherein the NODAGA chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, $^{166}$Dy, and Al$^{18}$F.

9. The compound of claim 1, wherein the compound is a compound of formula (II), n is 0, the reporting moiety comprises a DOTA chelating agent, and the compound has the following structure:

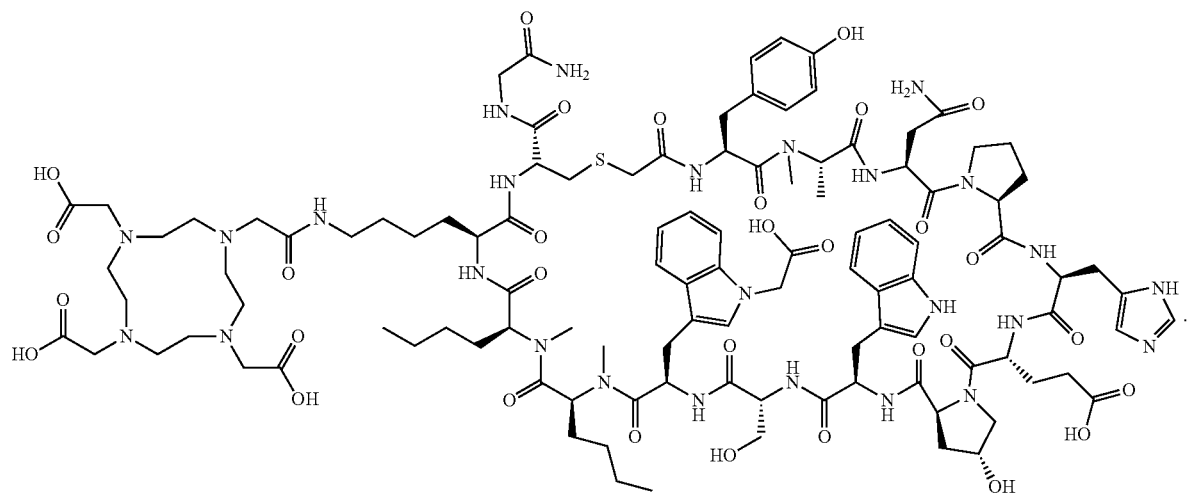

10. The compound of claim 9, wherein the DOTA chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, $^{166}$Dy, and Al$^{18}$F.

11. The compound of claim 1, wherein the compound is a compound of formula (II), n is 0, the reporting moiety comprises a DOTAGA chelating agent, and the compound has the following structure:

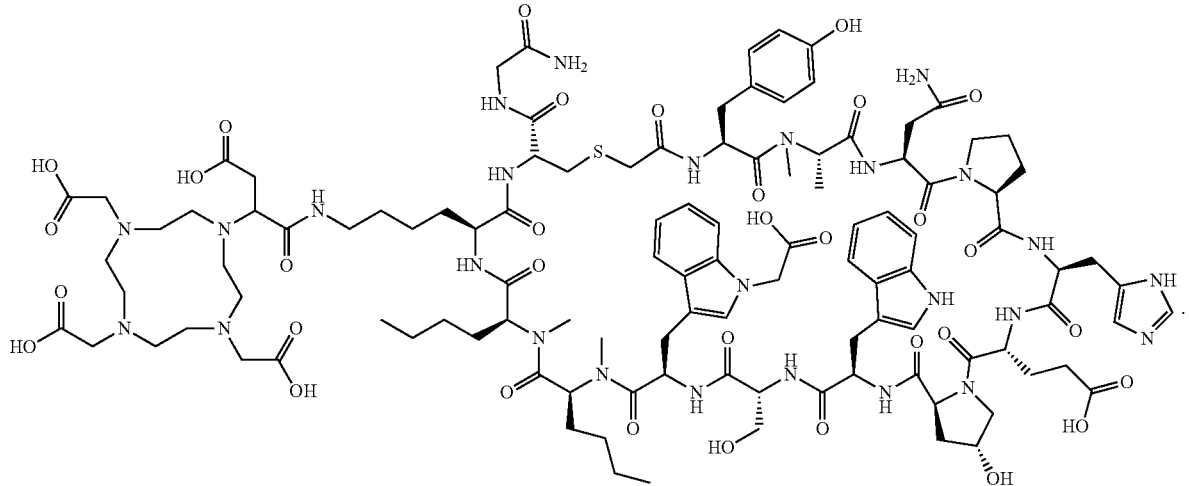

12. The compound of claim 11, wherein the DOTAGA chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, $^{166}$Dy, and Al$^{18}$F.

13. The compound of claim 1, wherein the compound comprises:

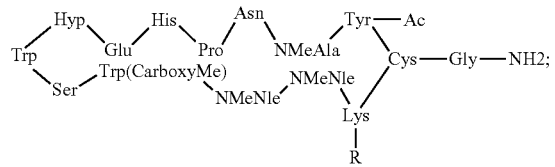

wherein R is a reporting moiety comprising a chelating agent selected from the group consisting of NODA and NOTA.

14. The compound of claim 1, wherein the compound is a compound of formula (II):

DK-A-221-(L)$_n$-Rpt                                (II);

wherein:
n is an integer selected from the group consisting of 0 and 1;
L is a linker, when present, is attached to a primary amine group of the compound of formula (II); and
Rpt is a reporting moiety comprising a chelating agent selected from the group consisting of DOTAGA (1,4,7,10-tetraazacyclododececane, 1-(glutaric acid)-4,7,10-triacetic acid), DOTA (1,4,7,10-tetraazacyclododecane-1,4,7,10-tetraacetic acid), DOTASA (1,4,7,10-tetraazacyclododecane-1-(2-succinic acid)-4,7,10-triacetic acid), CB-DO2A (10-bis(carboxymethyl)-1,4,7,10-tetraazabicyclo[5.5.2]tetradecane), DEPA (7-[2-(Bis-carboxymethylamino)-ethyl]-4,10-bis-carboxymethyl-1,4,7,10-tetraaza-cyclododec-1-yl-acetic acid)), 3p-C-DEPA (2-[(carboxymethyl)][5-(4-nitrophenyl-1-[4,7,10-tris(carboxymethyl)-1,4,7,10-tetraazacyclododecan-1-yl]pentan-2-yl)amino]acetic acid)), TCMC (2-(4-isothiocyanotobenzyl)-1,4,7,10-tetraaza-1,4,7,10-tetra-(2-carbamonyl methyl)-cyclododecane), oxo-DO3A (1-oxa-4,7,10-triazacyclodo-decane-5-S-(4-isothiocyanatobenzyl)-4,7,10-triacetic acid), p-NH$_2$-Bn-Oxo-DO3A (1-Oxa-4,7,10-tetraaza-cyclododecane-5-S-(4-aminobenzyl)-4,7,10-triacetic acid), TE2A ((1,8-NX-bis-(carboxymethyl)-1,4,8,11-tetraazacyclotetradecane), MM-TE2A, DM-TE2A, CB-TE2A (4,11-bis(carboxymethyl)-1,4,8,11-tetraazabicyclo[6.6.2]hexadecane), CB-TE1A1P (4,8,11-tetraazacyclotetradecane-1-(methanephosphonic acid)-8-(methanecarboxylic acid), CB-TE2P (1,4,8,11-tetraazacyclotetradecane-1,8-bis(methanephosphonic acid), TETA (1,4,8,11-tetraazacyclotetradecane-1,4,8,11-tetraacetic acid), NOTA (1,4,7-triazacyclononane-N,N',N''-triacetic acid), NODA (1,4,7-triazacyclo-nonane-1,4-diacetate), NODAGA (1,4,7-triazacyclononane, 1-glutaric acid-4,7-acetic acid), NOTAGA (1,4,7-triazonane-1,4-diyl)diacetic acid) DFO (Desferoxamine), NETA ([4-[2-(bis-carboxymethylamino)-ethyl]-7-carboxymethl-[1,4,7]triazonan-1-yl}-acetic acid), TACN-TM (N,N',N''', tris(2-mercaptoethyl)-1,4,7-triazacyclononane), Diamsar (1,8-Diamino-3,6,10,13,16,19-hexaazabicyclo(6,6,6) eicosane, 3,6,10,13,16,19-Hexaazabicyclo[6.6.6] eicosane-1,8-diamine), Sarar (1-N-(4-aminobenzyl)-3,6,10,13,16,19-hexaazabicyclo[6.6.6] eicosane-1,8-diamine), AmBaSar (4-((8-amino-3,6,10,13,16,19-hexaazabicyclo [6.6.6] icosane-1-ylamino) methyl) benzoic acid), and BaBaSar; and
wherein the reporting moiety is attached to a primary amine group of an amino acid of the compound of formula (II).

15. The compound of claim 14, wherein the reporting moiety is NODA.

16. The compound of claim 14, wherein the linker, L, when present, is attached to a $^{13}$lysine (Lys) primary amine group of the compound of formula (II).

17. The compound of claim 1, wherein the linker, L, when present, is attached to a $^{13}$lysine (Lys) primary amine group of the compound of formula (II).

18. An imaging method for detecting Programmed Death Ligand 1 (PD-L1), the method comprising:
(a) providing an effective amount of a compound of claim 1;
(b) contacting one or more cells or tissues with the compound; and
(c) making an image to detect PD-L1.

19. The imaging method of claim 18, wherein contacting of the one or more cells or tissues with the compound is performed in vitro, in vivo, or ex vivo.

20. The imaging method of claim 19, wherein contacting of the one or more cells or tissues with the compound comprises administering the compound to a subject.

21. The imaging method of claim 20, wherein the subject is a human, rat, mouse, cat, dog, horse, sheep, cow, monkey, avian, or amphibian.

22. The imaging method of claim 20, wherein detection of the PD-L1 occurs at about 60-120 minutes or less after of administering the compound to the subject.

23. The imaging method of claim 18, wherein the imaging method is used to detect:
(a) a cancer, wherein the cancer is selected from the group consisting of a blastoma, a carcinoma, a glioma, a leukemia, a lymphoma, a melanoma, a myeloma, a sarcoma, head cancer, neck cancer, head and neck cancer, lung cancer, breast cancer, triple negative breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, renal cancer, bladder cancer, brain cancer, adenoma, and a metastatic cancer;
(b) a solid tumor, wherein the solid tumor is in an organ selected from the group consisting of brain, colon, breast, prostate, liver, kidney, lung, esophagus, head and neck, ovary, cervix, stomach, rectum, bladder, uterus, testes, and pancreas;
(c) an infection, including a microbial infection, wherein the microbial infection is selected from the group consisting of an infection due to one or more microorganisms selected from the group consisting of *Mycobacterium tuberculosis, E. coli, Klebsiella* sp., *Enterobacter* sp., *Proteus* sp., *Serratia marcescens, Pseudomonas aeruginosa, Staphylococcus* spp., including *S. aureus* and coag.-negative *Staphylococcus, Enterococcus* sp., *Streptococcus pneumoniae, Haemophilus influenzae, Bacteroides* spp., *Acinetobacter* spp., *Helicobacter* spp., *Candida* sp., methicillin-resistant *Staphylococcus aureus* (MRSA) and vancomycin-resistant *Enterococcus faecalis* (VRE);
(d) inflammation, wherein the inflammation is related to a disorder selected from the group consisting of asthma, an autoimmune disease, an autoinflammatory disease, Celiac disease, diverticulitis, glomerulonephritis, hidradenitis suppurativa, a hypersensitivity, an inflammatory bowel disease, interstitial cystitis, otitis, pelvic inflammatory disease, reperfusion injury, rheumatic fever, rheumatoid arthritis, sarcoidosis, transplant rejection, lupus, systemic lupus erythematosus, and vasculitis, or wherein the inflammation is caused by rheumatoid arthritis or systemic lupus erythematosus;
(e) one or more immune cells in a tumor;
(f) systemic distribution of immune cells in a tumor or in a subject;
(g) an immune cell response to an infectious disease;
(h) an immune cell response in a tumor or a normal tissue response to an inflammatory disease;
(i) PD-L1 expression levels; or
(j) an occupancy or target engagement by antibodies or peptides or low molecular weight agents of PD-L1 at a tumor site or in normal tissue.

24. A kit for detecting Programmed Death Ligand 1 (PD-L1), the kit comprising the compound of claim 1 and instructions for use.

25. A compound of formula (I):

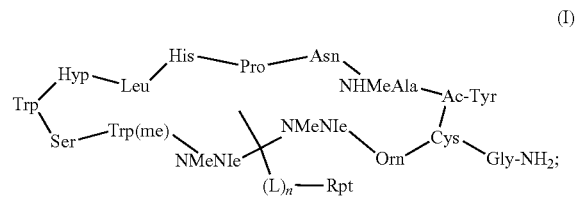

wherein:
n is an integer selected from the group consisting of 0 and 1;
L is a linker, when present, is attached to a primary amine group of the compound of formula (I); and
Rpt is a reporting moiety; and
wherein the reporting moiety is attached directly or through the linker, when present, to a primary amine group of an amino acid of the compound of formula (I).

26. The compound of claim 25, wherein the reporting moiety is selected from the group consisting of a chelating agent, a radiolabeled substrate, a fluorescent dye, a photoacoustic reporting molecule, and a Raman-active reporting molecule.

27. The compound of claim 26, wherein the reporting moiety is a chelating agent and the chelating agent is selected from the group consisting of DOTAGA (1,4,7,10-tetraazacyclododececane, 1-(glutaric acid)-4,7,10-triacetic acid), DOTA (1,4,7,10-tetraazacyclododecane-1,4,7,10-tetraacetic acid), DOTASA (1,4,7,10-tetraazacyclododecane-1-(2-succinic acid)-4,7,10-triacetic acid), CB-DO2A (10-bis(carboxymethyl)-1,4,7,10-tetraazabicyclo[5.5.2]tetradecane), DEPA (7-[2-(Bis-carboxymethylamino)-ethyl]-4,10-bis-carboxymethyl-1,4,7,10-tetraaza-cyclododec-1-yl-acetic acid)), 3p-C-DEPA (2-[(carboxymethyl)][5-(4-nitrophenyl-1-[4,7,10-tris(carboxymethyl)-1,4,7,10-tetraazacyclododecan-1-yl]pentan-2-yl)amino]acetic acid)), TCMC (2-(4-isothiocyanotobenzyl)-1,4,7,10-tetraaza-1,4,7,10-tetra-(2-carbamonyl methyl)-cyclododecane), oxo-DO3A (1-oxa-4,7,10-triazacyclododecane-5-S-(4-isothiocyanatobenzyl)-4,7,10-triacetic acid), p-NH$_2$-Bn-Oxo-DO3A (1-Oxa-4,7,10-tetraazacyclododecane-5-S-(4-aminobenzyl)-4,7,10-triacetic acid), TE2A ((1,8-N,N'-bis-(carboxymethyl)-1,4,8,11-tetraazacyclotetradecane), MM-TE2A, DM-TE2A, CB-TE2A (4,11-bis(carboxymethyl)-1,4,8,11-tetraazabicyclo[6.6.2]hexadecane), CB-TE1A1P (4,8,11-tetraazacyclotetradecane-1-(methanephosphonic acid)-8-(methanecarboxylic acid), CB-TE2P (1,4,8,11-tetraazacyclotetradecane-1,8-bis(methanephosphonic acid), TETA (1,4,8,11-tetraazacyclotetradecane-1,4,8,11-tetraacetic acid), NOTA (1,4,7-triazacyclononane-N,N',N"-triacetic acid), NODA (1,4,7-triazacyclononane-1,4-diacetate), NODAGA (1,4,7-triazacyclononane, 1-glutaric acid-4,7-acetic acid), NOTAGA (1,4,7-triazonane-1,4-diyl)diacetic acid), DFO (Desferoxamine), NETA ([4-[2-(bis-carboxymethylamino)- ethyl]-7-carboxymethl-[1,4,7]triazonan-1-yl}-acetic acid), TACN-TM (N,N',N'', tris(2-mercaptoethyl)-1,4,7-triazacyclononane), Diamsar (1,8-Diamino-3,6,10,13,16,19-hexaazabicyclo(6,6,6)eicosane, 3,6,10,13,16,19-Hexaazabicyclo[6.6.6]eicosane-1,8-diamine), Sarar (1-N-(4-aminobenzyl)-3,6,10,13,16,19-hexaazabicyclo[6.6.6] eicosane-1,8-diamine), AmBaSar (4-((8-amino-3,6,10,13,16,19-hexaazabicyclo [6.6.6] icosane-1-ylamino) methyl) benzoic acid), and BaBaSar.

28. The compound of claim 27, wherein the chelating agent is selected from the group consisting of:

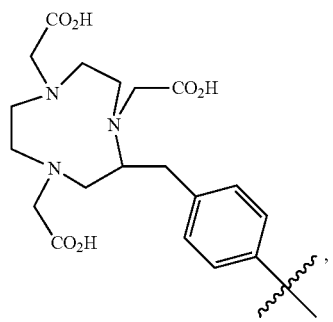

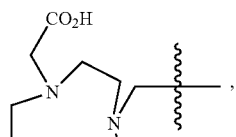

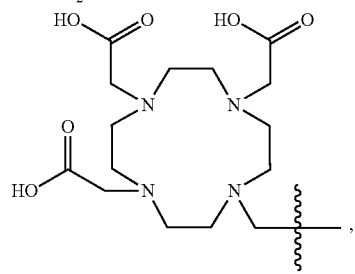

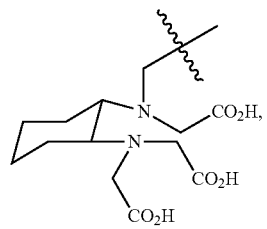

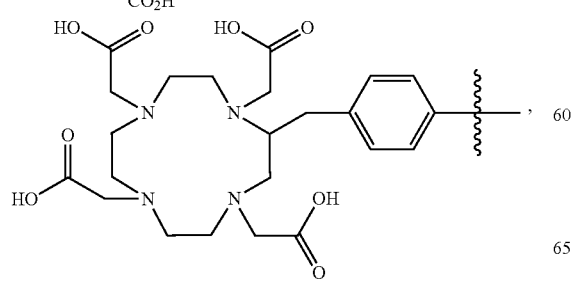

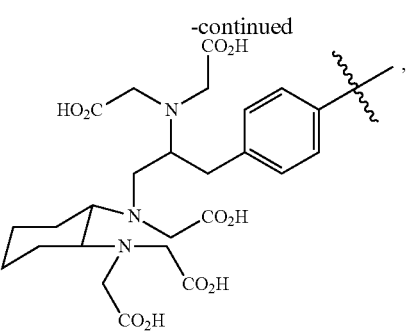

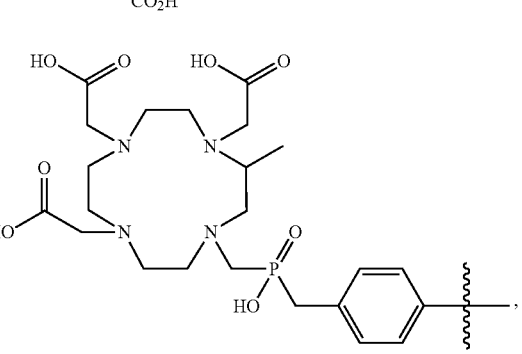

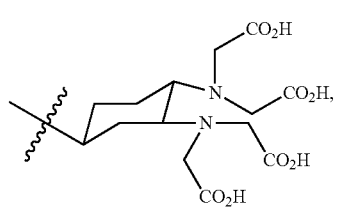

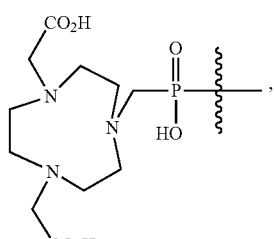

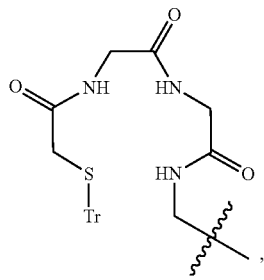

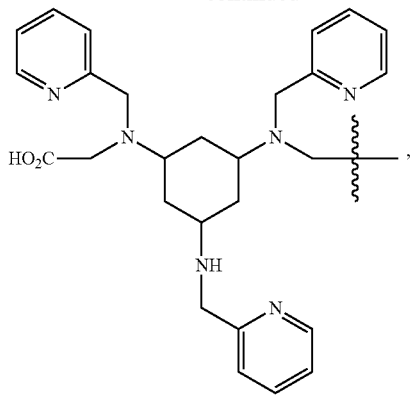
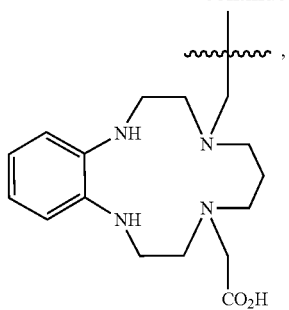
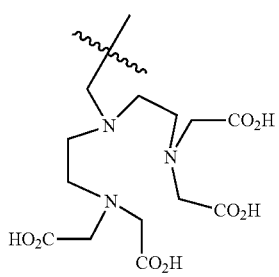
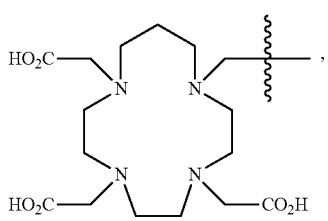
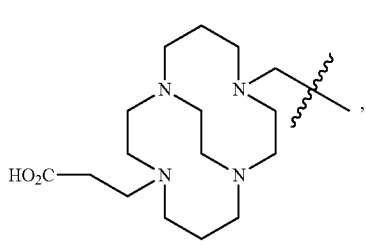
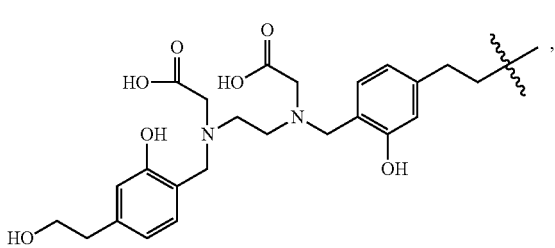
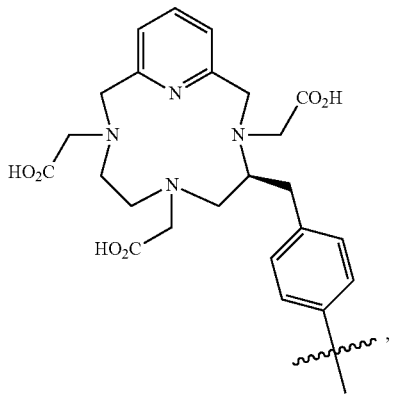
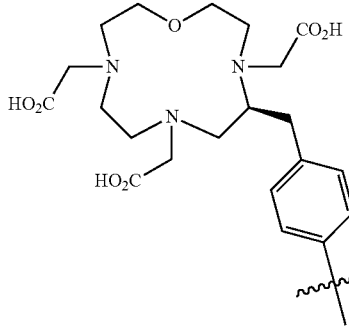
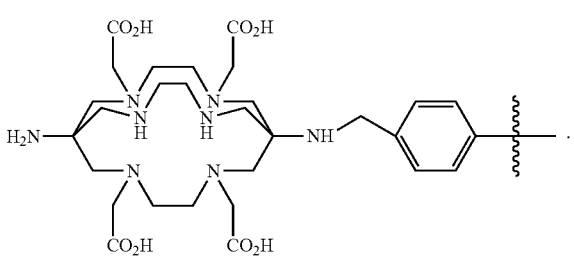
and
29. The compound of claim 27, wherein the reporting moiety comprises a DOTAGA chelating agent; the DOTAGA chelating agent further comprises a $^{64}$Cu radiometal; and the compound of formula (I) is:

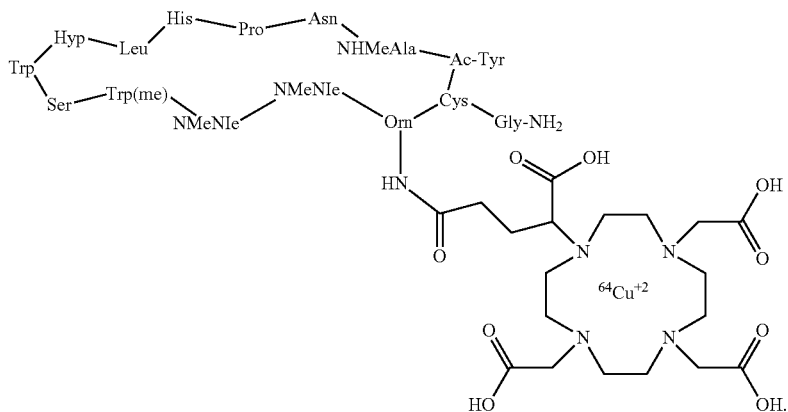

30. The compound of claim 26, wherein the reporting moiety is:

(a) a chelating agent and the chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, and $^{166}$Dy;

(b) a radiolabeled substrate and the radiolabeled substrate comprises a radioisotope selected from the group consisting of $^{11}$C, $^{13}$N, $^{15}$O, $^{123}$I, $^{124}$I, $^{125}$I, $^{126}$I, $^{131}$I, $^{75}$Br, $^{76}$Br, $^{77}$Br, $^{80}$Br, $^{80m}$Br, $^{82}$Br, $^{83}$Br, $^{18}$F, $^{211}$At, and an $^{18}$F-labeled substrate, wherein the $^{18}$F-labeled substrate is selected from the group consisting of 2-fluoro-PABA, 3-fluoro-PABA, 2-fluoro-mannitol, and N-succinimidyl-4-fluorobenzoate;

(c) a fluorescent dye and the fluorescent dye is selected from the group consisting of a carbocyanine, indocarbocyanine, oxacarbocyanine, thuicarbocyanine, merocyanine, polymethine, coumarin, rhodamine, xanthene, fluorescein, and a boron-dipyrromethane dye;

(d) a photoacoustic reporting molecule and the photoacoustic reporting molecule is a dye or a nanoparticle; wherein the dye comprises a fluorescent dye selected from the group consisting of indocyanine-green (ICG), Evans Blue, Methylene Blue, PPCy-C8, and Cypate-C18 and wherein the nanoparticle is selected from the group consisting of a plasmonic nanoparticle, a quantum dot, a nanodiamond, a polypyrrole nanoparticle, a copper sulfide nanoparticle, a graphene nanosheet, an iron oxide-gold core-shell nanoparticle, a $Gd_2O_3$ nanoparticle, a single-walled carbon nanotube, a dye-loaded perfluorocarbon nanoparticle, and a superparamagnetic iron oxide nanoparticle; or (e) a Raman-active reporting molecule and the Raman-active reporting molecule is selected from the group consisting of a single-walled carbon nanotube (SWNT) and a surface-enhanced Raman scattering (SERS) agent; wherein the SERS agent comprises a metal nanoparticle labeled with a Raman-active reporter molecule; and wherein the Raman-active reporter molecule comprises a fluorescent dye; and wherein the fluorescent dye is selected from the group consisting of a carbocyanine, rhodamine, and a chalcogenopyrylium dye.

31. The compound of claim 25, wherein the linker is selected from the group consisting of:

(a)

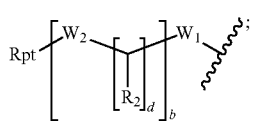

wherein:

Rpt is the reporting moiety;

$W_1$ is selected from the group consisting of $C_1$-$C_6$ alkylene, $C_3$-$C_6$ cycloalkylene, and arylene;

$W_2$ is selected from the group consisting of —$NR^1$—(C=O)—, —$NR^1$—(C=S)—, —(C=O)—$NR^1$—, —(C=S)—$NR^1$—, and —S—, wherein each $R^1$ is independently H or $C_1$-$C_4$ alkyl;

each $R_2$ is independently H or —$COOR_3$, wherein each $R_3$ is independently H, $C_1$-$C_6$ alkyl, $C_2$-$C_{12}$ aryl or $C_4$-$C_{16}$ alkylaryl;

b is an integer selected from the group consisting of 0, 1, 2, and 3;

d is an integer selected from the group consisting of 1, 2, 3, 4, 5, 6, 7, and 8; and wherein the wavy line indicates a point of attachment between the linker and the primary amine group;

(b) Rpt-X—Y—Z—$W_3$— wherein:

Rpt is the reporting moiety;

X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_A$;

Y and $W_3$ are each independently —O—, —S(O)$_p$—, —NH—, —$NR_B$—, —CH=CH—, —$CR_B$=CH—, —CH=$CR_B$—, —NH—CO—, —NH—$CO_2$—, —$NR_B$—CO—, —$NR_B$—$CO_2$—; —CO—NH—, —$CO_2$—NH—, —CO—$NR_B$—, —$CO_2$—$NR_B$—, or a bond;

p is 0, 1, or 2;

$R_A$, for each occurrence, is halogen, hydroxy, amino, cyano, nitro, $CO_2H$, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and RB, for each occurrence, is optionally substituted alkyl, optionally substituted alkoxy, optionally substituted mono or dialkylamino, optionally substituted alkylthio, optionally substituted aryl, or optionally substituted heteroaryl; and (c) an amino acid linker.

32. The compound of claim 25, wherein the compound is a compound of formula (I):

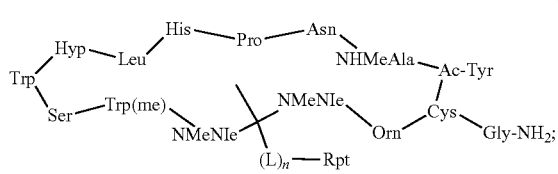

wherein:
n is an integer selected from the group consisting of 0 and 1;
L is a linker, when present, is attached to a primary amine group of the compound of formula (I); and
Rpt is a reporting moiety comprising a chelating agent selected from the group consisting of DOTAGA (1,4,7,10-tetraazacyclododececane, 1-(glutaric acid)-4,7,10-triacetic acid), DOTA (1,4,7,10-tetraazacyclododecane-1,4,7,10-tetraacetic acid), DOTASA (1,4,7,10-tetraazacyclododecane-1-(2-succinic acid)-4,7,10-triacetic acid), CB-DO2A (10-bis(carboxymethyl)-1,4,7,10-tetraazabicyclo[5.5.2]tetradecane), DEPA (7-[2-(Bis-carboxymethylamino)-ethyl]-4,10-bis-carboxymethyl-1,4,7,10-tetraaza-cyclododec-1-yl-acetic acid)), 3p-C-DEPA (2-[(carboxymethyl)][5-(4-nitrophenyl-1-[4,7,10-tris(carboxymethyl)-1,4,7,10-tetraazacyclododecan-1-yl]pentan-2-yl)amino]acetic acid)), TCMC (2-(4-isothiocyanotobenzyl)-1,4,7,10-tetraaza-1,4,7,10-tetra-(2-carbamonyl methyl)-cyclododecane), oxo-DO3A (1-oxa-4,7,10-triazacyclododecane-5-S-(4-isothiocyanatobenzyl)-4,7,10-triacetic acid), p-NH₂-Bn-Oxo-DO3A (1-Oxa-4,7,10-tetraaza-cyclododecane-5-S-(4-aminobenzyl)-4,7,10-triacetic acid), TE2A ((1,8-N,N'-bis-(carboxymethyl)-1,4,8,11-tetraazacyclotetradecane), MM-TE2A, DM-TE2A, CB-TE2A (4,11-bis(carboxymethyl)-1,4,8,11-tetraazabicyclo[6.6.2]hexadecane), CB-TE1A1P (4,8,11-tetraazacyclotetradecane-1-(methanephosphonic acid)-8-(methanecarboxylic acid), CB-TE2P (1,4,8,11-tetraazacyclotetradecane-1,8-bis(methanephosphonic acid), TETA (1,4,8,11-tetraazacyclotetradecane-1,4,8,11-tetraacetic acid), NOTA (1,4,7-triazacyclononane-N,N',N''-triacetic acid), NODA (1,4,7-triazacyclononane-1,4-diacetate), NODAGA (1,4,7-triazacyclononane, 1-glutaric acid-4,7-acetic acid), NOTAGA (1,4,7-triazonane-1,4-diyl)diacetic acid), DFO (Desferoxamine), NETA ([4-[2-(bis-carboxymethylamino)-ethyl]-7-carboxymethl-[1,4,7]triazonan-1-yl}-acetic acid), TACN-TM (N,N',N''', tris(2-mercaptoethyl)-1,4,7-triazacyclononane), Diamsar (1,8-Diamino-3,6,10,13,16,19-hexaazabicyclo(6,6,6) eicosane, 3,6,10,13,16,19-Hexaazabicyclo[6.6.6] eicosane-1,8-diamine), Sarar (1-N-(4-aminobenzyl)-3,6,10,13,16,19-hexaazabicyclo[6.6.6] eicosane-1,8-diamine), AmBaSar (4-((8-amino-3,6,10,13,16,19-hexaazabicyclo [6.6.6] icosane-1-ylamino) methyl) benzoic acid), and BaBaSar; and
wherein the reporting moiety is attached to a primary amine group of an amino acid of the compound of formula (I).

33. The compound of claim 32, wherein the NODAGA chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, $^{166}$Dy, and Al$^{18}$F.

34. The compound of claim 32, wherein the DOTA chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, $^{166}$Dy, and Al$^{18}$F.

35. The compound of claim 32, wherein the DOTAGA chelating agent further comprises a radiometal selected from the group consisting of $^{94m}$Tc, $^{99m}$Tc, $^{111}$In, $^{67}$Ga, $^{68}$Ga, $^{86}$Y, $^{90}$Y, $^{177}$Lu, $^{186}$Re, $^{188}$Re, $^{60}$Cu, $^{61}$Cu, $^{62}$Cu, $^{64}$Cu, $^{67}$Cu, $^{55}$Co, $^{57}$Co, $^{47}$Sc, $^{225}$Ac, $^{213}$Bi, $^{212}$Bi, $^{153}$Sm, $^{166}$Ho, $^{152}$Gd, $^{82}$Rb, $^{89}$Zr, $^{166}$Dy, and Al$^{18}$F.

36. The compound of claim 32, wherein the linker, L, when present, is attached to an $^{13}$ornithine (Orn) primary amine group of the compound of formula (I).

37. The of compound of claim 25, wherein the linker, L, when present, is attached to an $^{13}$ornithine (Orn) primary amine group of the compound of formula (I).

38. An imaging method for detecting Programmed Death Ligand 1 (PD-L1), the method comprising:
(a) providing an effective amount of a compound of claim 25;
(b) contacting one or more cells or tissues with the compound; and
(c) making an image to detect PD-L1.

39. The imaging method of claim 38, wherein contacting of the one or more cells or tissues with the compound is performed in vitro, in vivo, or ex vivo.

40. The imaging method of claim 39, wherein contacting of the one or more cells or tissues with the compound comprises administering the compound to a subject.

41. The imaging method of claim 40, wherein the subject is a human, rat, mouse, cat, dog, horse, sheep, cow, monkey, avian, or amphibian.

42. The imaging method of claim 40, wherein detection of the PD-L1 occurs at about 60-120 minutes or less after administering the compound to the subject.

43. The imaging method of claim 38, wherein the imaging method is used to detect:
(a) a cancer, wherein the cancer is selected from the group consisting of a blastoma, a carcinoma, a glioma, a leukemia, a lymphoma, a melanoma, a myeloma, a sarcoma, head cancer, neck cancer, head and neck cancer, lung cancer, breast cancer, triple negative breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, renal cancer, bladder cancer, brain cancer, adenoma, and a metastatic cancer;
(b) a solid tumor, wherein the solid tumor is in an organ selected from the group consisting of brain, colon, breast, prostate, liver, kidney, lung, esophagus, head and neck, ovary, cervix, stomach, rectum, bladder, uterus, testes, and pancreas;

(c) an infection, including a microbial infection, wherein the microbial infection is selected from the group consisting of an infection due to one or more microorganisms selected from the group consisting of *Mycobacterium tuberculosis, E. coli, Klebsiella* sp., *Enterobacter* sp., *Proteus* sp., *Serratia marcescens, Pseudomonas aeruginosa, Staphylococcus* spp., including *S. aureus* and coag.-negative *Staphylococcus, Enterococcus* sp., *Streptococcus pneumoniae, Haemophilus influenzae, Bacteroides* spp., *Acinetobacter* spp., *Helicobacter* spp., *Candida* sp., methicillin-resistant *Staphylococcus aureus* (MRSA) and vancomycin-resistant *Enterococcus faecalis* (VRE);

(d) inflammation, wherein the inflammation is related to a disorder selected from the group consisting of asthma, an autoimmune disease, an autoinflammatory disease, Celiac disease, diverticulitis, glomerulonephritis, hidradenitis suppurativa, a hypersensitivity, an inflammatory bowel disease, interstitial cystitis, otitis, pelvic inflammatory disease, reperfusion injury, rheumatic fever, rheumatoid arthritis, sarcoidosis, transplant rejection, lupus, systemic lupus erythematosus, and vasculitis, or wherein the inflammation is caused by rheumatoid arthritis or systemic lupus erythematosus;

(e) one or more immune cells in a tumor;

(f) systemic distribution of immune cells in a tumor or in a subject;

(g) an immune cell response to an infectious disease;

(h) an immune cell response in a tumor or a normal tissue response to an inflammatory disease;

(i) PD-L1 expression levels; or (j) an occupancy or target engagement by antibodies or peptides or low molecular weight agents of PD-L1 at a tumor site or in normal tissue.

44. A kit for detecting Programmed Death Ligand 1 (PD-L1), the kit comprising the compound of claim 25 and instructions for use.

* * * * *